(12) United States Patent
Rittenhouse-Olson et al.

(10) Patent No.: US 11,130,821 B2
(45) Date of Patent: *Sep. 28, 2021

(54) HUMANIZED ANTI-TF-ANTIGEN ANTIBODIES

(71) Applicant: The Research Foundation for The State University of New York, Amherst, NY (US)

(72) Inventors: Kate Rittenhouse-Olson, Williamsville, NY (US); Julia Abdullah, Amherst, NY (US); Jing Ying Eng, Selangor (MY); Stephen T. Koury, Williamsville, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 650 days.

This patent is subject to a terminal disclaimer.

(21) Appl. No.: 15/976,500

(22) Filed: May 10, 2018

(65) Prior Publication Data

US 2018/0258182 A1 Sep. 13, 2018

Related U.S. Application Data

(63) Continuation of application No. 15/296,411, filed on Oct. 18, 2016, which is a continuation-in-part of application No. PCT/US2015/026595, filed on Apr. 20, 2015.

(60) Provisional application No. 61/981,240, filed on Apr. 18, 2014.

(51) Int. Cl.
*C07K 16/30* (2006.01)
*C07K 16/28* (2006.01)
*C07K 16/44* (2006.01)
*A61K 39/00* (2006.01)

(52) U.S. Cl.
CPC ...... *C07K 16/3076* (2013.01); *C07K 16/2896* (2013.01); *C07K 16/44* (2013.01); *A61K 2039/505* (2013.01); *C07K 2317/24* (2013.01); *C07K 2317/33* (2013.01); *C07K 2317/565* (2013.01); *C07K 2317/567* (2013.01); *C07K 2317/73* (2013.01); *C07K 2317/732* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,374,755 | B2 | 5/2008 | Rittenhouse-Olson | |
| 10,023,651 | B2 * | 7/2018 | Rittenhouse-Olson | ................... C07K 16/3076 |
| 2005/0260680 | A1 | 11/2005 | Yeaman et al. | |
| 2006/0018913 | A1 | 1/2006 | Rittenhouse-Olson | |
| 2007/0253950 | A1 | 11/2007 | Jacobson | |
| 2008/0226561 | A1 | 9/2008 | Rittenhouse-Olson | |
| 2011/0117086 | A1 | 5/2011 | Pannequin et al. | |

FOREIGN PATENT DOCUMENTS

| EP | 2161031 A1 | 3/2010 |
| EP | 2347769 A1 | 7/2011 |
| EP | 2407487 A1 | 1/2012 |
| EP | 2787081 A1 | 10/2014 |
| JP | 2008507584 A | 3/2008 |
| RU | 2491294 C2 | 8/2013 |

OTHER PUBLICATIONS

Tessier, M.B., et al., Computational Screening of the Human TF-Glycome Provides a Structural Definition for the Specificity of Anti-Tumor Antibody JAA-F11, PLoS One, Jan. 2013, vol. 8, No. 1, e54874 (10 pages).

Rittenhouse-Diakun, K., et al., Development and Characterization of Monoclonal Antibody to T-Antigen: (Galbeta1-3GalNac-alpha-O), Hybridoma, Nov. 2, 1998, vol. 17, No. 2, 1998; pp. 165-173.

Shigeoka, H., et al.Inhibition of liver mestastases from neuraminidase-treated colon 26 cells by an anti-Thomsen-Friedenreich-specific monoclonal antibody; Tumour Biol. 1999, vol. 20, No. 3, 1 page (abstract).

Springer G.F., Immunoreactive T and Tn epitopes in cancer diagnosis, prognosis, and immunotherapy, J. Mol. Med. 1997, vol. 75, pp. 594-602.

Tockman, M.S., et al., Considerations in Bringing a Cancer Biomarker to Clinical Application, Cancer Res., 1998, (Suppl), vol. 52, pp. 2711s-2718.

Buskens, C., et al., Adenocarcinomas of the Gastro-Esophageal Junction: A Comparative Study of the Gastric Cardia and the Esophagus with Respect to Cyclooxygenase-2 Expression, Digestive Disease Week Abstracts and Itinerary Planner, 2003, abstract No. 850.

Glinsky, V.V., et al., The Role of Thomsen-Friedenreich Antigen in Adhesion of Human Breast and Prostate Cancer Cells to the Endothelium, Cancer Research 61, Jun. 15, 2001, pp. 4851-4857.

Springer, F.G., et al., Proposed Molecular Basis of Murine Tumor Cell-Hepatocyte Interaction, The Journal of Biological Chemistry, May 10, 1983, vol. 258, No. 9, pp. 5702-5706.

(Continued)

*Primary Examiner* — Brad Duffy
(74) *Attorney, Agent, or Firm* — Hodgson Russ LLP

(57) ABSTRACT

Provided are humanized monoclonal antibodies (mAbs) or fragments thereof that bind with specificity to the Thomsen-Friedenreich (TF) human tumor antigen. Three distinct variable heavy and three variable light chains are provided, and can be combined to make a total of twenty-five distinct heavy and light chain combinations. Methods of using the mAbs and fragments thereof for cancer therapy and diagnostic imaging are provided, as are methods for making the mAbs and fragments thereof. In vitro cell cultures that express the mAbs and fragments thereof, and kits are also provided.

12 Claims, 18 Drawing Sheets
(13 of 18 Drawing Sheet(s) Filed in Color)
Specification includes a Sequence Listing.

(56) References Cited

OTHER PUBLICATIONS

Khaldoyanidi, S.K., et al., MDA-MB-435 Human Breast Carcinoma Cell Homo- and Heterotypic Adhesion under Flow Conditions is Mediated in Part by Thomsen-Friedenreich Antigen-Galectin-3 Interactions, The Journal of Biological Chemistry, Feb. 7, 2003, vol. 278, No. 6, pp. 4127-4134.

Landon, L.A., et al., Combinatorial Evolution of High-Affinity Peptides that Bind to the Thomsen-Friedenreich Carcinoma Antigen, Journal of Protein Chemistry, Feb. 2003, vol. 22, No. 2, pp. 193-204.

Gura, T., Systems for Identifying New Drugs are Often Faulty, Science, 1997, vol. 278, pp. 1041-1042.

Freshney, R.I., Culture of Animal Cells, A Manual of Basic Technique, Alan R. Liss, Inc., 1983, New York, p. 4.

Roitt, I.M., et al., Immunology, Third Edition, Mosby, London England, 1993, p. 1.7.

Canevari, S., et al., Immunoconjugates: lessons from animal models, Annals of Oncology, 1994, vol. 5, pp. 698-701.

Harris, W.J. and Emery, S., Therapeutic antibodies—the coming of age, TIBTECH, Feb. 1993, vol. 11, pp. 42-44.

White, C.A., et al., Antibody-Targeted, Immunotherapy for Treatment of Malignancy, Ann. Rev. Med., 2001, vol. 52, pp. 125-145.

Dermer, G.B., Another Anniversary for the War on Cancer, Biotechnology, Mar. 12, 1994, vol. 12, p. 320.

Osband, M.E. and Ross, S., Problems in the investigational study and clinical use of cancer immunotherapy, Immunol. Today, 1990, vol. 11, No. 6, pp. 193-195.

Dippold, W., et al., The Role of the Thomsen-Friedenreich Antigen as a Tumor-Associated Molecule, Environmental Health Perspectives, 1990, vol. 88, pp. 255-257.

Heimburg, J., et al., Inhibition of Spontaneous Breast Cancer Metastasis by Anti-Thomsen-Friedenreich Antigen Monoclonal Antibody JAA-F11, Neoplasia, 2006, vol. 8, No. 11, pp. 939-948.

Ferguson et al., Preclinical studies with JAA-F11 anti-Thomsen-Friedenreich monoclonal antibody for human breast cancer, Future Oncology, vol. 10, pp. 385-399 2014.

\* cited by examiner

Figure 1

```
                      FR1                                            CDR1                      FR2                           CDR2
Kabat #   1           5           10          15          20          25          30          35          40          45          50 a  55 mJAAF11   EVQLLESGAELAKPGASVKMSCKA SGYTFTTYWMH WVKQRPGQGLEWIG FISPNTDYTEYNQKFRD
H1        EVQLVESGAEVKKPGASVKVSCKA SGYTFTTYWMH WVRQAPGQGLEWMG FISPNTDYT
          EYNQKFRD
H2        EVQLLESGAELKKPGASVKVSCKA SGYTFTTYWMH WVRQAPGQGLEWMG FISPNTDYTEYNQKFRD
H3        EVQLVESGAEVKKPGASVKVSCKA SGYTFTTYWMH WVKQAPGQGLEWIG FISPNTDYTEYNQKFRD

FR3                                   CDR3                   FR4
Kabat #   60    65    70    75    80  a b c 83  85            90          95    100a  105    110 113 mJAAF11   KATLTADKSSTTAYMQLSSLTSEDSAVYYCA RSFIGYNFDFWGQGT TLTVSS
H1        RVTMTADTSISTAYMELSRLRSDDTAVYYCA RSFIGYNFDFWGQGT LVTVSS
H2        RVTLTADKSSSTAYMELSSLTSEDTAVYYCA RSFIGYNFDFWGQGT TVTVSS
H3        KATMTADTSISTAYMELSRLRSDDTAVYYCA RSFIGYNFDFWGQGT TLTVSS
```

Figure 1

| Kabat# | FR1 | CDR1 | FR2 | CDR2 |
|---|---|---|---|---|
|  | 1      5     10     15     20 | 25   a bce 30 | 35      40      45 | 50     55 |
| JAAF11 | ELVMTQTPLSLPVNLGDQASIS | CRSSQTIVYSNGNTYLEW | YLQKPGQSPKLLIY | KVSNRFSGVPD |
| L1 | DVVMTQSPLSLPVTLGQPASIS | CRSSQTIVYSNGNTYLEW | FQQRPGQSPRLLIY | KVSNRFSGVPD |
| L2 | DIVMTQTPLSLPVTLGQPASIS | CRSSQTIVYSNGNTYLEW | FQQRPGQSPRLLIY | KVSNRFSGVPD |
| L3 | DVVMTQSPLSLPVTLGQPASIS | CRSSQTIVYSNGNTYLEW | YLQRPGQSPRLLIY | KVSNRFSGVPD |

| Kabat# | FR3 | CDR3 | FR4 |
|---|---|---|---|
|  | 61  65     70     75     80     85     90 | 95     100 | a |
| JAAF11 | RFSGSGSGTDFTLKISRVEADDLGVYY | CFQGSHVPFTFGSG | TKLEIK |
| L1 | RFSGSGSGTDFTLKISRVEAEDVGVYY | CFQGSHVPFTFGSG | TKLEIK |
| L2 | RFSGSGSGTDFTLKISRVEAEDVGVYY | CFQGSHVPFTFGSG | TKLEIK |
| L3 | RFSGSGSGTDFTLKISRVEAEDVGVYY | CFQGSHVPFTFGSG | TKLEIK |

Figure 2

A
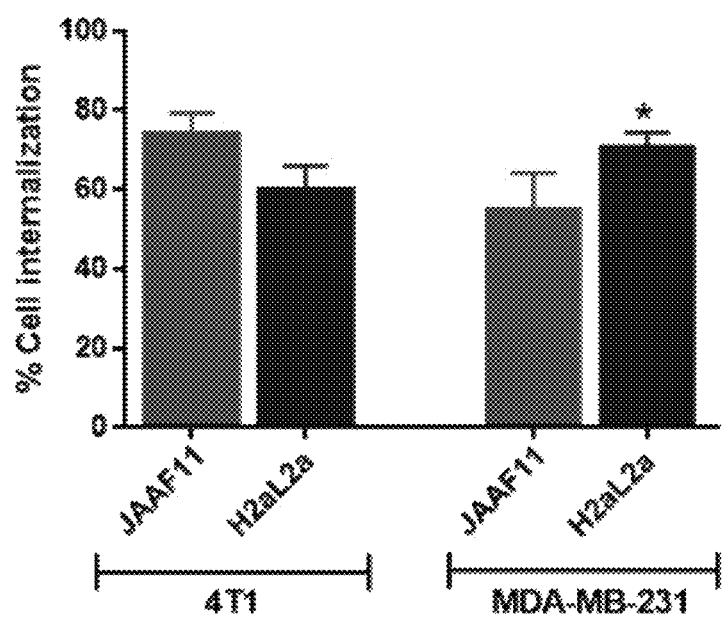
B
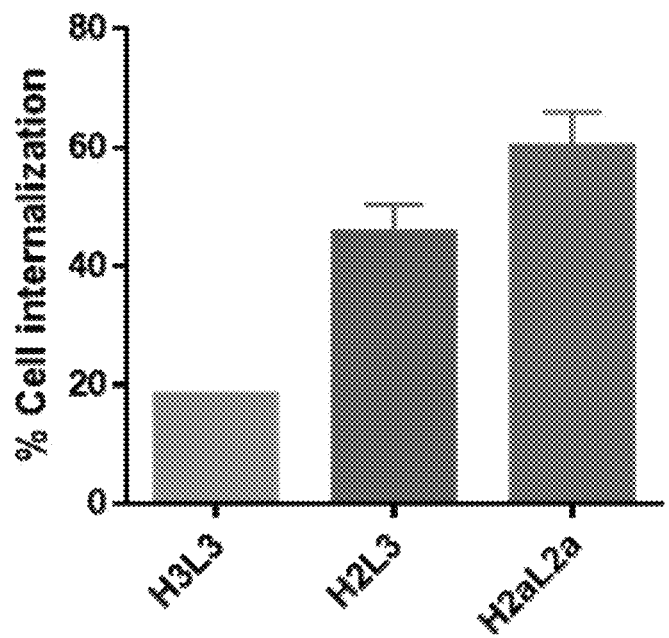
Figure 13

C

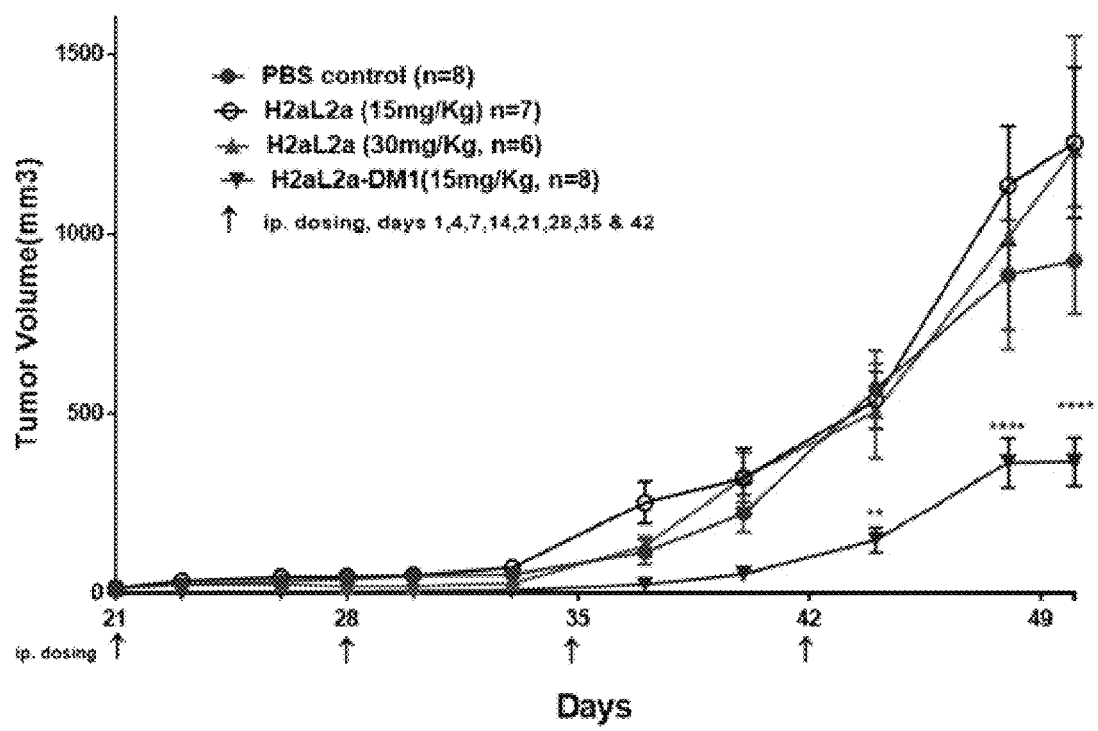
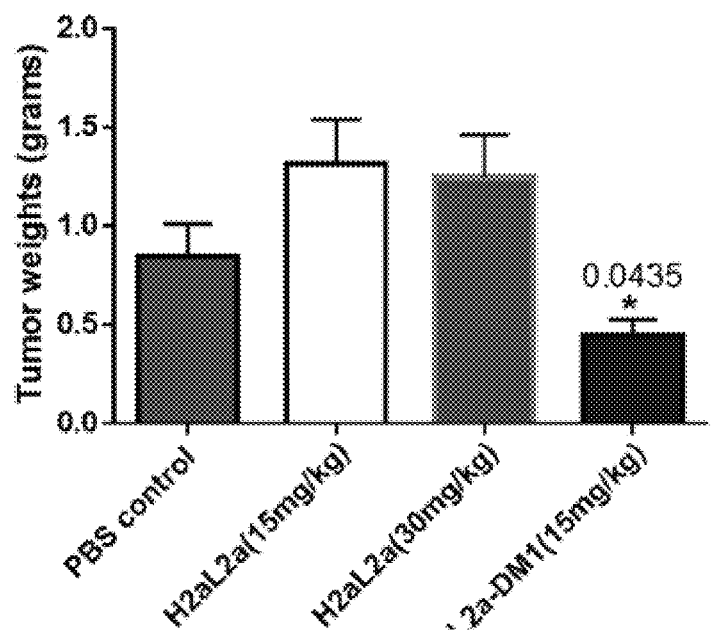
Figure 15

HUMANIZED ANTI-TF-ANTIGEN ANTIBODIES

CROSS REFERENCE TO RELATED APPLICATIONS

This application is a continuation of U.S. patent application Ser. No. 15/296,411, filed Oct. 18, 2016, now U.S. Pat. No. 10,023,651, issued on Jul. 17, 2018, which is a continuation-in-part of International Patent Application No. PCT/US2015/026595, filed Apr. 20, 2015, which claims priority to U.S. Provisional Patent Application No. 61/981,240, filed Apr. 18, 2014, the disclosures of each of which are incorporated herein by reference.

STATEMENT REGARDING FEDERALLY SPONSORED RESEARCH

This invention was made with government support under Grant No. A1049210 awarded by National Institutes of Health. The government has certain rights in the invention.

FIELD

The present disclosure relates generally to humanized antibodies that recognize the Thomsen-Friedenreich (TF) human tumor antigen, and methods for using the monoclonal antibodies.

BACKGROUND

During carcinogenesis, alterations occur in the biosynthesis of carbohydrate structures on the cell surface, and several different carbohydrates linked either to proteins or to lipids have been recognized to be tumor-associated antigens. Thomsen-Friedenreich (TF) disaccharide (Galβ1-3GalNAcα) is typically found O-linked to serine or threonine residues. TF-Ag (also known as T antigen) has been associated with several human carcinomas, including those found in the pancreas, colon, and breast, and on this basis has been referred to as a pan-carcinoma marker. TF-Ag is concealed from the immune system in normal adult tissues by extension with larger glycan chains. In cancer, the cellular glycosylation machinery may be disrupted leading to truncation of these chains and exposure of the TF antigen. New monoclonal antibodies and antibody fragments thereof which can target TF-Ag are desirable, and are provided by the present disclosure.

SUMMARY

The present disclosure comprises in various embodiments compositions and methods for therapy of TF+ cancers. In embodiments, the disclosure comprises partially humanized monoclonal antibodies (mAbs) or fragments thereof that bind with specificity to TF-Ag. The mAb or fragment thereof comprises a heavy chain and a light chain, wherein the heavy chain comprises a sequence selected from the group consisting of:

(SEQ ID NO: 7)
EVQLVESGAEVKKPGASVKVSCKASGYTFTTYWMHWVRQAPGQGLEWMGF

ISPNTDYTEYNQKFRDRVTMTADTSISTAYMELSRLRSDDTAVYYCARSF

IGYNFDFWGQGTLVTVSS (H1);

(SEQ ID NO: 8)
EVQLLESGAELKKPGASVKVSCKASGYTFTTYWMHWVRQAPGQGLEWMGF

ISPNTDYTEYNQKFRDRVTLTADKSSSTAYMELSSLTSEDTAVYYCARSF

IGYNFDFWGQGTTVTVSS (H2);
and (SEQ ID NO: 9)
EVQLVESGAEVKKPGASVKVSCKASGYTFTTYWMHWVKQAPGQGLEWIGF

ISPNTDYTEYNQKFRDKATMTADTSISTAYMELSRLRSDDTAVYYCARSF

IGYNFDFWGQGTTLTVSS (H3), and combinations thereof.
The light chain comprises a sequence selected from the group consisting of:

(SEQ ID NO: 10)
DVVMTQSPLSLPVTLGQPASISCRSSQTIVYSNGNTYLEWFQQRPGQSPR

LLIYKVSNRFSGVPDRFSGSGSGTDFTLKISRVEAEDVGVYYCFQGSHVP

FTFGSGTKLEIK (L1);

(SEQ ID NO: 11)
L2DIVMTQTPLSLPVTLGQPASISRSSQTIVYSNGNTYLEWFQQRPGQSP

RLLIYKVSNRFSGVPDRFSGSGSGTDFTLKISRVEAEDVGVYYCFQGSHV

PFTFGSG TKLEIK (L2);
and (SEQ ID NO: 12)
DVVMTQSPLSLPVTLGQPASISCRSSQTIVYSNGNTYLEWYLQRPGQSPR

LLIYKVSNRFSGVPDRFSGSGSGTDFTLKISRVEAEDVGVYYCFQGSHVP

FTFGSGTKLEIK (L3);

and combinations thereof.
Additional versions H2, H3, L2 and L3 were made and tested. These include the following:

Heavy variable region H2a:
(SEQ ID NO: 13)
QVQLVQSGAEVKKPGSSVKVSCKASGYTFTTYWMHWVRQAPGQGLEWMGF

ISPNTDYTEYNQKFRDRVTITADKSTSTAYMELSSLRSEDTAVYYCARSF

IGYNFDFWGQGTTVTVS

Heavy variable region H3a:
(SEQ ID NO: 14)
EGQLLESGAELAKPGASVKMSCKASGYTFTTYWMHWVKKRPGQGLEWIGF

ISPNTDYTEYNQKFRDKATLTADKSSTTAYMQLSSLTSDDSAVYYCARSF

IGYNFDFWGQGTTLTVSS

Light variable region L2a:
(SEQ ID NO: 15)
DIVMTQSPLSLPVTPGEPASISCRSSQTIVYSNGNTYLEWYLQKPGQSPQ

LLIYKVSNRFSGVPDRFSGSGSGTDFTLKISRVEAEDVGVYYCFQGSHVP

FTFGSGTKVDIK

Light variable region L3a:
(SEQ ID NO: 16)
ELVMTQTPLSLPVNLGDQASISCRSSQTIVYSNGNTYLEWYLQKPGQSPK

LLIYKVSNRFSGVPDRFSGSGSGTDFTLKISRVEADDLGVYYCFQGSHVP

FTFGSGTKLEIK.

Combinations of heavy and variable chains included in this disclosure are: H1-L1; H1-L2; H1-L2a; H1-L3; H1-L3a; H2-L1; H2-L2; H2-L2a; H2-L3; H2-L3a; H3-L1; H3-L2; H3-L2a; H3-L3; H3-L3a; H2a-L1; H2a-L2; H2a-L2a; H2a-L3; H2a-L3a; H3a-L1; H3a-L2; H3a-L2a; H3a-L3; and H3a-L3a.

In embodiments, the mAb comprises a human IgG constant region. In embodiments, the mAb or the TF-Ag binding fragment thereof is conjugated to an agent selected from the group consisting of chemotherapeutic drugs, toxins and radioactive isotopes.

In another aspect, the disclosure comprises a method for prophylaxis and/or therapy of cancer in an individual, wherein the cancer comprises cancer cells expressing TF-Ag. The method comprises administering to the individual one or more mAbs or the fragments as described above, wherein the growth, or survival, or metastasis, or a combination thereof, of the cancer cells in the individual is inhibited subsequent to the administration.

In another aspect, pharmaceutical compositions comprising the partially humanized mAb or fragment thereof are provided.

In another aspect the disclosure provides an in vitro cell culture, wherein cells in the cell culture express the partially humanized mAb or fragments thereof.

In another aspect, the disclosure provides polynucleotide sequences encoding the mAbs and TF-Ag binding fragments thereof, expression vectors comprising such polynucleotides, and in vitro cell cultures comprising such expression vectors. In embodiments, the mAb or TF-Ag binding fragment thereof is encoded by more than one expression vector.

In embodiments, methods of making the mAbs and TF-Ag binding fragments thereof are provided, and generally comprise expressing the mAbs or TF-Ag binding fragments, or combinations thereof in an in vitro cell culture, and separating the mAbs or TF-Ag binding fragments, or combinations thereof, from the cell culture.

Kits comprising the mAbs and TF-Ag binding fragments thereof are also provided.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 provides the amino acid sequence alignments of JAA-F11 heavy variable and the three VH variants (H1, H2, and H3) regions that are included in this disclosure. Bold indicates identical amino acids between JAA-F11 and the designed, humanized H chains; bold and shaded amino acids indicate differences among the designed humanized chains and mouse JAA-F11. Alanine at position 72 shown in bold and italicized is a mouse residue that was retained to avoid steric clashes. The complementarity determining regions (CDRs) are italicized. Numbering is according to the Kabat system. The mJAAF11 sequence is SEQ ID NO:17. The H1 sequence is SEQ ID NO:7; the H2 sequence is SEQ ID NO:8; the H3 sequence is SEQ ID NO:9.

FIG. 2 depicts amino acid sequence alignments of mJAA-F11 light variable (JAA-F11VH) and three VL variants (L1, L2, and L3) regions. Bold indicates mouse amino acids or amino acids identical to the mouse sequence, bold and shaded amino acids are differences among the designed humanized JAA-F11 variants and mouse JAA-F11. Leucine at position 51, shown as bold and italicized is a mouse residue that was retained to avoid steric clashes. The mJAAF11 sequence is SEQ ID NO:17. The L1 sequence is SEQ ID NO:10; the L2 sequence is SEQ ID NO:11; the L3 sequence is SEQ ID NO:12.

FIG. 15. Efficacy of H2aL2a conjugated DM1 in a SCID mouse xenograft triple negative breast tumor model. A) 10×106 MDA-MB 231 cells were injected into female SCID mice intra-mammary gland on day 0. Antibody treatments began on day 1 and included i.p. injection of PBS, naked hJAA-F11 (15 mg/Kg), hJAA-F11 (30 mg/Kg), hJAA-F11-DM1 (15 mg/Kg). Arrows indicate injection days (n=8 mice per group). Tumor growth was monitored for 50 days. ANOVA Analysis of PBS versus hJAA-F11-DM1,  p=0.0072, **p<0.0001. B) Bar graphs representing the mean tumor weights±S.E in the control and antibody treatment groups. Tumors were removed and weighed on day 50. * Unpaired t test was used to analyze the PBS control versus hJAA-F11-DM1. hJAA-F11-DM1 significantly reduces mean tumor weight at day 50.

FIG. 16. In vitro metastasis model showing mouse JAA-F11 and hJAA-F11 H2aL2a inhibition of tumor cell adhesion. The adhesion of MDA-MB-231 cells to primary human pulmonary microvascular endothelial cells (HPMEC, ScienCell Research Laboratories, Carlsbad, Calif.) was studied in an in vitro parallel plate laminar flow chamber with control immunoglobulin or with mouse JAA-F11 or H2aL2a.

DETAILED DESCRIPTION

Figure 3:
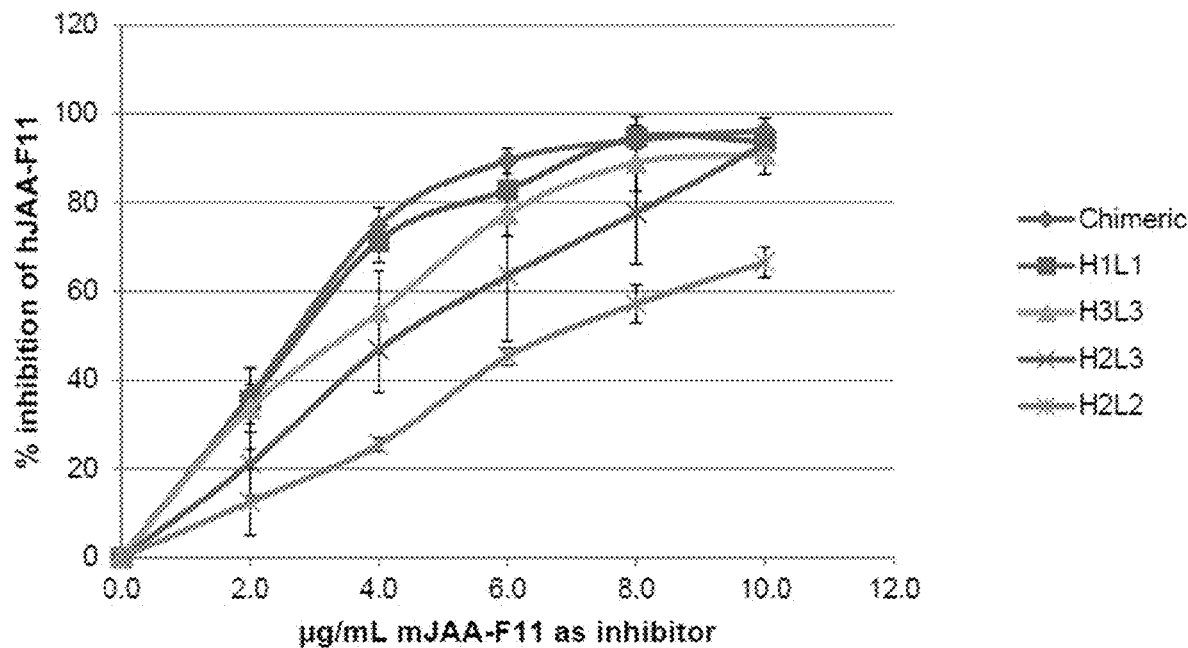
FIG. 3. Determination of relative affinity using mJAA-F11 inhibition by ELISA to assess the binding of each hJAA-F11 and chimeric antibody to TF-Ag-BSA. Error bars represent ±1 standard error.

The present disclosure comprises distinct humanized monoclonal antibodies (mAbs) and fragments thereof which specifically recognize TF-Ag, methods of making the mAbs, and methods of using the mAbs for prophylaxis and/or therapeutic purposes, and for diagnostic imaging. The amino acid sequences of the mAbs provided by this disclosure were developed using a novel approach to change the amino acid sequences in the mAb produced by a hybridoma deposited under ATCC Catalog number CRL-2381, such that the framework regions of the mAbs incorporate both murine and human immunoglobulin (Ig) sequences in a guided way that maintains specificity and reduces immunogenicity. The hybridoma produces a mAb known as JAA-F11. Changes introduced into JAA-F11 sequence in the context of the murine framework regions result in an ensemble of three distinct heavy and three distinct light variable chains that can be combined to produce twenty five distinct mAbs that are suitable for combating any of variety of cancers that comprise cancer cells that express TF-Ag. Further, the mAbs have desirable characteristics that render them particularly suited for preferentially inducing distinct anti-cancer mechanisms in an individual. For example, depending on the choice of heavy and light chain, the disclosure includes providing for stimulating enhanced antibody-dependent cytotoxicity, or complement dependent cytotoxicity, or internalization of the mAb.

Embodiments of the disclosure include CDR sequences from the JAA-F11 mAb. These are: VH chain: CDR1: SGYTFTTYWMH; (SEQ ID NO:1); CDR2: FISPNTDYTEYNQKFRD; (SEQ ID NO:2); CDR3: RSFIGYNFDFWGQGT; (SEQ ID NO:3); and VL chain: CDR1: CRSSQTIVYSNGNTYLEW; (SEQ ID NO:4); CDR2: KVSNRFSGVPD; (SEQ ID NO:5); and CDR3: CFQGSHVPFTGSG; (SEQ ID NO:6).

The CDR sequences are placed in the context of modified framework sequences. As a consequence, the mAbs and TF-Ag binding fragments thereof comprise a heavy chain selected from:

```
                                          (SEQ ID NO: 7)
H1-EVQLVESGAEVKKPGASVKVSCKASGYTFTTYWMHWVRQAPGQGLEW

MGFISPNTDYTEYNQKFRDRVTMTADTSISTAYMELSRLRSDDTAVYYCA

RSFIGYNFDFWGQGTLVTVSS;
```

(SEQ ID NO: 8)
H2-EVQLLESGAELKKPGASVKVSCKASGYTFTTYWMHWVRQAPGQGLEW

MGFISPNTDYTEYNQKFRDRVTLTADKSSSTAYMELSSLTSEDTAVYYCA

RSFIGYNFDWGQGTTVTVSS;

(SEQ ID NO: 9)
H3-EVQLVESGAEVKKPGASVKVSCKASGYTFTTYWMHWVKQAPGQGLEW

IGFISPNTDYTEYNQKFRDKATMTADTSISTAYMELSRLRSDDTAVYYCA

RSFIGYNFDWGQGTTLTVSS and combinations thereof;
and a light chain selected from the group consisting of:

(SEQ ID NO: 10)
L1-DVVMTQSPLSLPVTLGQPASIS CRSSQTIVYSNGNTYLEW FQQRP

GQSPRLLIY KVSNRFSGVPDRFSGSGSGTDFTLKISRVEAEDVGVYY C

FQGSHVPFTFGSGTKLEIK;

(SEQ ID NO: 11)
L2-DIVMTQTPLSLPVTLGQPASIS CRSSQTIVYSNGNTYLEW FQQRP

GQSPRLLIY KVSNRFSGVPDRFSGSGSGTDFTLKISRVEAEDVGVYY C

FQGSHVPFTFGSGTKLEIK;

(SEQ ID NO: 12)
L3-DVVMTQSPLSLPVTLGQPASIS CRSSQTIVYSNGNTYLEWYLQRPG

QSPRLLIY KVSNRFSGVPDRFSGSGSGTDFTLKISRVEAEDVGVYYCFQ

GSHVPFTFGSG TKLEIK and combinations thereof.

In addition to the foregoing sequences, the following heavy and light chains were made and tested in certain combinations:

Heavy variable region H2a:
(SEQ ID NO: 13)
QVQLVQSGAEVKKPGSSVKVSCKASGYTFTTYWMHWVRQAPGQGLEWMGF

ISPNTDYTEYNQKFRDRVTITADKSTSTAYMELSSLRSEDTAVYYCARSF

IGYNFDWGQGTTVTVS

Heavy variable region H3a:
(SEQ ID NO: 14)
EGQLLESGAELAKPGASVKMSCKASGYTFTTYWMHWVKKRPGQGLEWIGF

ISPNTDYTEYNQKFRDKATLTADKSSTTAYMQLSSLTSDDSAVYYCARSF

IGYNFDWGQGTTLTVSS

Light variable region L2a:
(SEQ ID NO: 15)
DIVMTQSPLSLPVTPGEPASISCRSSQTIVYSNGNTYLEWYLQKPGQSPQ

LLIYKVSNRFSGVPDRFSGSGSGTDFTLKISRVEAEDVGVYYCFQGSHVP

FTFGSGTKVDIK

Light variable region L3a:
(SEQ ID NO: 16)
ELVMTQTPLSLPVNLGDQASISCRSSQTIVYSNGNTYLEWYLQKPGQSPK

LLIYKVSNRFSGVPDRFSGSGSGTDFTLKISRVEADDLGVYYCFQGSHVP

FTFGSGTKLEIK.

The disclosure encompasses mAbs and TF-Ag binding fragments thereof comprising amino acid sequences that comprise or consist of the foregoing sequences. In embodiments, the disclosure comprises mAbs and TF-Ag binding fragments thereof, wherein the framework and CDR sequences consist of SEQ ID NO:7, SEQ ID NO:8, SEQ ID NO:9, SEQ ID NO:10, SEQ ID NO:11, SEQ ID NO:12, SEQ NO:13, SEQ ID NO:14, SEQ ID NO:15, and SEQ ID NO:16.

Thus, the following 25 Heavy and Light chain combinations are encompassed by this disclosure: H1-L1; H1-L2; H1-L2a; H1-L3; H1-L3a; H2-L1; H2-L2; H2-L2a; H2-L3; H2-L3a; H3-L1; H3-L2; H3-L2a; H3-L3; H3-L3a; H2a-L1; H2a-L2; H2a-L2a; H2a-L3; H2a-L3a; H3a-L1; H3a-L2; H3a-L2a; H3a-L3; and H3a-L3a. In embodiments, the disclosure includes mAbs and TF-Ag binding fragments thereof comprising a combination of H1L1, H2L2, H3L3, H2L3, H2a and L2a, and H3a and L3a. In this disclosure, in addition to the results for combinations of H and L chains as described below, H2a-L2a and H3aL3a were made and tested, and the results for these two combinations were similar to those reported for H2-L2 and H3-L3, respectively. The H2a-L2a and H3a-L3a combinations were made as a result of subcloning procedures, allowing for selection of additional subclones with further enhanced binding characteristics for TF-Ag, as determined by the highest reactivity in enzyme immunoassays (EIA). Of these, the best for internalization are H2L2 and H2aL2a, while the best for ADCC are H2L2, H2aL2a, H3L3 and H3aL3a.

Representative VH and VL sequences are further described by way of FIGS. 1 and 2. In particular, FIG. 1 provides the amino acid sequence alignments of JAA-F11 heavy variable and the three VH variants (H1, H2, and H3) regions that are included in this disclosure. Bold indicates identical amino acids between JAA-F11 and the designed, humanized H chains; bold and shaded amino acids indicate differences among the designed humanized chains and mouse JAA-F11. Alanine at position 72 shown in bold and italicized is a mouse residue that was retained to avoid steric clashes. The CDRs are italicized. Numbering is according to the Kabat system. It will thus be recognized that, while the mAbs described herein are referred to as "humanized" they do comprise certain murine residues, and thus can be considered partially humanized. It will be recognized that in embodiments the amino acid sequences provided herein are present in the context of intact antibodies, and as such can comprise additional amino acids on their N- and C-termini. For example, in certain embodiments, the sequences associated with the SEQ ID numbers of this disclosure can comprise one or more Serines at their C-terminal sequences. In one non-limiting example, the H2a sequence has an additional Serine.

FIG. 2 depicts amino acid sequence alignments of mJAA-F11 light variable (JAA-F11VH) and three VL variants (L1, L2, and L3) regions. Bold indicates mouse amino acids or amino acids identical to the mouse sequence, bold and shaded amino acids are differences among the designed humanized JAA-F11 variants and mouse JAA-F11. Leucine at position 51, shown as bold and italicized is a mouse residue that was retained to avoid steric clashes. It will be apparent from FIGS. 1 and 2 that the presently provided, humanized H and L chains comprise differences from the JAA-F11 mouse antibody and differences among themselves, but certain murine amino acids have been retained to maintain the specificity of the humanized mAbs.

Fragments of the humanized mAbs described herein are also included in the invention. Examples of suitable antibody fragments include Fab, Fab', F(ab')2, ScFv and FIT fragments. Various techniques have been developed for the production of antibody fragments and are included in the scope of this disclosure. In embodiments, the mAbs or fragments thereof are produced host cells by way of recombinant expression vectors. The present disclosure includes all polynucleotide sequences encoding the amino acid sequences described herein, expression vectors comprising such polynucleotide sequences, and in vitro cell cultures comprising such expression vectors. In embodiments, the cell cultures are eukaryotic cells. In embodiments, the cell cultures are mammalian cells. In embodiments, the cells are CHO cells. Kits comprising the mAbs and/or TF-Ag binding fragments thereof, and/or cell cultures expressing the mAbs and/or TF-Ag binding fragments thereof, are provided by this disclosure. In general, the kits comprise one or more sealed containers that contain the mAbs and/or TF-Ag binding fragments thereof, or cells expressing them. Instructions for using the mAbs and/or TF-Ag binding fragments for therapeutic and/or imaging purposes can be included in the kits.

In embodiments, the disclosure includes a method of making the mAbs or TF-Ag binding fragments thereof, comprising culturing cells comprising an expression vector or other polynucleotide sequence encoding the mAbs or TF-Ag binding fragments thereof, allowing expression of the mAbs or TF-Ag binding fragments thereof, and separating the mAbs or TF-Ag binding fragments thereof from the cell culture. Nucleotide sequences encoding the mAbs or TF-Ag binding fragments thereof can be expressed using any suitable expression vector, many of which are known in the art and/or are commercially available. In one embodiment, the heavy and light chains are expressed on a single expression vector, such as a plasmid. In another embodiment, the heavy and light chains are expressed on distinct plasmids in the same cell, after which the expressed heavy and light chains form the conventional mAb architecture. The mAbs or TF-Ag binding fragments thereof can be isolated and/or purified using conventional techniques, given the benefit of the present disclosure.

In another aspect, the disclosure provides a method of inhibiting the growth of cancer cells in an individual, and/or inhibiting metastasis of cancer cells in an individual, which cancer cells express TF-Ag molecules. The method comprises administering to the individual a therapeutic amount of the humanized mAbs and/or fragments thereof, wherein the administration inhibits the growth and/or inhibits the metastasis of the TF-Ag expressing cancer cells. In embodiments, practicing the method of the invention reduced the volume of a tumor, and/or reduces the formation of metastatic foci, or secondary tumors. In embodiments, the method is provided for an individual in need thereof. In embodiments, the individual in need has been diagnosed with, is suspected of having, or is at risk for developing or having a recurrence of cancer. In embodiments, a therapeutically effective amount of a mAb or TF-Ag binding fragment thereof is used. The term "therapeutically effective" as used herein means that the amount of the mAb or TF-Ag binding fragment thereof administered is of sufficient quantity to inhibit the growth, survival and/or metastasis of TF+ cancer cells.

In various embodiments, the humanized mAbs and/or fragments thereof can be conjugated to a chemotherapeutic agent to enable localization of the chemotherapeutic agent to cancer cells via binding to cells expressing TF-Ag. Chemotherapeutic agents useful in the generation of such antibody conjugates include enzymatically active toxins and fragments thereof. Suitable enzymatically active toxins include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. The chemotherapeutic agents can be covalently attached to the mAb or TF-Ag binding fragment thereof by any suitable chemical conjugation approach. In embodiments, the chemotherapeutic agent can comprise a segment of a fusion protein with the mAb or TF-Ag binding fragment.

In another aspect the disclosure provides a method for identifying in an individual metastatic foci, tumors, or combinations thereof, wherein the metastatic foci or tumors comprise cells expressing TF-Ag. The method comprises the steps of administering to the individual humanized mAbs and/or fragments thereof, wherein the humanized mAbs and/or fragments thereof have been conjugated to a detectable label, and detecting the detectable label to identify metastatic foci, tumors, or combinations thereof. Thus, the humanized mAbs and/or fragments thereof may be conjugated to a detectable label, such as a radioactive agent. A variety of radioactive isotopes are available for conjugating to JAA-F11 mAbs such that cells to which the JAA-F11 mAbs bind may be imaged or selectively destroyed. For selective destruction of cells expressing TF-Ag, the JAA-F11 mAbs may be conjugated to a highly radioactive atom, such as In111, At211, I131, I125, Y90, Re186, Re188, Sm153, Bi212, P32, Pb212 and radioactive isotopes of Lu.

When the humanized mAbs and/or fragments thereof are used for identifying cells expressing TF-Ag in metastatic foci or in tumors, they may comprise a radioactive atom for scintigraphic studies, for example Tc99m (metastable technetium-99), I123, or a spin label for nuclear magnetic resonance (NMR) imaging (also known as magnetic resonance imaging, or "MRI"), such as I123, I131, I124, F19, C13, N15, O17 or Gadlinium (III) or Manganese (II).

Labeled humanized mAbs and/or fragments thereof can be injected into patients diagnosed with or suspected of having a metastatic disease to identify metastatic foci and/or tumors. Information from such imaging can be used for diagnosing or staging of the disease status of the patient. The label used can be selected in accordance with the imaging system to be used. For example, Indium111, Technetium99 or Iodine131 can be used for planar scans or single photon emission computed tomography (SPECT). Positron emitting labels such as Fluorine19 Iodine 123 and Iodine 124 can be used in positron emission tomography. Paramagnetic ions such as Gadlinium (III) or Manganese (II) can used in magnetic resonance imaging (MRI). Localization of the label within a particular tissue of the individual permits localization of metastatic foci or tumors which comprise cells expressing TF-Ag. A concentration of label at a particular location greater than background permits identification of the presence of metastasized cells. In a preferred embodiment, after administration of labeled humanized mAbs and/or fragments thereof, a suitable period of time is allowed to pass such that unbound humanized mAbs and/or fragments thereof are cleared from the individual such that background label is greatly reduced.

Therapeutic formulations comprising conjugated or unconjugated humanized mAbs and/or fragments thereof may be prepared by mixing with pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The humanized mAbs and/or fragments thereof may be combined with other chemotherapeutic agents in pharmaceutical compositions.

The humanized mAbs and/or TF-binding fragments thereof may be administered by any suitable means, including parenteral, subcutaneous, intraperitoneal, intrapulmonary, and intranasal. Parenteral infusions include intramuscular, intravenous, intraarterial, intraperitoneal, intralymphatic or subcutaneous administration. In addition, the humanized mAbs and/or fragments thereof may suitably be administered by pulse infusion, e.g., with declining doses of the antibody. Preferably, the dosing is given by injections, most preferably intravenous or subcutaneous injections, depending in part on whether the administration is brief or chronic. In certain embodiments, the humanized mAbs and/or fragments thereof are administered to an individual diagnosed with or suspected of having breast, colon, prostate, ovarian, bladder or other TF Ag+ cancers to inhibit metastasis or to inhibit the growth of the cancer cells.

Other compounds, such as chemotherapeutic agents, immunosuppressive agents and/or cytokines can also be administered. The combined administration can include co-administration, using separate formulations or a single pharmaceutical formulation, and can also include consecutive administration in either order, wherein preferably there is a time period while both (or all) active agents simultaneously exert their biological activities.

The humanized mAbs and/or fragments thereof may be administered to a human or other animal in accordance with the aforementioned methods of treatment in an amount sufficient to inhibit metastasis and/or growth of cells expressing TF-Ag. It will be recognized by one of skill in the art that the form and character of the pharmaceutically acceptable carrier or diluent is dictated by the amount of active ingredient with which it is to be combined, the route of administration and other well-known variables, such as the size of the individual and the stage of the disease.

Example 1

The following Example describes making and using humanized mAbs of this disclosure, and physical and functional properties of the mAbs.

Design and Construction of Humanized JAA-F11

After the sequences of the mouse JAA-F11 variable regions were verified, the CDRs were defined so as to maintain specificity and affinity for TF-Ag. The inclusive CDRs were defined according to both Kabat et al [139] and Chothia et al [141] based on sequence and structural variability, respectively. Two amino acids are considered to contact one another in a protein structure if both contain a pair of atoms separated by 6 Å or less [138]. X-ray crystallography and computational carbohydrate threading studies on mouse JAA-F11 [142] identified amino acid residues within 5-6 Å from the binding site. These amino acids as well as two cysteine residues at position L23 and L88 of the light chain that are important for conformational structure were included in the final inclusive definition of the CDRs used in JAA-F11 humanization.

Selection of Human Frameworks

Three different approaches were applied to select the human acceptor antibody framework for the heavy and light JAAF11 variable region chains. Three variants of the heavy chain (H1, H2, H3) and 3 variants of the light chain (L1, L2, L3) were designed. Any of the 3 heavy chains (VH) can pair with any of the 3 light chains (VL) to create a total of 9 possible hJAA-F11 VH/VL combination variants.

To create these variants, a BLAST search was performed separately comparing the VH and VL sequence of the mJAA-F11 (mouse antibody) against human immunoglobulin sequences. The top 10 most homologous human VH and VL sequences were aligned with the corresponding variable regions of mJAA-F11 using the Seaview Sequence Alignment program.

For the first variants, H1 and L1, the amino acid sequence of the framework regions were chosen based on the amino acid most often seen at each position in the top 10 most homologous human IgG variable sequences. For variants H2 and L2, the amino acid sequence of the framework regions were chosen as follows: if the amino acid in any of the top 10 human sequences matched the corresponding amino acid in the mouse immunoglobulin then that amino acid was chosen, in the remaining positions the amino acid most often seen in the human sequences was chosen. For the third variant, H3 and L3, the amino acid sequence of the framework region contained 3 mouse amino acids on either side of each CDR while the rest of the sequence is made up of amino acids most often seen in the top 10 human sequences.

A chimeric JAA-F11 was also constructed which consisted of the entire mouse JAA-F11 variable region attached to human constant regions. The chimeric was made to verify that the correct mouse variable regions have been cloned and sequenced and also to serve as a positive control when evaluating the humanized JAA-F11 antibodies. The chimeric is expected to maintain the same binding characteristics as the mouse JAA-F11, while having the human constant region.

Assessment of Models of hJAA-F11

The originally proposed hJAA-F11 constructs were assessed for conformational effects on the binding site. The three heavy chain variants (H1, H2, H3) had a replacement for alanine of arginine at position 72 that could potentially cause serious steric interaction with surrounding amino acids. A leucine at position 51 for the light chain variants (L1, L2, L3) was replaced with arginine which could result in steric clashes with surrounding amino acids side chains. The arginine residue was removed and replaced with the original mouse JAA-F11 framework residue, alanine 72 (VH) and leucine 51 (VL) as shown in FIGS. 1 and 2. The alignment comparisons between the mouse JAA-F11 heavy and light variable amino acid sequences and the hJAA-F11 constructs are as shown in FIGS. 1 and 2. Those skilled in the art will also recognize the distinctions in amino acid sequences presented in H2a, H3a, L2a, and L3a, as compared to the other H and L sequences.

Immunogenicity Prediction of hJAA-F11 Variants

The predicted immunogenicity using the T20 score of our humanized variants (CDR grafted) is anticipated to be very low (Table 1). T20 score is used to measure the "humanness" of monoclonal antibody variable region sequences. This scoring system was developed by Gao et al [*Monoclonal antibody humanness score and its applications*. 2013. BMC Biotechnology, 13:55], using a database of over 38,000 human antibody sequences. In this method, a protein BLAST of this database is performed and the test humanized Ab is compared against these human sequences. The humanized antibody is compared to the top 20 human Ab BLAST matches and scored for similarity to these sequences. The highest possible score is 100 (most human-like).

Validation of this method was shown when Gao et al tested this immunogenicity scoring method on more than 90 antibodies that have been used clinically in humans, and found that antibodies with T20 scores of FR & CDR sequences above 80 were not immunogenic while T20 scores for FR sequences only, which were above 85 were not immunogenic. Using the T20 values of the current hJAA-F11 variants, very low immunogenicity is expected in patients. This shows that the CDR-grafted antibodies are more human and expected to be less immunogenic than the chimeric, that the H1L1 variant is the most human of the CDR-grafted variants, and that all the hJAA-F11 variants are expected to have low immunogenicity.

TABLE 1

Assessment of immunogenicity of the hJAA-F11 constructs. * score >80 for FR and CDR sequences is not immunogenic in humans. ** score >85 for FR sequences only is not immunogenic in humans.

| JAA-F11 variants | T20-score (FR & CDR) | | T20-score (FR) | |
|---|---|---|---|---|
| | Heavy Chain | Light Chain | Heavy Chain | Light Chain |
| Chimeric | 67 | 78 | 77 | 86 |
| H1L1 | 83 | 88 | 97 | 96 |
| H2L2 | 76 | 87 | 90 | 95 |
| H3L3 | 78 | 86 | 90 | 93 |

Expression and Production of Humanized and Chimeric JAA-F11 Variants

The hJAA-F11 and chimeric VH and VL genes were cloned into two different mammalian expression vectors containing the human IgG1 heavy chain constant region (6307 pAH) and the human kappa light chain constant region (6714 pAN) respectively to produce plasmids containing complete IgG1 and kappa genes. The correct sequence and orientation of the each of cloned VH and VL regions in 6307 pAH and 6714 pAN expression vectors were verified by sequencing.

After stable co-transfection of the two vectors into CHO-K1 cells, stable clones expressing hJAA-F11 or chimeric were selected on the basis of neomycin resistance using the antibiotic G418 and the expression of chimeric or hJAA-F11. Screening of the hJAA-F11 candidates was performed using an ELISA for anti-TF-Ag antibody as using established techniques. The clones from co-transfection of each humanized JAA-F11 H/L combination variants and the chimeric JAA-F11 that showed the highest reactivity to TF-Ag were chosen for further characterizations as described herein. Humanized JAA-F11 constructs and chimeric JAA-F11 were purified from culture supernatants by protein A column chromatography individually. A chimeric antibody, as well as H1L1, H2L2, H3L3 and H2L3, H2aL3a, and H3aL3a, have been produced. Given the benefit of the present disclosure the skilled artisan can readily produce the remaining antibody H and L chain combinations that are encompassed in the present invention.

Chemical Specificity Analysis by Glycan Array

After the initial screening, the chemical specificity of the hJAA-F11 and chimeric JAA-F11 variants were determined using a glycan array by the Consortium for Functional Glycomics. These data were compared to data obtained for mouse JAA-F11. The glycan array analysis is an indirect immunofluorescent method to determine glycan binding reactivity of lectins and antibodies. An earlier glycan array was utilized to demonstrate the chemical specificity of mouse JAA-F11. This method was used to analyze the reactivity of the antibody candidates with 610 different glycans. The hJAA-F11 H1L1, H2L2, H3L3, and the chimeric antibody showed the same fine specificity of binding as the mouse antibody including the limitation of binding to the Galβ1-3GalNAc-α (TF-Ag) linked structures, and the lack of binding with α2-3 sialylated structures. The glycan array shows that out of 610 glycans, the humanized antibodies, the chimeric, and mouse JAA-F11 only bind TF-Ag and four other TF-Ag containing saccharide structures. The four additional saccharides that mouse JAA-F11, the chimeric and hJAA-F11 constructs bind to out of the 440 or 610 saccharides tested should not be biologically problematic for tumor targeting with JAA-F11. Neu5Acα2-6(Galβ1-3GalNAcβ, GlcNAcβ1-6(Galβ1-3)GalNAcβ and Galβ1-4GlcNAcβ1-6(Galβ1-3)GalNAcβ unsubstituted have only been found in excreted fluids, in cancer or other disease states. The Neu5Acβ2-6 Galβ1-3GalNAc is not a natural structure and is not in humans.

Specificity of the humanized JAA-F11 constructs appears to be the same or even improved when compared to the chimeric and mouse antibodies. For example, H2L3 shows statistically (p<0.05 by ANOVA) less binding with any addition to TF-Ag, and H1L1 and H2L2 do not permit a disaccharide to be added to the C-6 hydroxyl of the GalNAc and this is statistically different (p<0.05) from the other antibodies.

The lack of binding with more than 600 negative saccharides on the array indicates likely targeting ability for all these antibodies. Important examples of closely related saccharides which do not bind are the Galβ1-3GalNAc-beta linked structures, indicating that the antibody would bind to tumor tissues and not to the central nervous system GM1 ganglioside, the asialo-GM1 of NK cells, the GD1 of glycolipids or to asialo GM1 of peripheral nerve tissue (these are beta-linked). The well-known elongation of TF-Ag on normal tissues is carried out by β1-3N-acetylglucosaminyl-transferase adding GlcNAcβ1-3 on the Gal, forming GlcNAcβ1-3Galβ1-3GalNAcα-Sp8, or by a 2-3 sialyltransferase forming Neu5Acα2-3Galβ1-3GalNAc (sialyl-TF) or with a second sialyltransferase forming Neu5Ac2-3Galβ1-3(Neu5Acα2-6)GalNAc (disialyl-TF) all of which do not bind the mouse, chimeric or the humanized JAA-F11. Thus normal tissue binding is not expected for JAA-F11 or the hJAA-F11 constructs.

Relative Affinity Analysis

The relative binding affinities of the four hJAA-F11 and chimeric antibodies to TF-Ag were determined by comparing the ability of the mouse antibody to compete with the humanized antibodies in an enzyme immunoassay. In this assay, the 3 μg of each humanized Ab is mixed with serial dilutions of the mouse anti TF-Ag antibody (mJAA-F11). Binding of the human anti-TF-Ag to the TF-Ag coated plate is measured using a species specific anti-human IgG. The amount of mouse mJAA-F11 required to inhibit 1 μg of hJAA-F11 to 50% is extrapolated and taken as a measure of relative affinity. The higher the amount of mouse antibody required for inhibition, the higher the relative affinity of the antibody.

The results are summarized in FIG. 3 and Tables 2 and 3. Table 2 shows the half maximal inhibitory concentration of mouse JAA-F11 required (IC50) by the different antibodies to compete with 1 µg of this humanized antibody. H2L2 is shown with the highest relative affinity to TF-Ag among the antibodies, with an IC50 2.31 µg of mouse antibody. Table 3 shows the p-values calculated for each antibody against each other ANOVA—Tukey post-hoc test. It can be seen that this improved affinity difference of H2L2 antibody is statistically significant (p<0.05), when compare to each of the hJAA-F11 and chimeric antibody, except for H2L3 where it approached significance (p=0.057) (Table 3). H2L3 is not significantly different from H1L1, H2L2, H3L3 and chimeric antibody. The relative affinities of H1L1, H3L3 and the chimeric antibody are not significantly different from each other.

TABLE 2

Relative affinity of hJAA-F11 and chimeric JAA-F11 antibodies to TF-Ag. $IC_{50}$, Relative Affinity for TF-Ag: µg mJAA-F11 required for 50% inhibition of 1 µg of each hJAA-F11 or chimeric

| H1L1 | H2L2 | H2L3 | H3L3 | Chimeric |
|---|---|---|---|---|
| 1.11 ± 0.18$^a$ | 2.31 ± 0.20 | 1.64 ± 0.39$^a$ | 1.28 ± 0.41$^a$ | 1.14 ± 0.30$^a$ |

$^a$The average of three independent experiments is shown ±1 SD.

TABLE 3

ANOVA analysis was performed on replicates of the IC50 assay to compare the differences between the IC50 of the different antibodies. P < 0.05 significant (enlarged an bolded text).

| P-value (Tukey) | H2L2 | H2L3 | H3L3 | H1L1 |
|---|---|---|---|---|
| H2L2 | | 0.057 | 0.002 | 0.00 |
| H2L3 | 0.057 | | 0.330 | 0.071 |
| H3L3 | 0.002 | 0.33 | | 0.908 |
| H1L1 | 0.00 | 0.071 | 0.908 | |
| Chimeric | 0.00 | 0.093 | 0.948 | 1.00 |

Analysis of Biological Reactivity, Specificity and Activity of hJAA-F11

3hJAA-F11 and chimeric JAA-F11 antibodies bind to human tumor cell lines.

Figure 4:
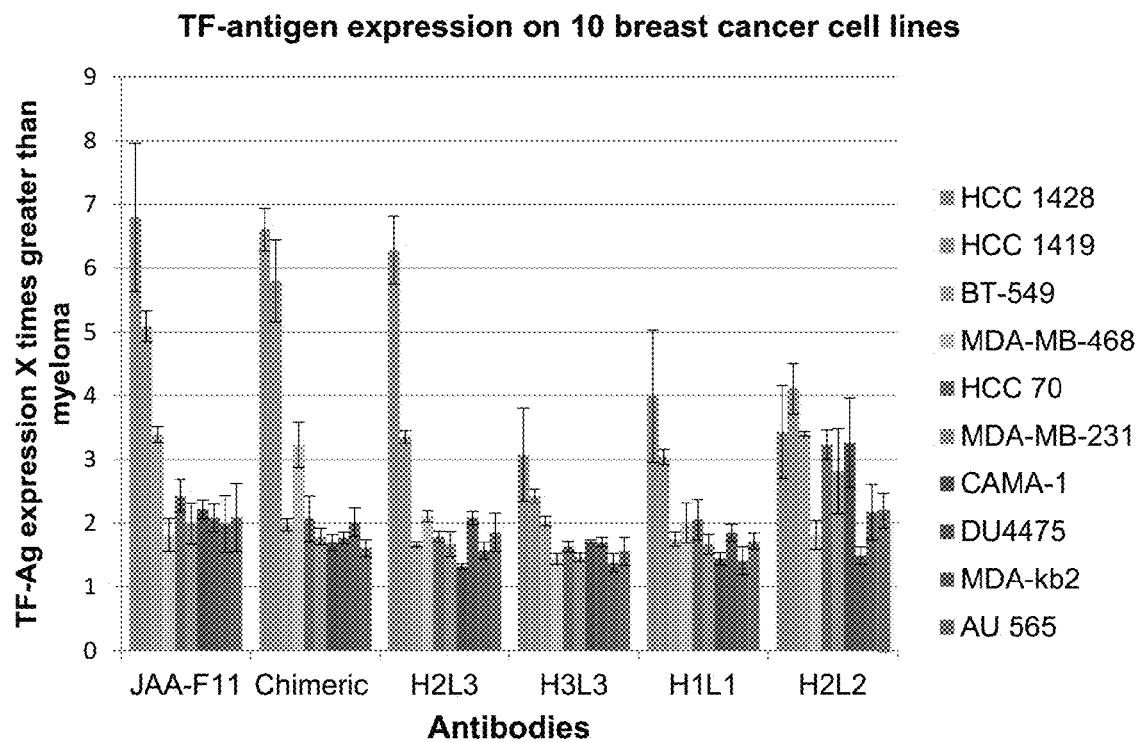
FIG. 4. Binding of hJAA-F11, chimeric and mouse JAA-F11 (50 µg/mL) to 10 breast cancer cell lines. The cell lines include triple negative (HCC 70, BT 549, MDA-MB-231, MDA-MB-468, DU 4475), ER/PR-positive (HCC 1419, AU 565, MDA-kb2), and HER2-positive (CAMA-1, HCC 1428). For all cell lines tested above, binding to hJAA-F11, chimeric or mouse JAA-F11 (at 50 µg/mL) was significantly higher (p≤0.05) (Student's T-test) than that of the TF-Ag negative control myeloma. Each error bar represents ±1 standard deviation.

Binding of hJAA-F11 and chimeric JAA-F11 antibodies to various human breast tumor cell lines was assessed using whole cell ELISA. The TF-Ag positive mouse mammary tumor 4T1 cell line served as a positive control while the P3-X63-Ag8 Myeloma cell line served as the TF-Ag negative control. The assays were performed on three different days and 3 to 4 cell lines were assayed at a time in quadruplicates with the control cell lines. A cell line was considered positive if the relative binding due to hJAA-F11 or chimeric JAA-F11 (at 50 µg/mL) was significantly higher (p<0.05) than that of the TF-Ag negative control myeloma. Results are shown in FIG. 4.

The cancer cell lines tested consist of the different subgroups of breast cancers, hormone receptor positive or negative, Her2-positive or negative, and triple negative. The estrogen receptor (ER) and progesterone receptor (PR) positive cell lines tested were CAMA-1 and HCC-1428. Two Her2/neu receptor positive cell lines, HCC-1419 and AU-565 were tested. The triple negative breast cancer (TNBC) cell lines tested were HCC-70, MDA-MB-231, MDA-MB-468, DU-4475, AND BT-549. One cell line, MDA-kb2, expresses androgen receptor but is estrogen receptor negative. These breast cancer cell lines have been examined previously using mouse JAA-F11 and all were positive for TF-Ag expression. In this disclosure, results show that the hJAA-F11 and chimeric JAA-F11 antibodies bind to all 10 breast cancer cell lines examined, confirming the expression of TF-Ag on these cell lines. Among the different breast cancer subgroups, currently there is no targeted therapy for treating TNBC patients. The data obtained indicate a therapeutic role of TF-Ag in targeting the aggressive TNBC and the use of hJAA-F11 antibodies to treat and increase survival of breast cancer patients regardless of receptor status. Table 4 summarizes the types of breast cancers and the expression of TF-Ag of each cell line tested.

TABLE 4

Table of breast cancer cell lines tested in whole cell ELISA. Table shows hormone receptor, Her2/neu receptor, and expression of TF-Ag. Triple negative (bold), ER/PR positive (italics), and HER2-positive (bold and italics). MDA-kb2* is negative for estrogen receptor but expresses androgen receptor.

| Cell Line | Estrogen Receptor | Progesterone Receptor | Her2/neu Receptor | TF-Ag Expression |
|---|---|---|---|---|
| HCC-70 | − | − | − | + |
| BT-549 | − | − | − | + |
| MDA-MB-231 | − | − | − | + |
| MDA-MB-468 | − | − | − | + |
| DU-4475 | − | − | − | + |
| *CAMA-1* | + | + | − | + |
| *HCC-1428* | + | + | − | + |
| *HCC-1419* | − | − | + | + |
| *AU 565* | − | − | + | + |
| MDA-kb2* | − | − | − | + |

Humanized JAA-F11 Inhibits Proliferation of Cancer Cells In Vitro

Figure 5:
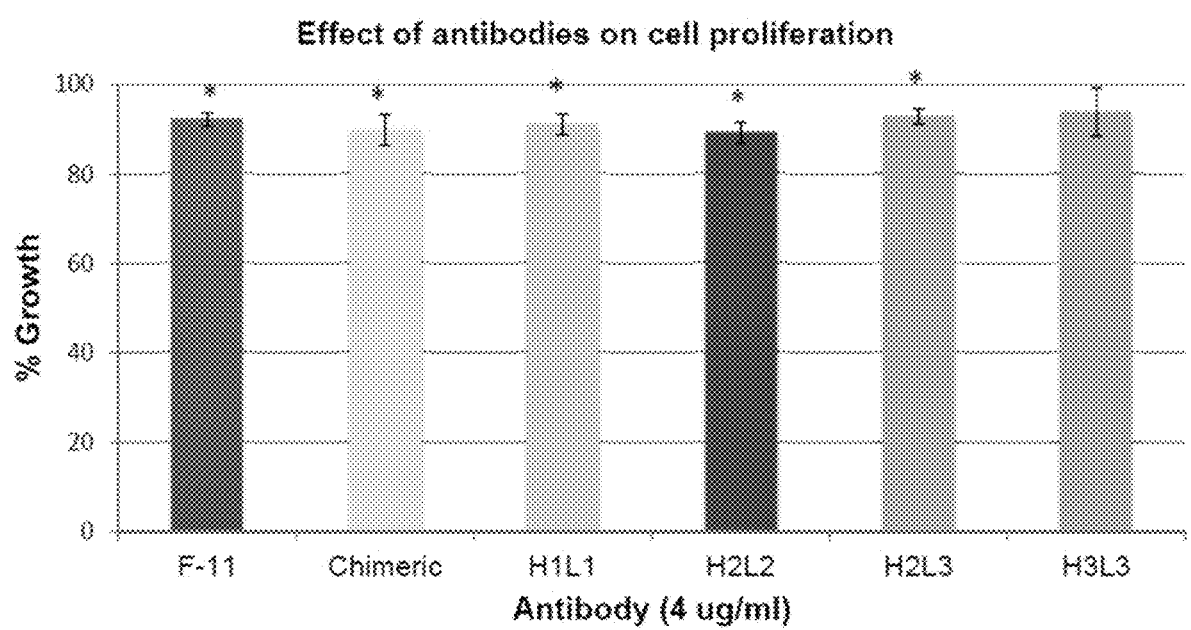
FIG. 5. The chimeric antibody and the humanized JAA-F11 antibodies except for H3L3 caused a small (~6-11%) but statistically significant inhibition of tumor cell growth. No enhancement of cell proliferation was seen. No significant result was seen for any of the antibodies at 2 or 1 ug/ml.

Since some anti-TF-Ag antibodies have been shown to cause tumor cell proliferation, it was important to determine the effect of the different constructs on cell proliferation. The MTT assay which measures metabolic activity was chosen as a surrogate for the tritiated thymidine direct proliferative assay. The effect of the humanized, chimeric, and mouse JAA-F11 antibodies on cancer cell growth compared to a control without antibody was determined at 4 ug/ml of the antibodies by known methods. The data is shown in FIG. 5. The chimeric antibody and the humanized JAA-F11 antibodies except for H3L3 caused a small (~6-11%) but statistically significant inhibition of tumor cell growth. No enhancement of cell proliferation was seen.

Humanized JAA-F11 Induces ADCC

Antibody-dependent cell mediated cytotoxicity (ADCC) was performed on human breast tumor cell lines using the CytoTox 96 Non-Radioactive Cytotoxicity assay; Promega, Madison, Wis.) based on the lactate dehydrogenase (LDH) release assay according to standard techniques with the following adaptations. Fresh human peripheral blood mononuclear cells were isolated from EDTA anti-coagulated whole blood for use with the humanized antibody and 4T1 mouse breast cancer cells in an effector to target ratio of 100:1. The release of LDH was used to quantify cytotoxicity.

Figure 6A:
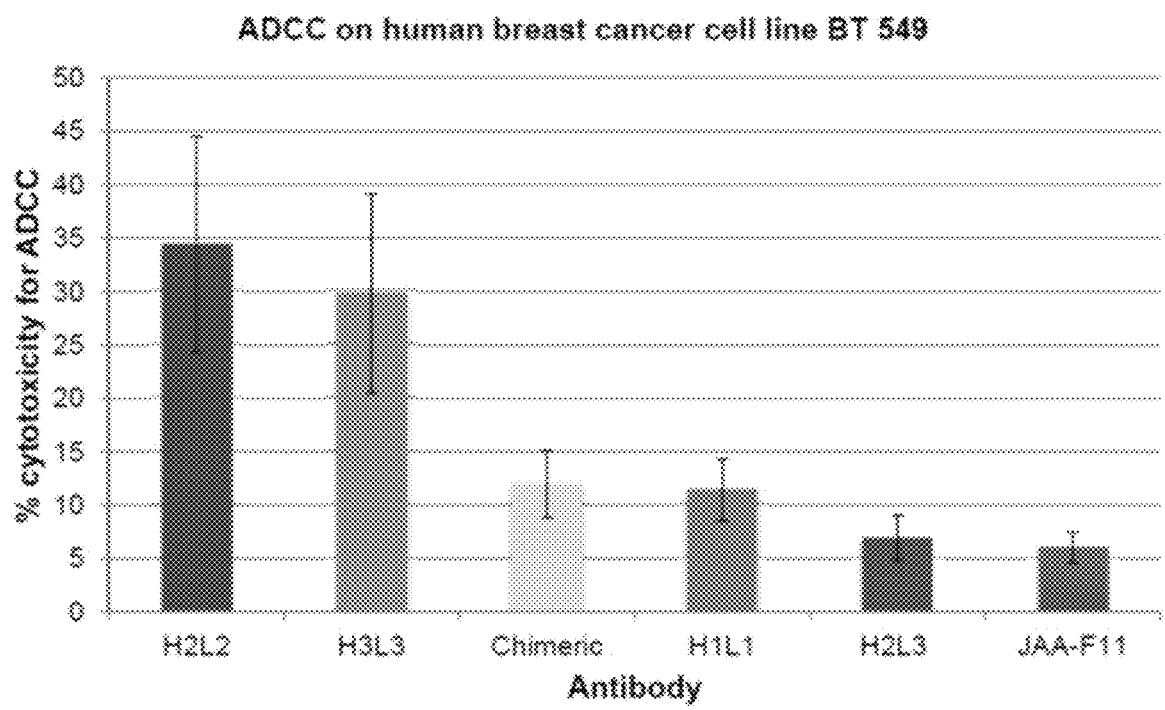
FIG. 6A. ADCC activity of mouse, chimeric, and 4 hJAA-F11 constructs against a TF-Ag positive human breast cancer cell line (BT 549). Results are presented as percent cell lysis in antibody treated cells compared to 100% lysis of cells. H2L2 and H3L3 showed statistically more ADCC activity than chimeric or mouse antibodies (p<0.05) in all cases in the human cell line. This is representative average of all experiments on PBMCs from Donor #1 and Donor #2 (more than 3 independent experiments). Error bars represent ±1 standard error.
Figure 6B:
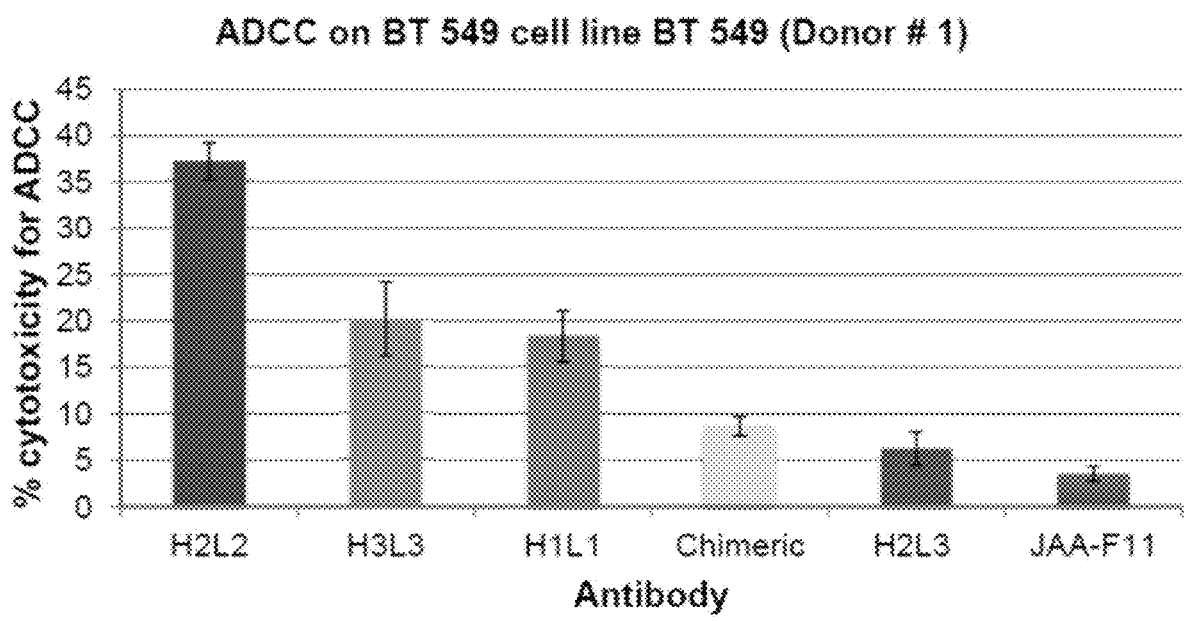
FIG. 6B. ADCC activity of mouse, chimeric, and 4 hJAA-F11 constructs against a TF-Ag positive human breast cancer cell line (BT 549) on PBMCs Donor #1. Results are presented as percent cell lysis in antibody treated cells compared to 100% lysis of cells. H2L2 and H3L3 showed statistically more ADCC activity than chimeric or mouse antibodies (p<0.05) in all cases in the human cell line. This is average of at least 3 independent experiments. Error bars represent ±1 standard error.
Figure 6C:
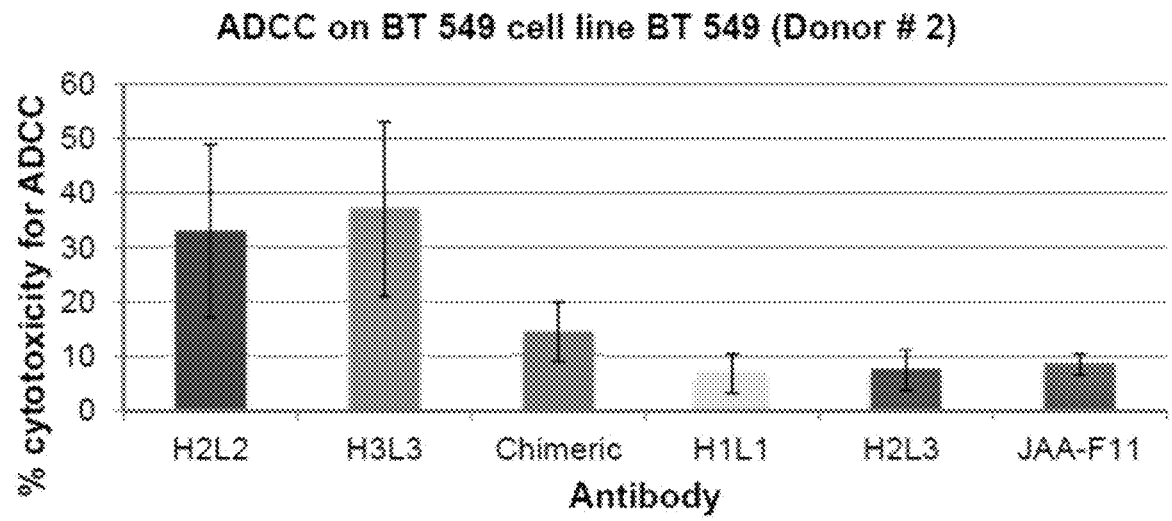
FIG. 6C. ADCC activity of mouse, chimeric, and 4 hJAA-F11 constructs against a TF-Ag positive human breast cancer cell line (BT 549) on PBMCs from Donor #2. Results are presented as percent cell lysis in antibody treated cells compared to 100% lysis of cells. H2L2 and H3L3 showed statistically more ADCC activity than chimeric or mouse antibodies (p<0.05) in all cases in the human cell line. This is the average of at least 3 independent experiments. Error bars represent ±1 standard error.
Figure 6D:
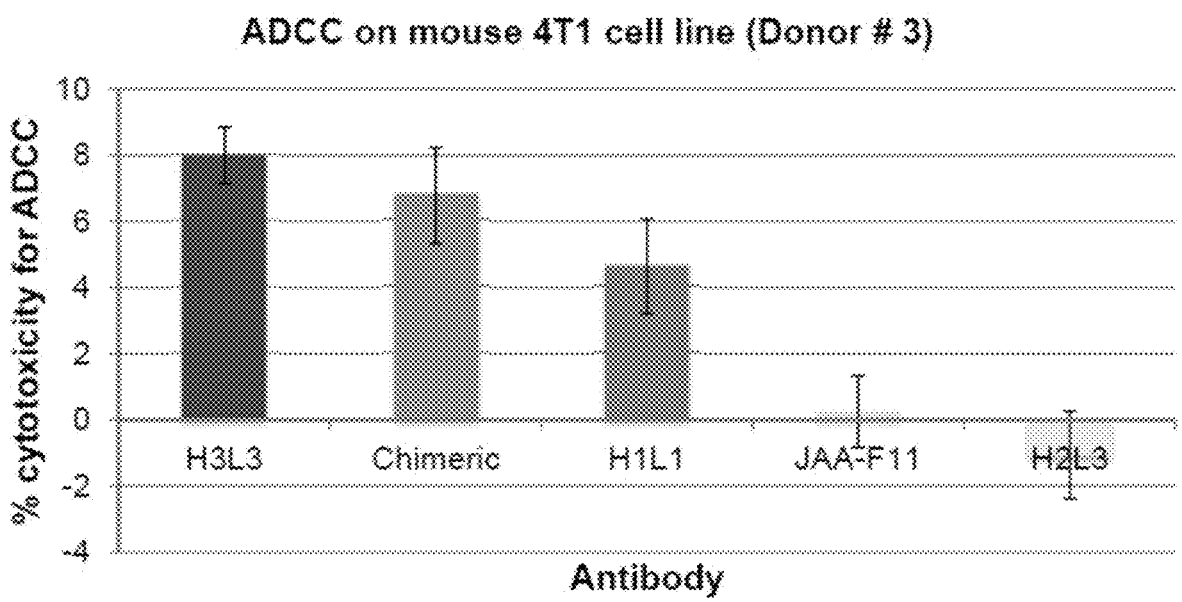
FIG. 6D. ADCC activity of mouse, chimeric, and 3 hJAA-F11 constructs against 4T1 TF-Ag positive mouse breast cancer cell line. Results are presented as percent cell lysis in antibody treated cells compared to 100% lysis of cells. H3L3 and chimeric showed statistically more ADCC activity than mouse antibody (p<0.05). Error bars represent ±1 standard error. ADCC was performed only once with PBMCS from Donor #3.

FIG. 6A shows the amount of ADCC facilitated by the mouse, chimeric, H1L1 and H3L3 antibodies compared on a human breast cancer cell lines, BT 549. The experiments were repeated more than three times. In all experiments, H2L2 and H3L3 showed significantly more (p<0.5) ADCC than either the chimeric or the mouse antibody in the human cell lines. More than 20% of the TF-Ag bearing BT549 and HCC70 target cells were lysed by H2L2 and H3L3 antibody at 200 µg/mL at a 100:1 effector to target (E:T) ratio. Likewise, in all experiments on the mouse 4T1 cell line, although all the antibodies tested induced less than 10% ADCC, H3L3 antibody showed significantly more (p<0.05) ADCC than either the chimeric or the mouse antibody. This indicates that currently the H2L2 and H3L3 antibody is the best choice for immunotherapy. In contrast, mouse JAA-F11 did not show statistically significant ADCC capabilities in any of the tests. The ADCC results from three individual PBMCs donors are as shown in FIGS. 6B, 6C, and 6D.

Humanized JAA-F11 does not Induce CDC

Figure 7:
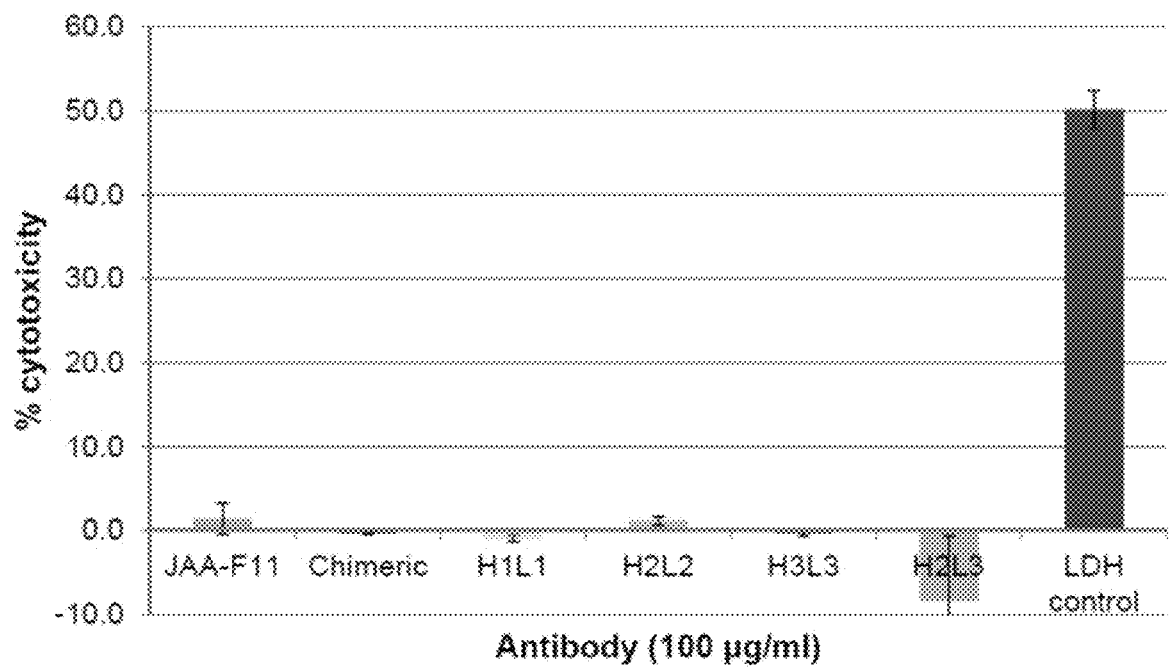
FIG. 7. Humanized, Chimeric and Mouse JAA-F11 do not induce complement dependent cytotoxicity (CDC). CDC activity of mouse, chimeric, and 2 hJAA-F11 constructs against the human HCC 1428 breast cancer cell line were tested. Results are presented as percent cell lysis in antibody treated cells compared to 100% lysis of cells. Positive control: LDH positive cells included in the reagent kit showed lysis. Error bars represent ±1 standard error.

The ability of hJAA-F11 and chimeric antibodies to mediate complement dependent cytotoxicity (CDC) was determined by the lactate dehydrogenase (LDH) release assay using human breast cancer cell HCC-1428 cells as the target cells. The LDH positive control provided with the reagent kit was used as a positive control and showed lysis. The mouse JAA-F11, chimeric, H1L1, H3L3, H2L3 antibodies did not induce complement-dependent cytotoxicity as no lysis occurred as shown in FIG. 7.

Humanized JAA-F11 Internalizes into Cancer Cells

Figure 8:
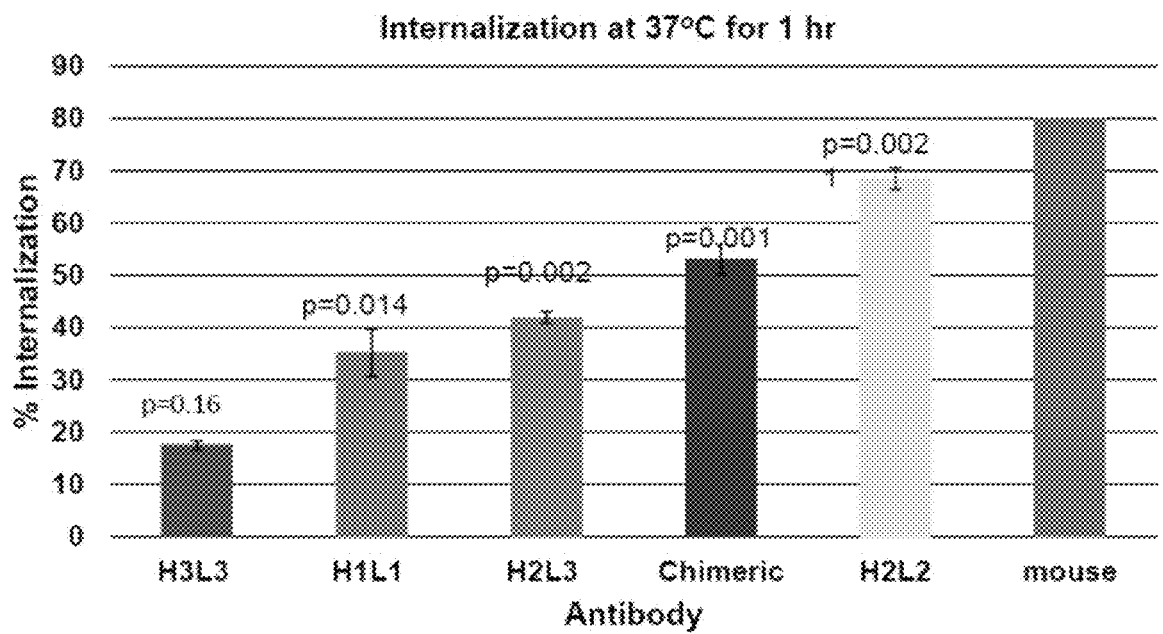
FIG. 8. Internalization of mouse, chimeric, and 4 hJAA-F11 antibodies using an enzyme immunoassay to measure surface binding. Internalization was analyzed by incubation of mouse 4T1 breast cancer cells with antibodies at 37° C. or 4° C. As expected, the pattern was opposite the ADCC pattern shown for H3L3 but was unexpected for H2L2 which induced ADCC and internalized. Mouse, H2L2, chimeric Ab, H2L3, and H1L1 internalized significantly (p<0.05). Error bars represent ±1 Standard error.

Internalization of humanized and chimeric JAA-F11 into 4T1 breast tumor cells was determined by two methods, an enzyme immunoassay with surface binding measured and compared after incubating the cells at either 4° C. or 37° C., and an immunofluorescent microscopy method with LAMP-1 (lysosomal associated membrane protein, a lysosomal marker) and DAPI staining for nuclear staining. In the enzyme immunoassay, as shown in FIG. 8, mouse, H2L2, chimeric, H2L3, and H1L1 antibodies internalized significantly with p-values of 0.001, 0.002, 0.001, 0.002, and 0.014 respectively. However, H3L3 antibody did not show significant internalization (p=0.16) and this is expected as H3L3 showed significantly more (p<0.5) ADCC than the chimeric or the mouse JAA-F11.

In immunofluorescent experiments, in agreement with the enzyme immunoassay mouse, chimeric, H2L2, H2L3 antibodies showed internalization and co-localization with the LAMP-1 and H3L3 showed membrane staining that did not internalize. This data confirmed that obtained using the surface enzyme immunoassay. One would expect that the antibodies that showed higher ADCC activity would show lower internalization since antibody presence on the cell surface is needed for ADCC function. Internalization assays have been performed on the hJAA-F11, chimeric and mJAA-F11. H3L3 showed agreement with this expectation, having low amounts of internalization but relatively high ADCC. H1L1, H2L3, chimeric and mJAA-F11 all showed statistically significant internalization and did not perform ADCC well. An unexpected result was observed for H2L2 antibody which induced high ADCC similar to H3L3 but showed the highest internalization percent activity compared to the chimeric and other humanized antibodies.

The immunofluorescent internalization experiment was initially performed using 5 µg/mL of antibody and was repeated using antibody concentrations at 0.1 µg/ml, and the antibodies that internalized did so even at this low concentration. The above data indicates that due to high percentage of internalization, and the rapid rate of this internalization, the chimeric, the H2L2 and H2L3 constructs have the potential to be used as antibody-drug conjugates. The glycan specificity, relative affinity internalization, ADCC, and CDC data are summarized in Table 5 below.

TABLE 5

Summary of internalization, ADCC and glycan specificity of mouse, humanized and chimeric JAA-F11.

| JAA-F11 variants | ADCC | CDC | Internalization | Increased Specificity for TF-Ag | Affinity Rank |
|---|---|---|---|---|---|
| Mouse | No | No | Yes | No | |
| Chimeric | No | No | Yes | No | 3 |
| H1L1 | Yes | No | No | Yes | 3 |
| H2L2 | Yes | No | Yes | Yes | 1 |
| H2L3 | No | No | Yes | Yes | 2 |
| H3L3 | Yes | No | No | No | 3 |

MicroPET Imaging

Figure 9:
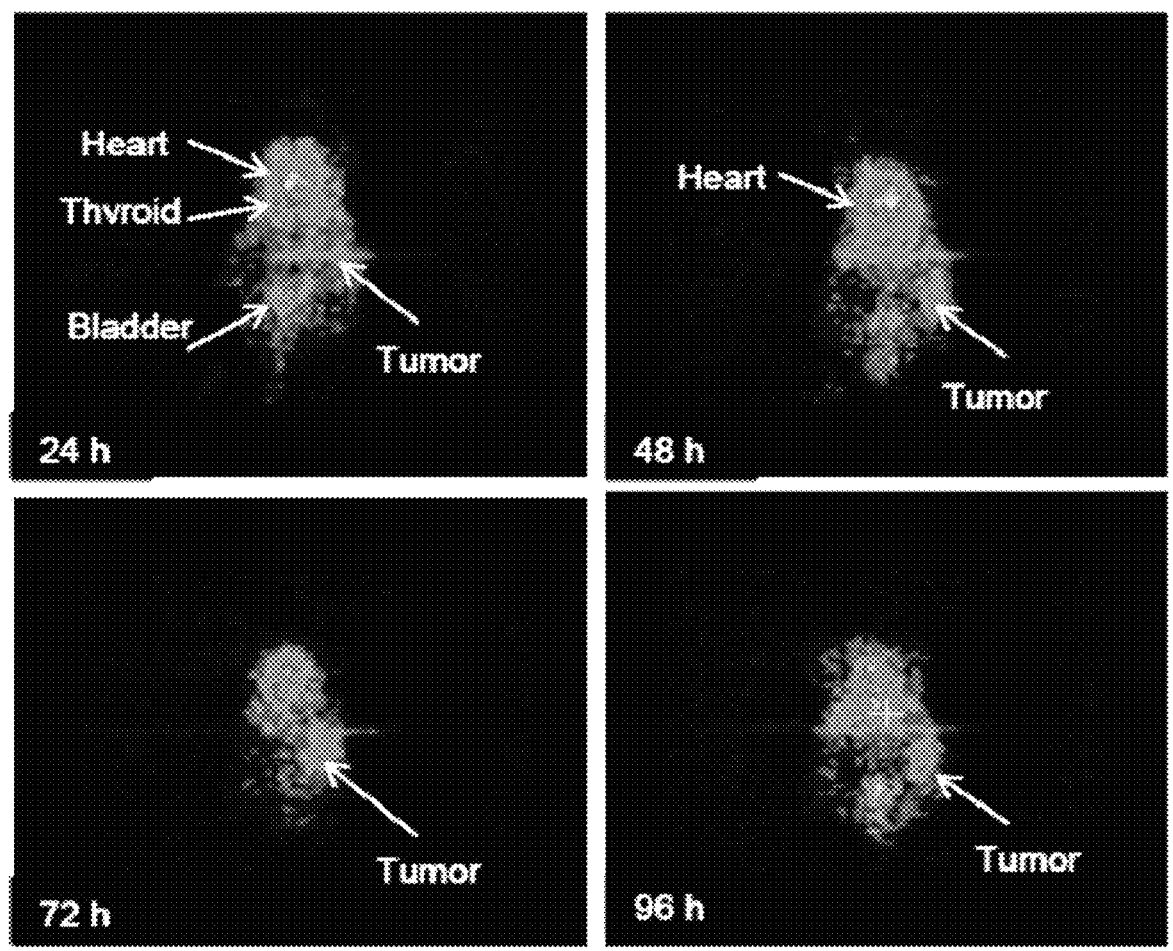
FIG. 9. MicroPET images showing immunolocalization of hJAA-F11 antibody in 4T1 tumor bearing mouse.
Figure 10:
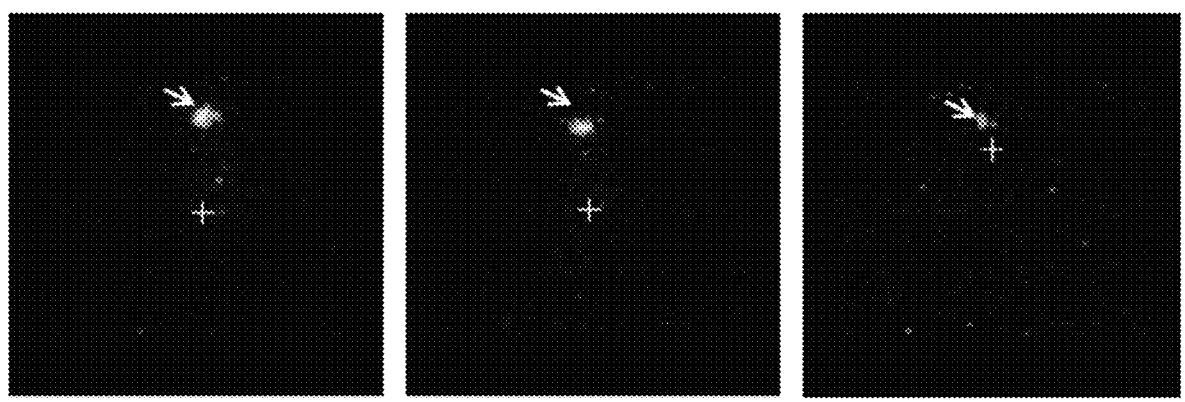
FIG. 10. MicroPET images showing localization of free 124Iodine to the thyroid in 4T1 tumor bearing mouse.

MicroPET imaging was performed serially on one mouse each that was injected with 124Iodine-hJAA-F11 H2L2 antibody, and with free 124Iodine. Imaging was performed at 24, 48, 72, 96, 168, and 192 hours. FIG. 9 shows the coronal view of a mouse injected with 124Iodine-hJAA-F11 H2L2 antibody at different time points, while FIG. 10 is of a control mouse injected with free 124Iodine. Uptake of the radiolabeled antibody by the tumor was observed at 24, 48, 72, and 96 hours after injection. Uptake of antibody was also seen in the spleen at 48 hours (FIG. 9). The negative control mouse bearing the 4T1 TF-Ag positive tumor, which received free 124Iodine only showed that there was no localization to any organs or tumor except to the thyroid throughout the study (FIG. 10).

The fully murine JAA-F11 has potential for passive humoral immunotherapy and drug conjugate therapy in breast cancer patients. However, as the use of mouse antibodies in humans had been shown to be limited by the development of human anti-murine antibody (HAMA) responses and a short half-life in patients, humanization is desirable to decrease the immunogenicity of the mouse JAA-F11 antibody and also allow it to remain in circulation for a longer time.

It will be recognized from the foregoing description of results that this disclosure provides, among other aspects, a description of a novel approach to humanization of the mouse JAA-F11 mAb, and comparisons and contrasts between the mouse, chimeric and humanized JAA-F11 antibodies. The mJAA-F11 was humanized in part by CDR grafting. As will be recognized by those skilled in the art, traditionally, humanization by CDR-grafting uses a single human antibody acceptor framework [Jones, et al. Replacing the complementarity-determining regions in a human antibody with those from a mouse. 1986. Nature 321: 522-525]. Thus, the human framework sequences is chosen from existing human germline genes. In contrast, in the present disclosure, three novel and different approaches were used to select the human acceptor antibody framework for the heavy and light JAAF11 variable region chains, generating three variants of the heavy chain (H1, H2, H3) and 3 variants of the light chain (L1, L2, L3). As discussed above, any of the 3 heavy chains (VH) can pair with any of the 3 light chains (VL) to create a total of 9 possible hJAA-F11 VH/VL combination variants. A chimeric JAA-F11 which has the whole mouse variable region and a human IgG1 and kappa constant regions was also generated, and used as a control.

One concern was whether the approach used in defining the CDRs and FR regions would reduce the immunogenicity of the humanized antibodies. The T20 score method developed by Gao et al [Monoclonal antibody humanness score and its applications. 2013. BMC Biotechnology, 13:55], and validated with analysis of 90 antibodies that have been utilized in patients, was used to predict the immunogenicity of the humanized JAA-F11 variants. The T20 scores of the humanized JAA-F11 variants are all higher (improved) (>85) than the chimeric JAA-F11 (<85), indicating that humanization of heavy and light variable chains by all three of the present methods created hJAA-F11 variants that will be less immunogenic than the chimeric variant.

We humanized the mouse JAA-F11 and five antibodies have been produced using CHO-K1 cells, a chimeric and 4 hJAA-F11 constructs, H1L1, H2L2, H3L3 and H2L3. Thus, given the benefit of the present disclosure, the skilled artisan could make any use the other four possible VH and VL combinations.

Antibody humanization by CDR-grafting can cause a decrease in affinity or loss of antigen binding, which may be due to the CDRs conformation and antigen binding site being negatively affected by changes in some framework amino acid residues in the humanized antibody. CDRs are made up of residues that interact with the framework regions and other CDRs. In addition to the interaction of CDR amino acids with sequentially nearby amino acids, some framework residues that can affect antigen binding directly or indirectly include the Vernier zone residues and residues at the VL/VH interface. Vernier zone residues are residues in the β-sheet framework underlying the CDRs which provide a foundation for the conformation of loop structures. Vernier residues on the light chain are at position 2, 4, 35, 36, 46, 48, 49, 64, 67, 69, and 71, while on the heavy chain they are identified at position 2, 27, 28, 29, 30, 47, 48, 49, 67, 69, 71, 73, 78, 93, 94, and 103. Residues at the VL/VH interface have been identified by Chothia and co-workers [Chothia C, et al. The packing of variable domains. 1989. J. Mol. Biol. 186:651-63], and are at position 34, 36, 38, 44, 46, 87, 89, 91, 96, and 98 of the light chain, and at position 35, 37, 39, 45, 47, 91, 93, 95, 100-100K, and 103 for the heavy chain.

We showed that the approaches used in this disclosure for selecting the human FR and CDRs did not negatively alter the affinity of the humanized JAA-F11 for the TF-Ag, relative to the chimeric and mouse JAA-F11. When defining the CDRs, residues within 5 Å to 6 Å of the binding site had been included to ensure that affinity and specificity to TF-Ag is maintained. These residues are at position H31, H32, H33, H35, H50, H52, H53, H54, H95, H96, H97, H98, and H100 on the heavy chain, and at positions L27d, L28, L30, L32, L34, L50, L89, L91, L92, and L96 on the light chain. However, from the relative affinity studies, whereas all the humanized antibodies maintain the affinity for the TF-Ag, we observed differences in affinity between the antibodies. The relative affinity studies revealed that H2L2 antibody is has the highest affinity antibody, followed by H2L3 antibody. H2L2 antibody has the highest relative affinity to TF-Ag among the antibodies, requiring over 2 mg of mouse antibody for the inhibition of 1 mg of H2L2 antibody. The H2L3 antibody also had higher affinity than H1L1 and the chimeric antibody although not significantly, while the relative affinities of H1L1, H3L3 and the chimeric antibody to TF-Ag are not significantly different from each other.

These improvements in affinity can be attributed the changes in some residues between the different humanized variants. The differences between the variants are listed below in Table 6 and 6B.

TABLE 6A

Differences between heavy variable H1, H2, H3 and mouse sequences.

| POSITION | H1 | H2 | H3 | Mouse |
|---|---|---|---|---|
| 5 | Valine | Leucine | Valine | Leucine |
| 11 | Valine | Leucine | Valine | Leucine |
| 38* | Arginine | Arginine | Lysine | Lysine |
| 48*** | Methionine | Methionine | Isoleucine | Isoleucine |
| 66* | Arginine | Arginine | Lysine | Lysine |
| 67*** | Valine | Valine | Alanine | Alanine |
| 69*** | Methionine | Leucine | Methionine | Leucine |
| 73** | Threonine | Lysine | Threonine | Lysine |
| 75 | Isoleucine | Serine | Isoleucine | Serine |
| 82b | Arginine | Serine | Arginine | Serine |
| 83 | Arginine | Threonine | Arginine | Threonine |
| 85 | Aspartate | Glutamate | Aspartate | Glutamate |
| 108* | Leucine | Threonine | Threonine | Threonine |
| 109* | Valine | Valine | Leucine | Leucine |
| 12 | Lysine | Lysine | Lysine | Alanine |
| 20 | Valine | Valine | Valine | Methionine |
| 40 | Alanine | Alanine | Alanine | Arginine |
| 76 | Serine | Serine | Serine | Threonine |
| 81 | Glutamate | Glutamate | Glutamate | Glutamine |

**indicates Vernier zone position.
*indicates that this position is within 4 amino acids of our modified CDR.

TABLE 6B

Differences between light variable L1, L2, L3 and mouse sequences

| POSITION | L1 | L2 | L3 | Mouse |
|---|---|---|---|---|
| 1 | Aspartate | Aspartate | Aspartate | Glutamic Acid |
| 2** | Valine | Valine | Valine | Leucine |
| 7 | Serine | Threonine | Serine | Threonine |
| 14 | Threonine | Threonine | Threonine | Asparagine |
| 17 | Glutamine | Glutamine | Glutamine | Aspartic Acid |
| 18 | Proline | Proline | Proline | Glutamine |
| 36*** | Phenylalanine | Phenylalanine | Tyrosine | Tyrosine |
| 37* | Glutamine | Glutamine | Leucine | Leucine |
| 39* | Arginine | Arginine | Arginine | Lysine |
| 45 | Arginine | Arginine | Arginine | Lysine |
| 81 | Glutamic Acid | Glutamic Acid | Glutamic Acid | Aspartic Acid |
| 83 | Valine | Valine | Valine | Leucine |

**indicates Vernier zone position.
*indicates that this position is within 4 amino acids of our modified CDR.

As mentioned above, framework residues affecting antigen binding include the Vernier zone and VL/VH interface residues. When comparing the humanized constructs, the mAbs of this disclosure retain most of the Vernier zone and VL/VH interface residues that may be important for the binding site conformation, however some changes were made to create the less immunogenic humanized variants. The amino acids that were changed that were in the Vernier zone or in the VH/VL interface, and changes have been made to amino acids within 4 amino acids (sequentially) to the CDRs, are as indicated by the asterisks. There are four Vernier zone positions on the heavy chain sequence that differ between the three constructs, positions 48, 67, 69, and 73. H2 retains mouse residues but differs between H1 and H3 constructs at eight positions 5, 11, 69, 73, 75, 82b, 83, and 85. Of these eight residues, two are Vernier zone residues, at positions 69 and 73. At the same time, H2 and H1 have substitutions at two Vernier zone positions, that is, at residue 48 and 67, which are maintained as mouse residues on H3. Since there is no difference in affinity between H1L1 and H3L3, this suggest that the Vernier zone positions at 48 and 67 may not likely contribute to the affinity difference as they are maintained in H3, but changed in H1. H2, however, retains the mouse Vernier zone residues at positions 69 and 73, unlike H1 and H3, suggesting the changes at these two Vernier zone positions may contribute to the differences in affinity.

These two Vernier zone residues that underlie the CDR2 may have enhanced H2 binding compared to H1 and H3. Of the amino acids different between the humanized constructs, positions 69 and 108 are the closest to the binding site. The amino acid in position 69 in H2 (like in the mouse antibody) is Leucine while both of the other humanized constructs have Methionine. Of the differences between H2 and the mouse antibody, changes at amino acids 38, 48, 66, 67, and 109 are nearest the CDRs and also may affect the affinity.

Since H2L2 has a higher affinity than H2L3 the comparison of L2 and L3 may help further delineate the reason for this difference. There were no changes for the VL/VH residues and most of the Vernier zone residues on the light chain were maintained among the 3 humanized constructs, except for Vernier positions 2 and 36. Unlike L3, but like the mouse antibody, the higher affinity L2 has a Phenylalanine rather than Tyrosine at Vernier position 36. The amino acids at position 36 and 37 may influence the conformation in a favorable way, since they are within 5 Å of the binding site, and are part of the amino acids in positions 24-35 which were found to be important in the maintenance of the alpha linkage requirement at the reducing terminus of the GalNAc.

Many normal tissues have non-identical but very similar structures to TF-Ag such as the Galβ1-3GalNAc-beta linked structures that are normally found in the central nervous system, on NK cells, and peripheral nerve tissue, thus maintenance of fine specificity is the key feature in this humanization. The hJAA-F11 H1L1, H2L2, H3L3, and the chimeric antibody retained the same or improved fine specificity of antigen binding as compared to the mouse antibody including the limitation of binding to the Galβ1-3GalNAc-α (TF-Ag) linked structures, and the lack of binding with α2-3 sialylated structures based on the glycan array. Specificity of the humanized JAA-F11 constructs appears to be the same or even improved when tested against over 600 different saccharides. The mouse JAA-F11 and all humanized constructs react with just 5 saccharides, TF-Ag and 3 trisaccharides with one additional sugar 1-6 linked to the GlcNAc (NeuAc in 2, and GlcNAc in the 3rd) or with one with 2 additional sugars GalGlcNAc linked 1-6 to the GalNAc. For example, H2L3 showed less binding on all 4 other saccharides that bind to JAA-F11, while H1L1 and H2L2 have no binding to the tetrasaccharide that binds to JAA-F11, when compared to the chimeric and mouse antibodies. Although these 4 other saccharides that bind to JAA-F11 are not known to be expressed on normal tissues, increased specificity for the target structure is always desirable. This demonstrates the likely targeting ability for all these antibodies in human therapy. Since H2L3 has increased binding specificity as shown by less binding to 3 of the 4 saccharides compared to the other constructs, the difference between H2 and H3 may have cause this difference. The differences between variants that have already been discussed in the affinity section may have been the reason for this improved specificity. H2L3 differs from H2L2 in its decreased binding to NeuAcalpha2-6(TF-Ag) and GlcNAcbeta2-6(TF-Ag).

Without intending to be constrained by theory, it is believed the reason H1L1 and H2L2 do not bind at all to the tetrasaccharide may have to do with a shared difference between these antibodies when compared to the H3L3 and mouse antibodies. H1 and H2 both have a Methionine at position 48, which is both a Vernier zone position and is sequentially within 4 amino acids of the CDR. This methionine is rather than the isoleucine of the mouse and H3 antibodies.

In the present disclosure, whole cell EIA results highlight the ability of the hJAA-F11 and chimeric JAA-F11 antibodies to bind triple-negative breast cancer cell lines. The data obtained suggest a potential therapeutic role of TF-Ag in targeting all breast cancer but especially the aggressive triple-negative breast cancers (TNBC) as there are no targeted therapies for these types of cancers at present.

Some lectins and antibodies which bind TF-Ag cause increased proliferation of TF-Ag expressing tumor cells. This is thought to usually be linked to whether the lectin or antibody binds both the alpha and beta anomers at the reducing end (proliferation causing) or just the alpha anomer (inhibitory). While mouse JAA-F11 only binds the alpha anomer and did not cause proliferation of tumor cells, it is important to determine if the humanized constructs had this effect on tumor cells. Humanized JAA-F11 and chimeric antibodies do not cause proliferation of cancer cells in vitro, on the contrary, similar to the effect of mouse JAA-F11 a small (~6-11%) but significant inhibition of mouse 4T1 and human cancer cells growth was observed.

As ADCC is one of the major mechanisms by which antibodies eliminate tumor cells, and is important for an antibody to be utilized for cancer therapy, the ability of the humanized JAA-F11 variants to induce ADCC was examined. ADCC activity was seen with some but not all of the humanized constructs, and was seen with PBMCs of three individuals. Both H2L2 and H3L3 antibody induced significantly more ADCC than either the chimeric or the mouse antibody of both mouse 4T1 and human breast cancer cell lines, indicating that currently the H2L2 and H3L3 antibody may be the preferred choices for direct passive immunotherapy. The mouse JAA-F11 did not show any statistically significant ADCC abilities in any of the tests. Another effector function that antibodies used for killing tumor cells is CDC. None of the humanized, chimeric and the mouse JAA-F11 antibodies induced CDC, but this lack of CDC activity does not preclude its use as an immunotherapeutic, indeed Herceptin has been found to induce only a nominal amount of CDC, and this is not one of its modes of action. Data with Rituxan actually shows that complement binding inhibits NK cell binding and decreases efficacy.

Antibodies can potentially be used to carry drugs or toxins in the form of antibody-drug conjugates into the cell. Therefore, we assessed the ability of the humanized JAA-F11 variants to internalize after binding to TF-Ag on cancer cells. Mouse JAA-F11 had previously been show to internalize within 1 hour. Using an enzyme immunoassay, we showed that mouse, H2L2, chimeric, H2L3, and H1L1 antibodies internalize significantly into mouse 4T1 breast cancer cells whereas H3L3 antibody did not show significant internalization. A live cell fluorescent microscopy method confirmed the results obtained from the enzyme immunoassay. We expected the antibodies that showed higher ADCC activity would show lower internalization and results from both internalization assays show agreement with this expectation in that H3L3 antibody exhibited more ADCC than either mouse or chimeric antibodies but did not internalize much. However, H2L2, even though it performed well in the ADCC assay, internalizes well. The mechanism of how both of these can occur with the same antibody is not yet understood, but one possibility is that different production rates in the CHO cells can result in different fucosylation rates, so if H2L2 is less fucosylated it may perform better at ADCC during the time it is on the cell surface even though it is internalized. These results show that the chimeric, the H2L2 and H2L3 constructs have the potential to be used as antibody-drug conjugates.

In certain alternative embodiments the disclosure comprises bi-specific antibody constructs. Those skilled in the art will recognize that bi-specific antibodies comprise two distinct antigen binding segments. In embodiments of the present disclosure, one of the antigen binding segments is directed against an epitope of TF-Ag, and the other is directed to a second, distinct antigen, such as a T-lymphocyte antigen, including but not necessarily limited to a CD3 antigen. As such, and in contrast to antibody-drug conjugates, it is preferable for the TF-Ag binding segment in the bi-specific antibody to exhibit no or low internalization. In other embodiments, antibodies of the present disclosure can comprise tri-specific mAbs, wherein in an otherwise bi-specific mAb the Fc region is modified such that the tri-specific mAb binds to a cell that expresses Fc receptors, such as natural killer cells, and/or antigen presenting cells, i.e., macrophage or dendritic cells.

The mouse 124I-JAA-F11 antibody has been shown to localize to TF-Ag breast tumors in mice. The labeled JAA-F11 antibody remained bound to the 4T1 tumor for at least 20 days and 24 days for a human triple negative breast tumor implying that JAA-F11 could be used to find metastasis and to treat the TF-Ag bearing tumor. To test whether iodine-124 labeled humanized antibody will localize to human breast tumors in mice, the humanized antibody with the highest affinity, H2L2 variant, (which internalizes and performs ADCC) was utilized. The imaging showed preferential tumor uptake, with uptake in the thyroid and in the spleen that was blocked in a later experiment with cold rabbit immunoglobulin. MicroPET imaging showed that the radiolabeled humanized antibody was taken up by the tumor within 24 hours and could be seen until 96 hours. Such radiolocalization in patients could be used to find metastasis and also used to determine if there is any off target binding in a particular patient prior to either direct passive immunotherapy or antibody-drug conjugate therapy.

The Thomsen-Friedenreich Antigen (TF-Ag) is present in more than 80% of several human carcinomas including breast cancers. It has a functional role in tumor adhesion and metastasis so the ability of an antibody to target TF-Ag suggests possible use as an immunotherapeutic, as an antibody-drug conjugate for killing cancer cells and for inhibiting metastasis. The JAA-F11 antibody with its unique high specificity for the TF-Ag holds great potential as a passive anti TF-Ag response for treating breast and other cancers. In our humanization approach, we have maintain this unique specificity and have likely enhanced it with the humanized JAA-F11 variants.

Example 2

This Example provides a description of the materials and methods used to obtain the results described herein.

The JAA-F11 CDRs were previously predicted. We performed cloning and sequencing of mouse JAA-F11 antibody to confirm the amino acid sequences of both the heavy and light chain variable regions.

To have therapeutic benefits in humans, an antibody should maintain its specificity for its target antigen and at the same time not generate anti-mouse immune reactions. We selected the CDR grafting approach to retain the CDRs of the mouse JAA-F11 so as to maintain specificity and affinity for TF-Agα. The CDRs were selected using Chothia and Kabat methods as well as the x-ray crystal structure and computational carbohydrate threading.

To choose a human acceptor antibody framework for each of the heavy and light JAAF-11 variable region chain, a Protein BLAST® (BLASTP) search was performed at blast.ncbi.nlm.nih.gov/Blast.cgi?PAGE=Proteins against the entire non-redundant human (*Homo sapiens*) Genbank database to identify the most homologous human antibodies to mouse JAA-F11. All non-*Homo sapiens* protein sequences, humanized antibodies and phage display sequences were eliminated from the BLASTP results. The resulting top ten most homologous sequences to each of the heavy and light variable chain sequence of JAA-F11 were selected as potential human acceptor antibody frameworks for humanized JAA-F11 (hJAA-F11). The SeaView Sequence Alignment program was used to align the ten potential human acceptor variable heavy or light frameworks sequences with mouse JAA-F11 variable heavy or light region sequences.

Three heavy (H1, H2, and H3) and three light (L1, L2, and L3) variable regions were constructed from the protein BLAST selection of the 10 most similar human immunoglobulin sequences. The final CDRs from mouse JAA-F11 were then grafted onto human framework regions by one of three different methods, creating 3 different heavy chains and 3 different light chains. In the first method, (a) Heavy H1 and Light L1 FR sequences were designed to contain the most frequently occurring human amino acid in each site among the top ten selected human FR sequences. In the second method, (b) Heavy H2 and Light L2 were designed to contain the most frequently occurring human amino acid among the top ten selected human FR sequences in each site, unless an amino acid was present in any of the top ten human FR that matched that seen in the mouse JAA-F11, then the amino acid was kept as in mouse JAA-F11. In the third method, (c) In Heavy H3 or Light L3, the three FR residues before and after the CDR1, CDR2 and CD3 of mouse JAA-F11 were maintained and the rest of the residues were the most frequently seen amino acids in the human sequences as in variants H1 or L1. Any one of these designed heavy variable chains can be paired with any of the similarly designed light variable chain, eg. H1/L1, H1/L2, H1L3, H2L1, H2L3, etc.

A chimeric JAA-F11 was also constructed in which the entire mouse JAA-F11 variable region was attached to a human IgG1 constant region. This is to provide a baseline that should have the original specificity and affinity of the mouse antibody while having the human constant region, to be was used as a positive control for evaluating the humanized variants.

Assessment of Models of hJAA-F11

Various hJAA-F11 constructs were assessed for conformational effects. Briefly, the proposed heavy and light variable chain sequences of various hJAA-F11 constructs were aligned with the JAA-F11 sequence. Any amino acid residue in the framework for each humanized variant that could potentially cause serious steric interaction with surrounding amino acids was removed and replaced with the original mouse JAA-F11 framework residue.

Immunogenicity Prediction of hJAA-F11 Variants Using T20 Score.

Although humanized or fully human antibodies are considered to be non-immunogenic and safe for human use, immunogenicity of fully human and humanized antibodies have been reported in patients. To determine if the selected sequences were of low immunogenicity, an immunogenicity analysis was performed by the T20 score method. The T20 score analyzer, developed by Gao et al, calculates the "humanness" of monoclonal antibody variable region sequences using a database of over 38,000 human antibody sequences.

In this method, a protein BLAST search is performed and the test humanized Ab is first compared against all these human sequences. The humanized antibody is then compared to the top 20 human Ab BLAST matches and scored for similarity to these sequences. T20 score for humanized antibody is obtained from the average of the percent identities of the top 20 matched human sequences. The highest possible score is 100 (most human-like). As proof of concept for the relationship of this method to immunogenicity in the patient, Gao et al compared the in vivo in patient immunogenicity results of more than 90 antibodies that are either approved for clinical use or in various stages of clinical development (mouse, chimeric (from mouse), humanized (n=22), and fully human antibody sequences) with the T20 score, and found that Abs with T20 scores of FR & CDR sequences above 80 were not immunogenic, and using a T20 scores for the FR sequences only, those above 85 were not immunogenic. The T20 scores for the humanized JAA-F11 variants were calculated using the T20 Cutoff Human Databases at abanalyzer.lakepharma.com/.

Codon optimization and gene synthesis. After the design of the humanized JAA-F11 VH and VL variants amino acid sequences, the corresponding nucleotide sequences were selected manually for codon usage optimal for *Cricetulus griseus* (CHO) cell protein production and synthesized and inserted into pUC57 plasmid, a commonly used cloning vector.

Sub-cloning and sequencing of hJAA-F11 and chimeric JAA-F11 variable heavy (VH) and light (VL) genes in mammalian expression vectors. The hJAA-F11 VH genes were sub-cloned and inserted into an expression vector (pAH6307) containing a human IgG1 heavy chain leader/constant region under the control of human cytomegalovirus (CMV) promoter and ampicillin (Amp) and histidinol dehydrogenase (hisD) cassettes. The VL genes were inserted into an expression vector (pAN 6714) containing a human kappa light chain leader/constant region under the control of the human CMV promoter and neomycin phosphotransferase (neoR) cassette. Similarly, the chimeric JAA-F11 VH and VL were expressed and used as positive control in subsequent analyses.

Expression and Production of Humanized and Chimeric JAA-F11 Variants.

Co-Transfection into CHO-K1 Cells.

Adherent Chinese hamster ovary (CHO-K1; ATCC #CCL-61, Manassas, Va.) cells were cultured for 18 hours before transfection in Ham's F12 medium (Corning Cellgro, Manassas, Va.) supplemented with 10% fetal calf serum (FCS; Hyclone) at 37° C. and 5% carbon dioxide (CO2) in humidified air and harvested at 50-80% confluency. The mammalian 6307 pAH (VH) and 6714 pAN (VL) expression vectors were co-transfected into CHO-K1 cells by electroporation (Gene Pulser System (Bio-Rad, Hercules, Calif.). Briefly, each plasmid (VH and VL) was linearized using the PvuI restriction enzyme (Promega, Madison, Wis.) and 5 µg of each plasmid was added to 5×106 CHO-K1 cells in cold Ham's F12 medium (Corning Cellgro, Manassas, Va.) in a total volume of 500 µL in a 0.4 cm electroporation cuvette (Bio-Rad, Hercules, Calif.). The cuvette containing the mixture was electroporated at 960 µF and 250 mV. The transfection mixture was then diluted with pre-warmed non-selective medium (Ham's F12 supplemented with 10% FCS) to a concentration of 1×105 cells/mL. Two hundred microliters was then plated into 96-well tissue culture plate(s) (BD Bioscience, San Jose, Calif.) at a density of 1×10⁴ cells per well. The transfected cells were incubated at 37° C. and 5% CO2 in a tissue culture incubator. At 72 hours, the non-selective medium from 96-well tissue culture plate was removed and replaced with 200 µl of Ham's F12 (plus 10% FCS) selective medium containing 700 µg/ml G418 (Gibco, Life Technologies, Grand Island, N.Y.), 5 mM of histidinol (Sigma-Aldrich, St Louis, Mo.) and 10 mM of HEPES buffer (Corning Cellgro, Manassas, Va.) and colonies were allowed to grow for up to 3 weeks. CHO-K1 cells transfected with plasmids 6307 pAH and 6714 pAN will continue to grow, while untransfected CHO-K1 cells will not grow. Every 2-4 days for the next 14 to 21 days, the selective medium was replaced to remove debris of dead cells and colonies of resistant cells were allowed to grow in the selective medium.

Analysis of Culture Supernatants by Enzyme Linked Immunoassay (ELISA)

Between 14-21 days after selection, CHO-K1 culture supernatants from the 96-well plate(s) were collected and analyzed for antibody by enzyme-linked immunoassay (ELISA). Briefly, 100 µL of culture supernatants were added to Immulon 1 B-medium binding 96-well microtiter plate(s) (Thermo Scientific, Milford, Mass.) that had been coated with 1.25 µg/mL of TF-Ag-BSA conjugate in coating buffer (0.1 M Na2CO3 at pH 9.6) and washed five times with TBS-brij (pH 7.2). A 1:500 dilution of purified mouse JAA-F11 (1 mg/mL) in sterile PBS was also added into 2-3 wells on each plate to serve as positive controls. After a 2-hour incubation at 37° C., the plates were washed five times and 100 4, of anti-human IgG-Alkaline Phosphatase conjugate secondary antibody (Sigma-Aldrich, St Louis, Mo.) in 1% BSA-PBST buffer (1:10,000) was added into each well for transfected cells while a 1:1000 dilution of an anti-mouse IgG-Alkaline Phosphatase conjugate secondary antibody (Sigma-Aldrich, St Louis, Mo.) in 1% BSA-PBST buffer was used for the mouse JAA-F11 control well. After 1 hour incubation at room temperature, the plates were washed five times and then 100 4, of phosphatase substrate (p-nitrophenyl phosphate (pNPP)) (Sigma-Aldrich, St Louis, Mo.) was added to each well. Plates were read at 405 nm using a plate reader after an hour incubation at room temperature to screen for the presence of IgG antibodies to TF-Ag. As a blank, HAM's F12 (plus10% FCS) medium was used during the primary antibody incubation, followed by secondary antibody incubation and substrate incubation.

Generation of Stable Clones and Production

After the initial screening for anti-TF-Ag antibody at 14-21 days after selection started, 10-12 clones with the highest absorbance readings were selected and transferred into 24-well tissue culture plates for expansion. The culture supernatants from these clones were then analyzed by ELISA. The 4 clones that gave the highest absorbance readings were transferred to T25 tissue culture flasks, expanded and screened again for anti-TF-Ag antibody by ELISA to ensure that the clones were still producing antibodies reactive to TF-Ag. These 4 clones were then transferred to T75 tissue culture flasks, expanded, rescreened for anti-TF-Ag antibody and cells stored frozen in liquid nitrogen. The clone with the highest anti-TF-Ag result was then further expanded and passaged 2-3 times to ensure that the cell line is stable.

Stable individual cell clones for each hJAA-F11 heavy and light chain combination from the best clone obtained above were generated through subcloning by limiting dilution. Briefly, cells were grown to confluence in a T75 tissue culture flask, harvested and counted and seeded at a 0.3 cell/well dilution in each well of 96-well plates in the selective medium. The plates were examined carefully 7-10 days later under a microscope and wells that showed a single focus of cells were marked and monitored until enough density of growth was seen. Supernatants from these marked wells were tested for anti-TF-Ag antibody by ELISA. The 4 clones that gave the highest absorbance readings were expanded as described above for obtaining the parental clones. The sub-clone that gave the highest absorbance was expanded and used for production of supernatant in T200 Nunc™ cell culture Tripleflasks (Thermo Fisher Scientific, Inc.).

For production in the Tripleflasks culture flasks for each humanized variant JAA-F11, cells were cultured for 3 weeks before 1 liter of culture supernatant was harvested. The clone producing the chimeric JAA-F11 was processed the same way as the humanized JAA-F11 variants.

Purification of Humanized and Chimeric JAA-F11 Variants

Humanized and chimeric JAA-F11 variants supernatants were purified using Protein A-Sepharose® 4B, Fast Flow affinity column (Sigma-Aldrich, St Louis, Mo.). To prepare the Protein A column, a 1:1 suspension of resin in Buffer A (0.02 M NaH2PO4, 0.15 M NaCl, pH to 8.0) was poured into a column. After the column had settled, it was washed with 20 column volumes (CV) of buffer A. One liter of CHO-K1 cell culture supernatant was centrifuged at 3500 rpm for 30 minutes to clear dead cells or debris and then filtered. The filtered supernatant was loaded onto the Protein A column and allowed to drip by gravity at a flow rate of 1 mL/min. The column was then washed with 10 CV of buffer A. The antibody was eluted from the protein A column using 3 CV of buffer B (0.2 M Na2HPO4, 0.1 M Citric Acid, pH 3.9). The eluate was neutralized carefully with 0.1M NaOH to minimize the effect of low pH on the antibody. The Protein A column was re-equilibrated with 20-30 CV of buffer A and stored at 2-8° C. Each column was used up to five times for the same antibody. The purified antibody was dialyzed overnight at 4° C. (Slide-A-Lyzer Dialysis Cassette; Thermo Scientific) against either; 1× Phosphate Buffered Saline (PBS) or RPMI media with or without phenol red as required for subsequent assays. After dialysis, the antibody was filtered with a 0.22 µm filter (Corning) and protein concentration determined by a Bio-Rad protein assay as detailed below. The antibody was stored at 4° C. and checked for binding to TF-Ag using ELISA.

Bio-Rad Protein Assay

The antibody concentration was determined using the Bio-Rad Protein Assay which is based on the Bradford dye-binding method. Briefly, the dye reagent was diluted with distilled water at 1:4 ratio and filtered using Whatman filter paper #1. Serial dilutions of a known protein standard (1.44 mg/mL gamma globulin, Bio-Rad, Hercules, Calif.) and the humanized antibody sample were prepared using 1×PBS buffer. 10 µL of each standard and sample solution were placed in triplicates into wells of a microtiter plate. Two hundred microliters of the diluted dye reagent was then added to all wells using a multichannel pipette and mixed thoroughly by pipetting up and down without creating bubbles. The plate was incubated at room temperature for at least 5 minutes to 1 hour. Absorbance was then read at 595 nm on the plate reader (Bio-Tek Instruments).

Analysis of Chemical Specificity and Affinity of humanized and chimeric JAA-F11 antibodies Determination of Chemical Specificity The chemical specificity of the various hJAA-F11 constructs and the chimeric JAA-F11 was determined using the printed glycan array. This was compared to data obtained previously for mouse JAA-F11. The glycan array is an indirect immunofluorescent method, described on the Consortium for Functional Glycomics website. Each construct was analyzed for reactivity with 610 different glycans. Briefly, the printed array was incubated successively with the antibody, washed, and incubated with secondary antibody labeled with FITC. After washing, the image was read in a Perkin Elmer Microscanarray XL4000 and a tiff file image stored and image analysis was performed using Imagene V.6 image analysis software. The relative binding of each binding glycan was expressed and normalized to the binding of the original glycan TF-Ag. Comparison and statistical analysis of the relative binding abilities were performed using ANOVA.

Determination of Relative Affinity

The relative affinity binding of the hJAA-F11 to TF-Ag was analyzed using a competitive inhibition ELISA with the mouse JAA-F11 antibody and chimeric JAA-F11 antibody. Briefly, 3 µg/mL hJAA-F11 or chimeric JAA-F11 was incubated in the presence of different concentrations of mouse JAA-F11 (10, 8, 6, 4, 2 ug/mL) on 1.25 ug/mL TF-Ag coated 96-well plates (Thermo Scientific, Milford, Mass.). Bound antibody was detected by incubation with anti-human IgG secondary antibody and substrate and absorbance reading was obtained as described in these materials and methods. The amount of mouse antibody required to inhibit the binding of 3 µg/mL humanized or chimeric antibodies by 50% was determined and compared. The higher the amount of mouse antibody required for inhibition, the higher the relative affinity of the antibody. The relative affinity of each of the humanized antibodies and chimeric antibody was compared using ANOVA.

Analysis of Biological Efficacy of hJAA-F11

Assessment of Binding to Human Breast Tumor Cell Lines

Binding of hJAA-F11 to various human breast tumor cell lines was analyzed using whole cell ELISA. The TF-Ag bearing mouse mammary tumor 4T1 cell line served as a positive control while the P3-X63-Ag8 Myeloma (ATCC Number: CRL-1580) cell line which was the fusion partner for producing JAA F11 hybridoma served as the TF-antigen negative control. Positive binding was determined by comparing the reactivity of each antibody with each cell line to the reactivity of that antibody with the myeloma cell line using the student's T test. To standardize the data, binding to each cell line was expressed by dividing the absorbance reading of the test cell line by the absorbance reading of the myeloma cells.

Cell Preparation

The 4T1 breast tumor and myeloma cell lines were harvested using a non-enzymatic Cellstripper (Mediatech, Inc. VA, USA). To prevent clumping of cells, media, buffer and reagents were pre-warmed before using. For adherent cells, the media was removed from the culture vessels and the cells were rinsed with 1× Dulbecco's Phosphate Buffered Saline (DPBS) without calcium and magnesium (Mediatech Inc., Cellgro). Five milliliters of Cell Dissociation Solution was added to each flask and then incubated at 37° C. for 10 minutes. The flasks were tapped to dislodge the cells. For non-adherent myeloma cells, the flasks were tapped well and the culture supernatant was centrifuged at 1000×G for 10 mins. The cell pellets were resuspended in Cell Dissociation Solution and incubated at 37° C. for 10 mins. After incubation, 20 mL of 1×DPBS was added to the cells and pipetted repeatedly to remove clumps. The cell suspensions were then centrifuged at 1000×G for 10 minutes. The supernatants were decanted and the pellets resuspended in 5 mL DPBS. The cells were counted using trypan blue stain and a hemocytometer. The cells were diluted to obtain 1×10$^6$ viable cells/ml. Two hundred microliters of the cell suspensions (2×10$^5$ cells) were placed in 5 ml polystyrene tubes quadruplets. Two hundred microliters of 4% formaldehyde solution was added to each tube and incubated for 20 mins at room temperature before being centrifuged at 1500×G for 10 mins. The supernatant was decanted carefully in one throw, the cells were washed in DPBS followed by centrifugation and decanting. Two hundred microliters of PBS-tween 1% BSA (w/v) was added to each tube and stored at 4° C. overnight or up to two weeks.

Enzyme Immunoassay on Cells

Two hundred microliters of 50 μg/mL of the mouse JAA-F11, hJAA-F11 or chimeric JAA-F11 antibody was added to tubes containing the different cell lines tested in quadruplet and incubated at 37° C. for two hours. One set of tubes treated with 200 μL of 1×PBS-0.1% Tween 20-1% BSA served as the negative control for each cell line tested. The tubes were washed three times with 3 mL of wash buffer (1×PBS Tween, no azide), then centrifuged for 10 minutes at 1500×G. The supernatant was carefully decanted between each wash. Two hundred microliters of anti-mouse IgG (γ-chain-specific) horseradish peroxidase secondary antibody (1:1000, Sigma-Aldrich, St. Louis, Mo.) or anti-human IgG (γ-chain-specific) horseradish peroxidase secondary antibody (1:2000, Sigma Aldrich, St. Louis, Mo.) in PBS-Tween-1% BSA was added to respective tubes and then incubated for 1 hour at room temperature (RT). After incubation, the tubes were decanted and washed three times, and centrifuged at 1500×G between washes. Two hundred microliters of 0-phenylenediamine dihydrochloride substrate (OPD; Sigma, St. Louis, Mo.) solution was then added to each tube and incubated for 1 hour at room temperature. After incubation, the reaction was stopped by adding 100 μL of stop solution (1N H2SO4) and centrifuged for 10 minutes at 1500×G. Next, 200 μL of supernatant was removed from each tube and transferred to respective wells in a microtiter plate. Absorbance was read at 490 nm using the microplate reader (Microplate Autoreader, Model EL311, Bio-Tek Instruments, Inc.) and unreacted OPD substrate was used as blank. For the different cell lines, each respective average blank (tubes with only PBS-Tween-1% BSA) was deducted from their respective average OD to get the final optical reading. Each experiment was repeated 3 times.

Effects of hJAA-F11 on Cancer Cell Proliferation In Vitro

To examine the effects of the humanized and chimeric JAA-F11 antibodies on cancer cell growth, in vitro 3[4,5-dimethylthiazol-2-yl]-2,5-diphenyltetrazoliumbromide (thiazoyl blue, MTT) proliferation analyses were performed. 4T1 mouse breast tumor cells and human breast tumor cells were seeded at 1×10$^4$ cells/well in 10 replicates in 96-well plates in the presence of varying amounts of JAA-F11, humanized and chimeric JAA-F11 (4, 2, and 1 μg/mL). When plated at this cell density, the cells are in the linear portion of their growth curves at 72 hours. Cells grown in culture medium without antibodies served as normal growth controls. Culture medium alone was used a blank. After 68 hours of cell growth at 37° C., 10 μL of the tetrazolium salt MTT (5 mg/ml) was added to each well, and the plates were returned to the incubator for another 4 hours. At the end of incubation, the resulting formazan product in each well was solubilized by adding 120 μL of dimethyl sulfoxide (DMSO, Fisher Scientific), and the absorbance of each well was then measured at 570 nm (MicroplateAutoreader, Model EL311, Bio-Tek Instruments, Inc.).

Antibody-Dependent Cellular Cytotoxicity Assay

To examine the effector functions of the hJAA-F11 antibodies, antibody-dependent cellular cytotoxicity (ADCC) and complement-dependent cytotoxicity (CDC) analyses were performed.

ADCC was determined by the lactate dehydrogenase (LDH) release assay (CytoTox 96 Non-Radioactive Cytotoxicity assay; Promega, Madison, Wis.) using human peripheral blood mononuclear cells (PBMC) as effector cells and human breast tumor cell lines as target cells at an effector to target (E:T) ratio of 100:1.

The PBMCs were prepared from whole blood by density gradient centrifugation using Ficoll-Paque. Whole blood collected in purple-top EDTA vacutainers was mixed with an equal volume of pre-warmed sterile DPBS. Twenty milliliters of diluted blood was then gently layered onto 15 mL of Ficoll-Paque Plus (GE Healthcare) in 50 mL conical tubes. The samples were centrifuged at 1300 rpm for 30-40 min at room temperature with no brake. Next, the PBMC layer was collected and sterile PBS was added to the PBMCs for a total volume of 40 mL. The mixture was then centrifuged at 1000 rpm for 10 min at 18° to 22° C. to remove any contaminating Ficoll and platelets/plasma proteins. The supernatant was discarded, the cells were resuspended in fresh sterile PBS, and the centrifugation step was repeated. The cells were resuspended in RPMI 1640 culture media (10% FCS) and counted using hemocytometer and trypan blue.

Target cells (1×10$^4$; 30 μl) and PBMCs (1×10$^6$; 30 μl) were added into 96-well U-bottomed plates and incubated with hJAA-F11 or chimeric antibodies (200 μg/mL; 30 μL) for 17 hours at 37° C. in a tissue culture incubator. Forty-five minutes before completion of the 17 hours incubation, 10 μL of lysis solution (×10) was added to the wells containing the target cell maximum LDH release control (target cells and medium) and the volume correction control (medium alone). At the end of incubation, the plate was centrifuged for 4 minutes at 1000 rpm. Fifty microliters aliquots were then transferred from all wells to a fresh flat-bottomed 96-well plate. Next, 50 μL of reconstituted substrate mix was added to each of these wells. The plate was covered with foil and incubated for 30 minutes at room temperature. The reaction was stopped with the addition of 50 μL of stop solution to each well, and absorbance was recorded at 490 nm using a microplate reader (MicroplateAutoreader, Model EL311, Bio-Tek Instruments, Inc.). Cytotoxicity was calculated using the formula:

$$\text{Cytotoxicity (\%)} = 100 \times [(E-SE)]/[(M-SE)],$$

where for each condition the absorbance of the substrate is measured. The conditions are as follows; E is the experimental well, SE is the spontaneous release without the antibody control (target cells incubated with effector cells and PBS), M is the maximum release determined by the target cells lysed with 10× lysis solution.

Complement Dependent Cytotoxicity (CDC) Assay

CDC was determined by the lactate dehydrogenase (LDH) release assay (CytoTox 96 Non-Radioactive Cytotoxicity assay; Promega, Madison, Wis.) using HCC 1428 breast tumor cells (ATCC® CRL-2327, Manassas, Va.) as the target cell population. A LDH positive sample that contains bovine heart LDH, provided with the reagent kit was used as a positive control. After comparing rabbit, baby rabbit and guinea pig complement for background levels of cytotoxicity, lyophilized guinea pig serum (CL3112, Cedarlane Laboratories, Burlington, N.C.) was used as the source of the complement and reconstituted as per manufacturer's instructions. The optimal cell concentration used in the assay was 1×104 cells/50 µL per well. The antibodies used were dialyzed against phenol red free-RPMI media. For experimental wells, 50 µl of HCC 1428 cell suspension, 20 µl of complement dilution (final dilution at 1:20), and 30 µL of antibody (final concentration at 100 µg/ml) were mixed in each well in quadruplicate sets in a round-bottom 96-well culture plate. Included were control wells containing target cells and complement without antibody to control for any cytotoxicity mediated by the serum used as the complement source and the spontaneous release of LDH. The plate was centrifuged at 1000 rpm for 4 minutes and then incubated for 2 hours at 37° C. with 5% carbon dioxide. Forty-five minutes before completion of the 2 hour incubation, 10 µl, of lysis solution (×10) was added to the wells containing the target cell maximum LDH release control and the volume correction control.

At the end of incubation, the plate was centrifuged for 4 minutes at 1000 rpm. Fifty microliters aliquots were then transferred from all wells to a fresh flat-bottomed 96-well plate. Next, 50 µL of reconstituted substrate mix was added to each well. The plate was covered with foil and incubated for 30 minutes at room temperature. The reaction was stopped with the addition of 50 µl of stop solution to each well, and absorbance was then recorded at 490 nm using a microplate reader (MicroplateAutoreader, Model EL311, Bio-Tek Instruments, Inc.). Cytotoxicity was calculated using the formula:

$$\text{cytotoxicity (\%)} = 100 \times [(E-SE)]/[(M-SE)],$$

where for each condition the absorbance of the substrate is measured. The conditions are as follows; E is the absorbance of the experimental well, SE is the spontaneous release with complement but without the antibody (target cells incubated with complement and media), and M is that of target cells lysed with 10× lysis solution.

Cell Internalization Assays

Internalization of humanized and chimeric JAA-F11 into 4T1 breast tumor cells was analyzed by two methods, an enzyme immunoassay with surface binding measured at 2 temperatures of incubation, 4° C. and 37° C., and an immunofluorescent microscopy method.

Enzyme Immunoassay Method of Internalization

The mouse 4T1 breast cancer cell line was tested for internalization of JAA-F11, hJAA-F11 or chimeric JAA-F11. Five hundred thousand (5×105) cells were seeded in all six wells of a 6-well plate and were grown to confluence. For each antibody tested, two plates were prepared. Media was removed from each plate and 1 mL of antibody (200 µg/mL) was added to 3 wells of each plate, and 1 mL of PBS dilution was added to the remaining 3 wells. One set of plates was incubated at 37° C. to allow internalization and the other plate was incubated at 4° C. After the 1 hour incubation, media was removed and the wells were washed 4 times with 1 mL of Phenol Red Free RPMI media. Next, 1 mL of 2% paraformaldehyde was added to each well and the plates were incubated at room temperature for 20 minutes to fix the cells. The plates were then washed 4 times with Phenol Red Free RPMI media. Next, one mL of anti-mouse or anti-human IgG (γ-chain-specific) alkaline phosphatase secondary antibody (1:5000, Sigma, St. Louis, Mo.) in 1% BSA/PBS was added and the plates were incubated at 37° C. for 1 hour. The plates were then washed 4 times with Phenol Red Free RPMI media and 1 mL of p-nitrophenyl phosphate substrate (pNPP) was added and incubated for 1 hour in the dark. After the 1 hr incubation, 200 µL from each well was transferred to respective wells of a 96-well plate and absorbance was recorded at 405 nm using a microplate reader (MicroplateAutoreader, Model EL311, Bio-Tek Instruments, Inc.). Unreacted substrate was used as a blank. The triplicate wells were averaged, the average optical density of the media alone blank was subtracted from the wells containing antibody. Percent internalization was calculated using the formula:

$$\% \text{ internalization} = 100 \times [1-(37° \text{ C. sample} - 37° \text{ C. blank})/(4° \text{ C. sample} - 4° \text{ C. blank})]$$

Immunofluorescent Microscopy Method

In this method, 4T1 breast cancer cells were seeded on coverslips in the wells of two 6-well tissue culture plates at a density of 3×105 cells in 10% FCS RPMI 1640 media and incubated at 37° C. and 5% CO2 for 24 hours. Media was removed from the plates and 1.5 mL of test antibodies (5 µg/mL) diluted in serum-free RPMI 1640 media was added to respective wells. Both plates were placed at 4° C. for 20 minutes to allow for surface binding of antibodies. After the 20 minute incubation, the coverslips were transferred from one of the plates into a new 6-well plate. Antibody dilutions were removed from the second plate and pre-warmed serum-free RPMI 1640 media was added and the plate was incubated at 37° C. for 1 hour in a tissue culture incubator. The coverslips from the first plate were washed twice with ice-cold 5% BSA/PBS, rinsed once with 1×PBS and were then fixed with 4% paraformaldehyde solution (Affymetrix) for 15 min at room temperature. After the 1 hour incubation at 37° C., coverslips from the second plate were transferred to a new 6-well plate, washed, rinsed and fixed.

Following three washes in 1×PBS, cells in both plates were permeabilized with 0.1% Triton X-100, 0.1% sodium deoxycholate in PBS for 10 min at room temperature. Next, cells were rinsed three times with 1×PBS and then incubated in 5% BSA/PBS for 30 minutes at room temperature. Coverslips were then incubated with rabbit anti-lysosomal membrane protein 1 (LAMP1; Abcam, 24170) antibody at dilutions of 1 µg/mL in 5% BSA/PBS for 1 hour at room temperature. Coverslips were then rinsed three times with 1×PBS and incubated with anti-mouse IgG-Alexa 647 and anti-rabbit IgG Alexa 488 (mouse JAA-F11 coverslips) and anti-human IgG-Alexa 647 and anti-rabbit IgG Alexa 488 (chimeric and hJAA-F11) secondary antibodies (Molecular Probes, Invitrogen), at a dilution of 1:500 in 5% BSA/PBS. The anti-rabbit IgG Alexa 488 secondary antibody was used to detect the anti-LAMP 1 antibody. The coverslips were incubated for 1 hour at room temperature in the dark. Following incubation, cells were rinsed three times with 1×PBS in the dark. Coverslips were placed with cells facing down on Slowfade Gold reagent (Molecular Probes, Life Technologies) with DAPI media on microscopic slides and sealed with nail polish. Cells were analyzed with AxioImager fluorescence microscope (Zeiss). Images were captured and analyzed using AxioVision Release 4.8.2 software.

In Vivo Studies to Test the Efficacy of Humanized JAA-F11 to Detect TF-Ag Bearing Breast Tumors Using the H2L2 humanized JAA-F11 antibody obtained from the above in vitro biological studies, immunolocalization studies were performed in mice to test whether iodine-124 labeled humanized antibody will localize to TF-Ag breast tumors in the mice.

[124]Iodine Labeling of hJAA-F11 (H2L2) Antibody

[124]Iodine labeling of the humanized JAA-F11 antibody was carried out using the Bolton Hunter method. Before iodination, the humanized antibody was first modified using a water-soluble Bolton Hunter reagent (Sulfo-SHPP) (Thermo Scientific, Rockford Ill., USA). Briefly, 1.9 mg of hJAA-F11 antibody was dissolved in Modification Buffer (200 mM borate buffer, pH 9.0). Five mg of the water-soluble Bolton Hunter reagent was dissolved in 1 mL Modification Buffer immediately before use. A 100 µL of the water-soluble Bolton Hunter reagent solution was then added to the antibody sample and incubated on ice for 3 hours with periodic mixing. Non-reacted water soluble Bolton Hunter reagent was removed by dialyzing against phosphate-buffered saline (PBS: 0.1 M sodium phosphate, 150 mM sodium chloride). At this intermediate step the humanized antibody contains a linker attached to some of the lysines of the antibody, and it is stable for 2 weeks.

The modified hJAA-F11 antibody was then labeled using the Chizzonite indirect labeling method [158]. Briefly, a Pierce pre-coated iodination tube (Thermo Fisher, Rockford, Ill., USA) was prewetted with 1 mL of High Tris Iodination buffer (0.125 M Tris-HCl, pH 6.8, 0.15 M NaCl. The buffer was decanted and then 100 µL of HighTris Iodination Buffer was added directly to the bottom of the tube, followed by the addition of 280 µL of (4.59 milliCurie) of sodium 124I iodide in 0.02 M NaOH solution (IBA Molecular, Richmond, Va.). An initial count was taken using a radioisotope calibrator CRC 12 (Capintec). The pH of the mixture was measured to ensure that it was at pH 7, neutral. After 6 minutes activation at room temperature, the activated iodide was added to the previously modified huJAA-F11 solution. After a 9 minutes incubation period, 50 µL of Scavenging Buffer (10 mg tyrosine/mL in Tris Iodination Buffer; 25 mM Tris, pH 7.5, 0.4 M NaCl) and the mixture was incubated for 5 minutes. The purpose of the scavenging buffer is to remove free iodine that reacts with the tyrosine in the buffer.

A 1 mL of Tris/NaCl/EDTA buffer (25 mM Tris-HCl, pH 7.5, 0.4 M NaCl, 5 mM EDTA, 0.05% sodium azide) was then added to the reaction mixture. The sample was then added to a 10 mL desalting column that has been pre-equilibrated with Tris/NaCl/EDTA buffer. The sample tube was washed with 0.5 mL Tris/NaCl/EDTA buffer and the wash added to the column. The sample was eluted in fifteen fractions of 500 µL each using Tris/NaCl/EDTA buffer, and was tested for radioactivity. Radiolabelling efficiency was determined on the fraction with the highest activity by high performance liquid chromatography (HPLC). The radiolabeled antibody was injected into the animals within 2 hours of labeling. To ensure that the labeled humanized JAA-F11 maintains its TF-Ag reactivity, a radioimmunoassay was also carried out.

Animals and Tumor Models

Animals in this study were housed and utilized in accordance with the Institutional Animal Care and Use Committees (IACUC) regulations. All protocols were approved by the IACUC of the University at Buffalo. 4T1 mouse breast cancer cells were implanted in 7-8 weeks old female Balb/C mice by injecting 5×104 cells in 0.1 mL D-PBS subcutaneously under one of the right nipples. The mice were divided into 2 groups and injected with [124I]-hJAA-F11 (n=13) and free 124I124 (n=7) 10-14 days after tumor implantation by tail vein and then subjected to biodistribution studies and micro-PET imaging. One mouse from each of the 2 groups were imaged and followed throughout the study. All mice received 0.2 g/L potassium iodide water after injection with labeled antibody and throughout the whole study as a thyroid-blocking regime.

Biodistribution Studies

Mice were sacrificed by injecting 0.1 mL Sodium Pentobarbital (Fatal Plus) intraperitoneally at 72, 96, 168, and 192 hours after injection of the radiolabeled antibody. At each time point, three mice that received the labeled antibody and two mice with free iodine were sacrificed. Blood, muscle, spleen, lungs, kidneys, heart, liver, small and large intestines, stomach, brain, skin, tumor tissue, bone, tail, esophagus, thyroid and ovaries were harvested and placed into pre-weighed 5 ml polypropylene tubes. These tubes were re-weighed to obtain actual weight of each tissue/organ. All the tubes were capped and radioactivity was measured using a gamma counter. Radioactivity uptake for each tissue was calculated as the percentage of the injected dose per gram of tissue (% ID/g).

Micro-PET Imaging

Localization of the labeled antibody in one mouse each from the two groups was determined through microPET imaging using the microPET camera, Focus 120® (Siemens Concorde Microsystems) at 24, 48, 72, 96, 168, and 192 hours after injection using known techniques. Briefly, before scanning, mice were anesthetized with 02/isoflurane (1%-3% isoflurane) and then imaged in the prone position in the gantry of the microPET scanner. The emission scan window was set between 350 and 750 keV. The scan was performed for 30 minutes for each mouse.

Radioimmunoassay

To determine the immunoreactivity of the radiolabeled antibody, a radioimmunoassay (MA) was performed. A microtiter plate was coated with 100 µL of 1.25 µg/mL TF-Ag-BSA conjugate in coating buffer. The buffer was removed from the wells and washed with 1% BSA/PBS-Tween. One hundred microliters of serial dilutions of radiolabeled hJAA-F11 in 1% BSA/PBS-Tween were added to the wells and allowed to bind at room temperature for 1 hour. After incubation, the unbound antibody was removed by washing the wells with 1% BSA/PBS-Tween three times manually using a multi-channel pipette. The bound hJAA-F11 was removed from the plate by incubating with 200 µL of 1M Acetic acid/0.15M NaCl buffer (pH 2.4) for 30 minutes at room temperature. After the incubation, 100 µL solution from each well was added into separate polypropylene test tubes and the radioactivity was measured using a gamma counter.

Example 3

This Example provides additional analysis and characterization of mAbs of this disclosure.

Figure 11:
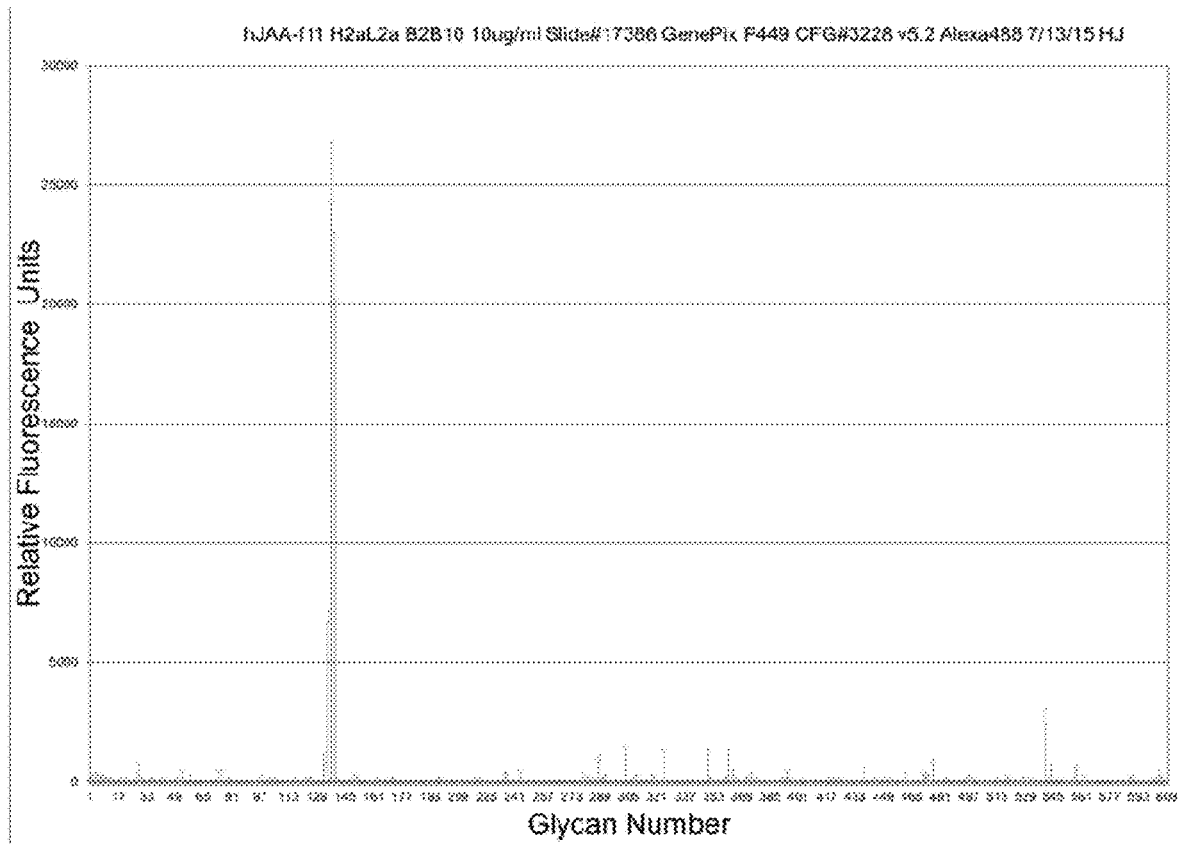
FIG. 11. Binding of H2aL2a (A), chimeric (B) and mouse JAA-F11 (C) antibodies on a Consortium for Functional Gylcomics (CFG) glycan array at 10 µg/ml. The arrays contained 610 glycans. Only TF-Ag and 2 related saccharides (A, B) or 3 related saccharides (C) (not present on normal tissue) bound to the antibodies at higher than 15% of the TF-Ag binding. The glycan list is provided in Table 9.
Figure 11:
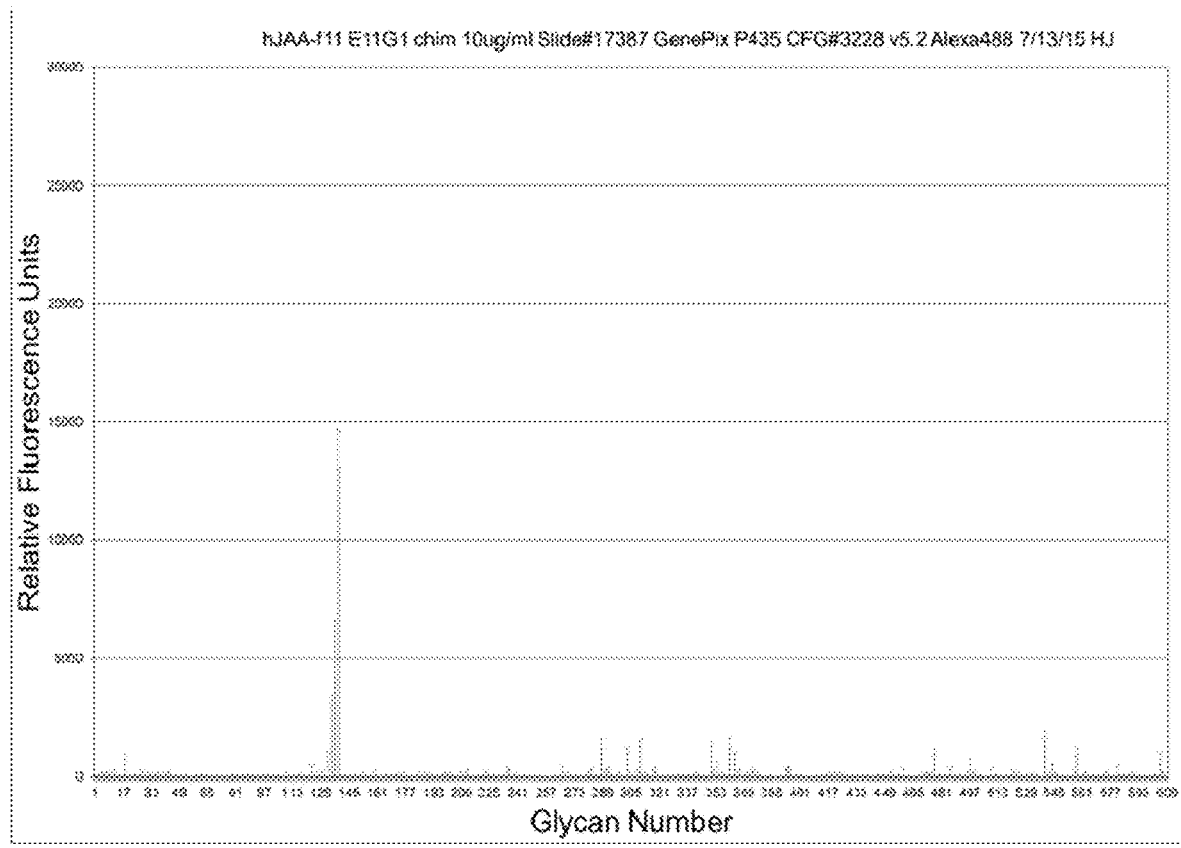
Figure 11:
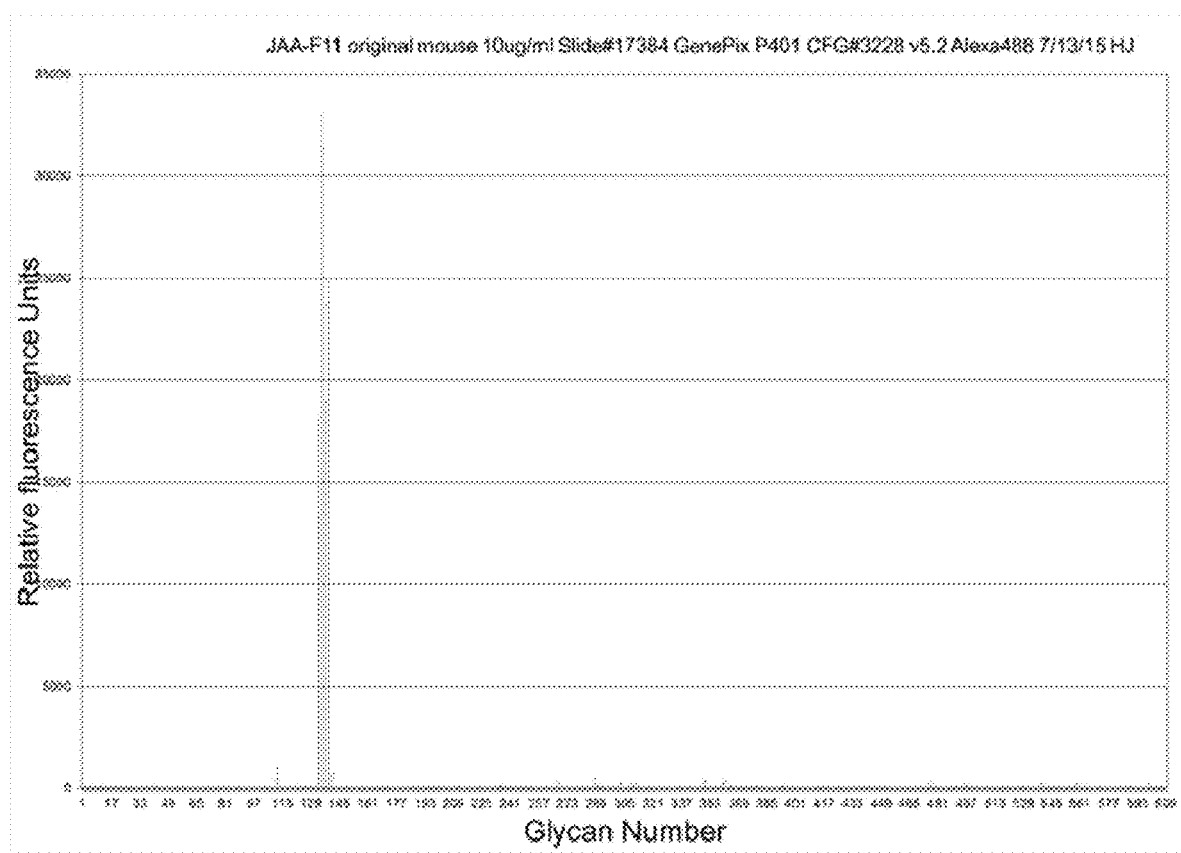

FIGS. 11A, 11B, 11C show glycan array binding of H2aL2a, chimeric and mouse JAA-F11. In particular, FIGS. 11A, 11B and 11C provide data representing binding of H2aL2a (FIG. 11A), chimeric (FIG. 11B) and mouse JAA-F11 (FIG. 11C) antibodies on a Consortium for Functional Gylcomics (CFG) glycan array at 10 µg/ml. The arrays contained 610 glycans. Only TF-Ag and 2 related saccharides (FIG. 11A, FIG. 11B) or 3 related saccharides (11C) (not on normal tissue) bound to the antibodies at higher than 15% of the TF-Ag binding. Thus, these data confirm that H2aL2a does not detectably bind to glycans present on normal tissues, and thus is at least as specific as the chimeric mAb. The glycan list is provided in Table 9.

Figure 12:
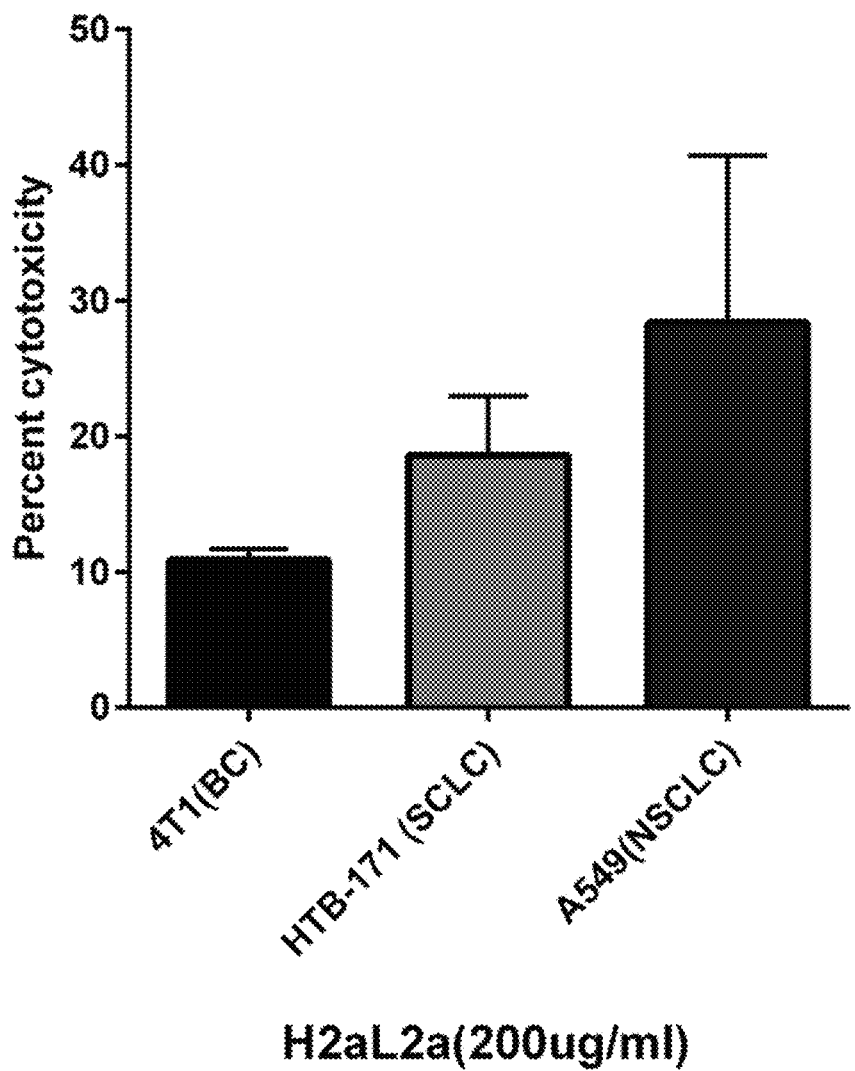
FIG. 12. ADCC activity of H2aL2a antibody in a TF-Ag positive breast (4T1) and two lung cancer (HRB-171 and A549) cell lines. ADCC was assessed by lactate dehydrogenase (LDH) release after incubation with 200 µg/mL of humanized JAA-F11 and fresh human PBMCs at effector to target cell (E:T) ratio of 100:1. Data are representative of results obtained using 2 blood donors and are presented as percent (%) cell lysis in antibody treated cells compared to cells treated with lysis buffer (100%) alone. Bars represent mean±S.E. (n≥3 independent experiments). *P<0.05

FIG. 12 represents ADCC activity of H2aL2a on three different cancer cell lines. In particular, FIG. 12 provides data showing ADCC activity of the H2aL2a antibody in a TF-Ag positive breast (4T1) and two lung cancer (HRB-171 and A549) cell lines. ADCC was assessed by lactate dehydrogenase (LDH) release after incubation with 200 μg/mL of humanized JAA-F11 and fresh human PBMCs at effector to target cell (E:T) ratio of 100:1. Data are representative of results obtained using 2 blood donors and are presented as percent (%) cell lysis in antibody treated cells compared to cells treated with lysis buffer (100%) alone. Bars represent mean±S.E. (n≥3 independent experiments). *P<0.05.

Figure 13:
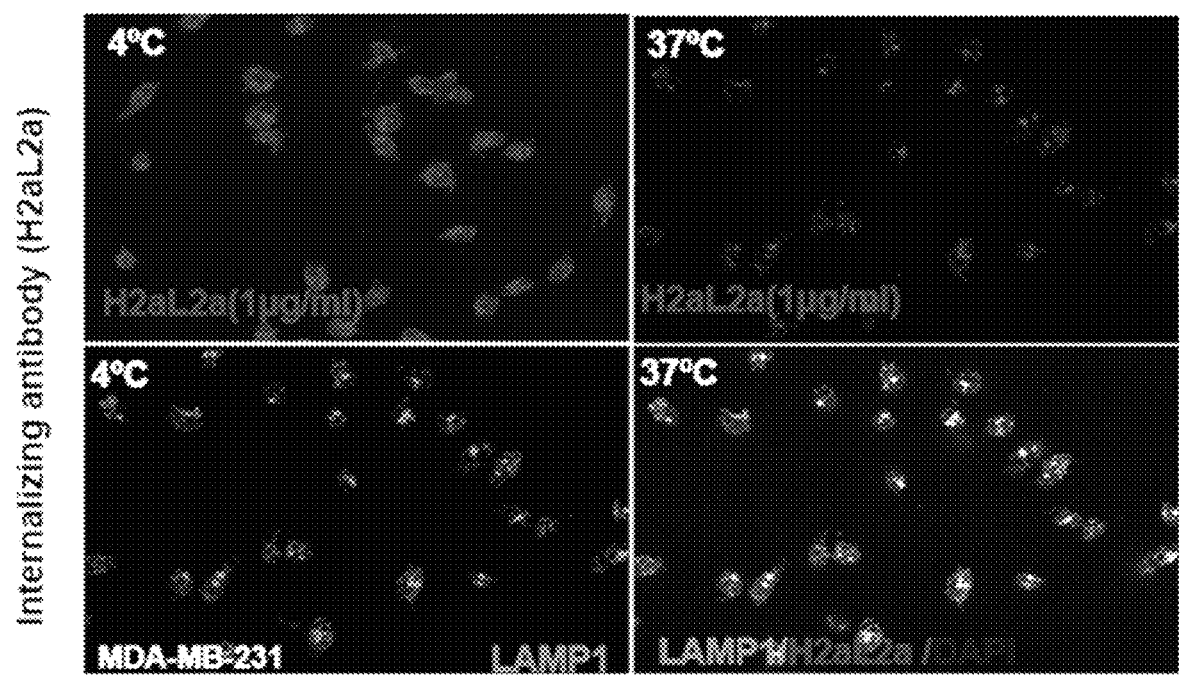
FIG. 13. Internalization of H3L3, H2L3, and H2aL2a hJAA-F11 antibodies in a TF-Ag positive, triple negative human breast cancer cell line (MDA-MB-231). A) Internalization by EIA detection of antibody surface binding following incubation of cells with antibody in 4° C. (no internalization) and 37° C. degrees (internalization). H2aL2a antibody showed significant internalization (p<0.05). Bars represent mean±S.E. (n=3 experiments). B) Comparison of internalization abilities of three humanized antibodies H3L3, H2L3 and H2aL2a. Assay performed as in A). C) Representative images showing immunofluorescent staining of H2aL2a and H3L3 (red) and the lysosomal protein marker, LAMP-1 (green). In the top panels MDA-MB-231 cells were pre-incubated with antibodies (1 ug/mL) for 20 min at 4° C. Lower panels show images after at incubation at 37° C. for 60 min. Images confirm internalization of H2aL2a (above panel) indicated by co-localization in merged images (arrows). Total magnification was ×40. Images are representative of 3 independent experiments.

FIG. 13 provides evidence of internalization of H3L3, H2L3, and H2aL2a hJAA-F11 antibodies in a TF-Ag positive, triple negative human breast cancer cell line (MDA-MB-231). FIG. 13A) Internalization by EIA detection of antibody surface binding following incubation of cells with antibody in 4° C. (no internalization) and 37° C. degrees (internalization). H2aL2a antibody showed significant internalization (p<0.05). Bars represent mean±S.E. (n=3 experiments). FIG. 13B) Comparison of internalization abilities of three humanized antibodies H3L3, H2L3 and H2aL2a. Assay performed as in A. FIG. 13C) Representative images showing immunofluorescent staining of H2aL2a and H3L3 (red) and the lysosomal protein marker, LAMP-1 (green). In the top panels MDA-MB-231 cells were pre-incubated with antibodies (1 ug/mL) for 20 min at 4° C. Lower panels show images after at incubation at 37° C. for 60 min. Images confirm internalization of H2aL2a (above panel) indicated by co-localization in merged images (arrows). Total magnification was ×40. Images are representative of 3 independent experiments.

Figure 14:
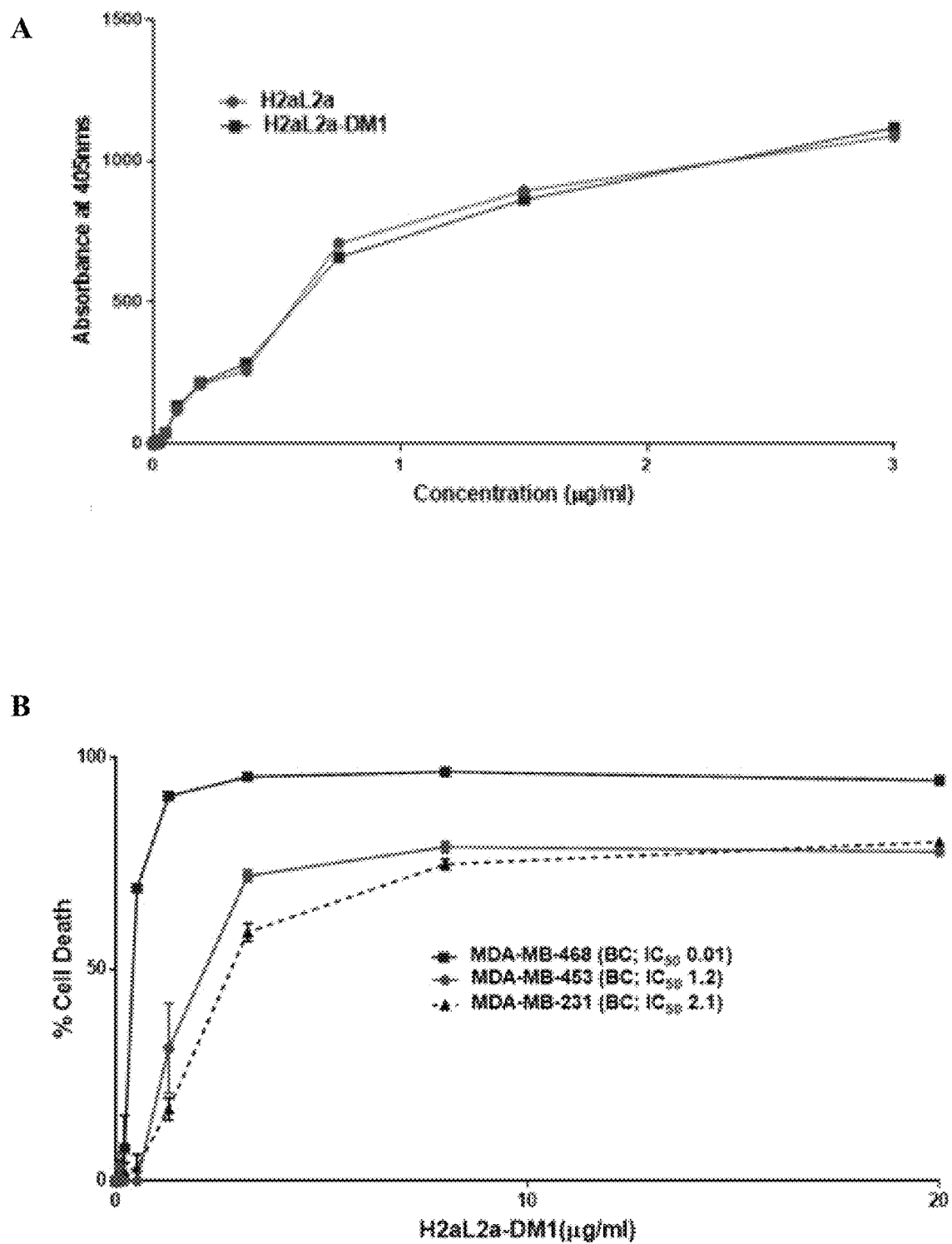
FIG. 14. In vitro Cytotoxicity of H2aL2a-DM1 in breast and lung cancer cells. A) Graph shows nearly identical relative binding of hJAA-F11 and hJAA-F11-DM1 to TF-Ag as determined by ELISA. 3 µg of each antibody was serially diluted and binding to the TF-Ag coated plate was measured by using a species-specific alkaline phosphatase anti-human IgG antibody. B) & C) Relative cytotoxicity of DM1 conjugated hJAA-F11 antibody in several TF-Ag positive (B) breast and (C) lung (SCLC; NSCLC) cancer cell lines. Both shown at day 5 of treatment (IC50 values, µg/mL DM1).
Figure 14:
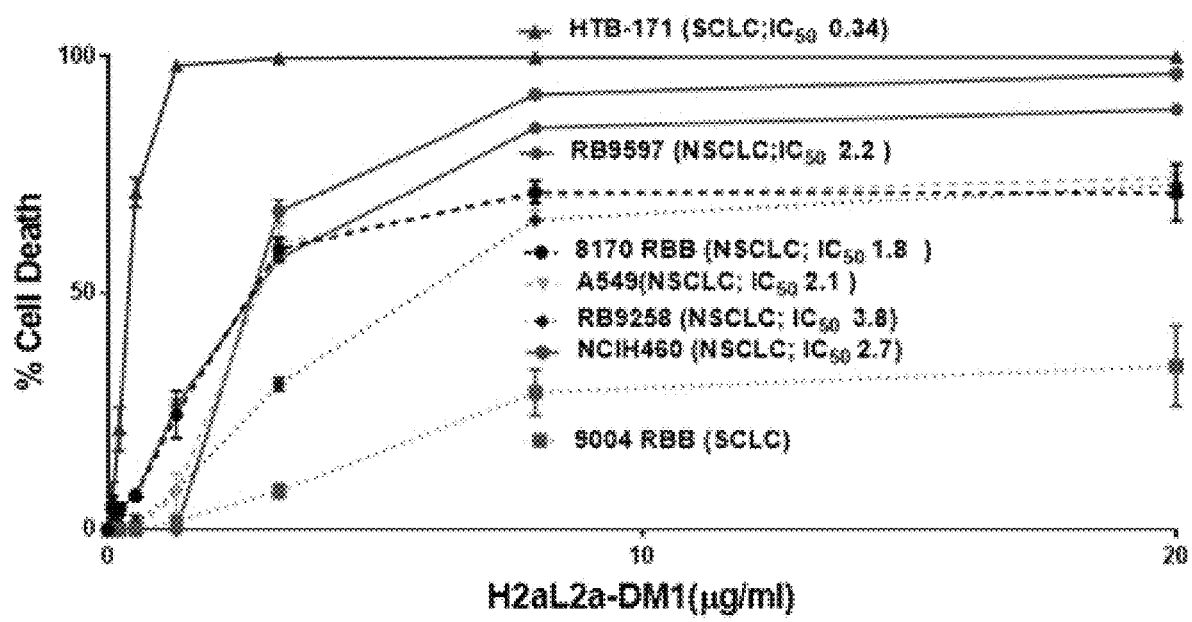

FIG. 14 provides data showing in vitro cytotoxicity of H2aL2a-DM1, a drug conjugate with H2aL2a, in breast and lung cancer cells. FIG. 14A) Graph shows nearly identical relative binding of hJAA-F11 and hJAA-F11-DM1 to TF-Ag as determined by ELISA. 3 μg of each antibody was serially diluted and binding to the TF-Ag coated plate was measured by using a species-specific alkaline phosphatase anti-human IgG antibody. FIG. 14B) & FIG. 14C) Relative cytotoxicity of DM1 conjugated hJAA-F11 antibody in several TF-Ag positive (1 FIG. 4B) breast and (FIG. 14C) lung (SCLC; NSCLC) cancer cell lines. Both shown at day 5 of treatment (IC50 values, μg/mL DM1).

FIG. 15 provides data showing efficacy of H2aL2a conjugated DM1 in a SCID mouse xenograft triple negative breast tumor model. In particular, in vivo activity of H2aL2a-DM1 conjugate, a drug conjugate with H2aL2a in a SCID/MDA-MB-231 (triple negative) xenograft model is shown. FIG. 15A) 10×10$^6$ MDA-MB 231 cells were injected into female SCID mice intra-mammary gland on day 0. Antibody treatments began on day 1 and included i.p. injection of PBS, naked hJAA-F11 (15 mg/Kg), hJAA-F11 (30 mg/Kg), hJAA-F11-DM1 (15 mg/Kg). Arrows indicate injection days (n=8 mice per group). Tumor growth was monitored for 50 days. ANOVA Analysis of PBS versus hJAA-F11-DM1,  p=0.0072, **p<0.0001. FIG. 15B) Bar graphs representing the mean tumor weights±S.E in the control and antibody treatment groups. Tumors were removed and weighed on day 50. * Unpaired t test was used to analyze the PBS control versus hJAA-F11-DM1. hJAA-F11-DM1 significantly reduces mean tumor weight at day 50.

Figure 16:
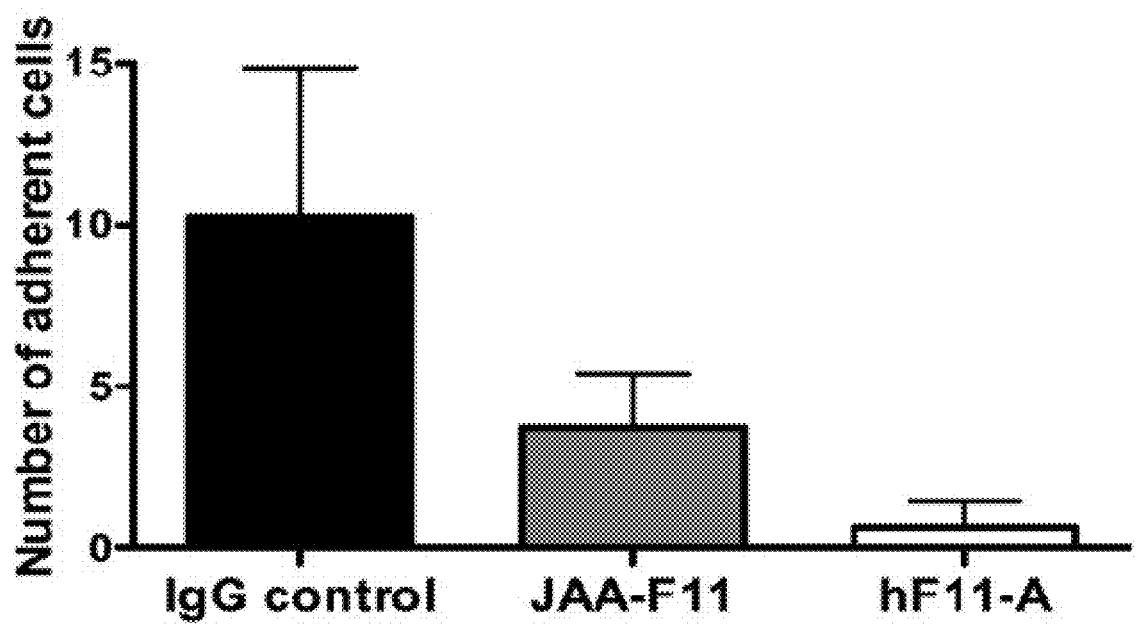

FIG. 16 shows data in an in vitro metastasis model showing mouse JAA-F11 and hJAA-F11 H2aL2a inhibition of tumor cell adhesion. The adhesion of MDA-MB-231 cells to primary human pulmonary microvascular endothelial cells (HPMEC, ScienCell Research Laboratories, Carlsbad, Calif.) was studied in an in vitro parallel plate laminar flow chamber with control immunoglobulin or with mouse JAA-F11 or H2aL2a.

Table 7 summarizes data for immunogenicity scoring of H2aL2a and chimeric JAA-F11 ("chimeric"). Assessment of immunogenicity of the H2aL2a constructs by using the scoring system developed by Gao et al [2013]. T20 score is used to measure "humanness" of monoclonal antibody variable region sequences; T20 score >80 for FR and CDR sequences is not immunogenic in humans; T20 score >85 for FR sequences only is not immunogenic in humans. FR=framework; CDR=complementarity determining region. H2aL2a is not immunogenic while chimeric is predicted to be immunogenic.

TABLE 7

| JAA-F11 Variants | T20-score (FR & CDR) | | T20-score (FR) | |
|---|---|---|---|---|
| | Heavy Chain | Light Chain | Heavy Chain | Light Chain |
| Chimeric | 67 | 78 | 72 | 86 |
| hJAA-F11 | 80 | 83 | 93 | 95 |

Table 8 provides data showing four TF-Ag related structures on normal tissues which do not react with hJAA-F11. In particular, the glycan array data showed that the humanized hJAA-F11-A and chimeric JAA-F11 antibodies do not bind either Galβ1-3GalNAc-beta (β) linked structures or common elongation structures on normal tissues. The values in the H2aL2a and Chimeric columns of Table 8 are relative fluorescence units (RFU) and are taken from the Glycan array binding FIGS. 11A, B and C. Units in Table 8 show only background RFUs. The linker connects the glycans to the array; linkers are also presented in the list of glycans of Table 9.

TABLE 8

| Glycan # on array | Glycan Structure | Linker | H2aL2a | Chimeric |
|---|---|---|---|---|
| [a]144 | Galβ1-3GalNAcβ1-4(Neu5Acα2-3)Galβ1 4Glcβ- | Sp0 | 112 | 8 |
| [b]145 | Galβ1-3GalNAcβ1-4Galβ1-4Glcβ- | Sp8 | 28 | 5 |
| [c]88 | GlcNAcβ1-3Galβ1-3GalNAcα- | Sp8 | 149 | 4 |
| [d]223 | Neu5Acα2-3Galβ1-3GalNAcα- | Sp8 | 157 | 2 |

[a]Glycan # 144 is ceramide ganglioside GM1 found on brain and red blood cells.
[b]Glycan #145 is ceramide asialo-GM1 found on NK cells, kidneys, spleen, and regenerating respiratory epithelial cells).
[c,d]Glycans # 88 and #223 are common elongation structures on normal tissues.

TABLE 9

| Chart Number | |
|---|---|
| 1 | Gala-Sp8 |
| 2 | Glca-Sp8 |
| 3 | Mana-Sp8 |
| 4 | GalNAca-Sp8 |

TABLE 9-continued

| Chart Number | |
|---|---|
| 5 | GalNAca-Sp15 |
| 6 | Fuca-Sp8 |
| 7 | Fuca-Sp9 |
| 8 | Rhaa-Sp8 |
| 9 | Neu5Aca-Sp8 |
| 10 | Neu5Aca-Sp11 |
| 11 | Neu5Acb-Sp8 |
| 12 | Galb-Sp8 |
| 13 | Glcb-Sp8 |
| 14 | Manb-Sp8 |
| 15 | GalNAcb-Sp8 |
| 16 | GlcNAcb-Sp0 |
| 17 | GlcNAcb-Sp8 |
| 18 | GlcN(Gc)b-Sp8 |
| 19 | Galb1-4GlcNAcb1-6(Galb1-4GlcNAcb1-3)GalNAca-Sp8 |
| 20 | Galb1-4GlcNAcb1-6(Galb1-4GlcNAcb1-3)GalNAc-Sp14 |
| 21 | GlcNAcb1-6(GlcNAcb1-4)(GlcNAcb1-3)GlcNAc-Sp8 |
| 22 | 6S(3S)Galb1-4(6S)GlcNAcb-Sp0 |
| 23 | 6S(3S)Galb1-4GlcNAcb-Sp0 |
| 24 | (3S)Galb1-4(Fuca1-3)(6S)Glc-Sp0 |
| 25 | (3S)Galb1-4Glcb-Sp8 |
| 26 | (3S)Galb1-4(6S)Glcb-Sp0 |
| 27 | (3S)Galb1-4(6S)Glcb-Sp8 |
| 28 | (3S)Galb1-3(Fuca1-4)GlcNAcb-Sp8 |
| 29 | (3S)Galb1-3GalNAca-Sp8 |
| 30 | (3S)Galb1-3GlcNAcb-Sp0 |
| 31 | (3S)Galb1-3GlcNAcb-Sp8 |
| 32 | (3S)Galb1-4(Fuca1-3)GlcNAc-Sp0 |
| 33 | (3S)Galb1-4(Fuca1-3)GlcNAc-Sp8 |
| 34 | (3S)Galb1-4(6S)GlcNAcb-Sp0 |
| 35 | (3S)Galb1-4(6S)GlcNAcb-Sp8 |
| 36 | (3S)Galb1-4GlcNAcb-Sp0 |
| 37 | (3S)Galb1-4GlcNAcb-Sp8 |
| 38 | (3S)Galb-Sp8 |
| 39 | (6S)(4S)Galb1-4GlcNAcb-Sp0 |
| 40 | (4S)Galb1-4GlcNAcb-Sp0 |
| 41 | (6P)Mana-Sp8 |
| 42 | (6S)Galb1-4Glcb-Sp0 |
| 43 | (6S)Galb1-4Glcb-Sp8 |
| 44 | (6S)Galb1-4GlcNAcb-Sp8 |
| 45 | (6S)Galb1-4(6S)Glcb-Sp8 |
| 46 | Neu5Aca2-3(6S)Galb1-4GlcNAcb-Sp8 |
| 47 | (6S)GlcNAcb-Sp8 |
| 48 | Neu5,9Ac$_2$a-Sp8 |
| 49 | Neu5,9Ac2a2-6Galb1-4GlcNAcb-Sp8 |
| 50 | Mana1-6(Mana1-3)Manb1-4GlcNAcb1-4GlcNAcb-Sp12 |
| 51 | Mana1-6(Mana1-3)Manb1-4GlcNAcb1-4GlcNAcb-Sp13 |
| 52 | GlcNAcb1-2Mana1-6(GlcNAcb1-2Mana1-3)Manb1-4GlcNAcb1-4GlcNAcb-Sp12 |
| 53 | GlcNAcb1-2Mana1-6(GlcNAcb1-2Mana1-3)Manb1-4GlcNAcb1-4GlcNAcb-Sp13 |
| 54 | Galb1-4GlcNAcb1-2Mana1-6(Galb1-4GlcNAcb1-2Mana1-3)Manb1-4GlcNAcb1-4GlcNAcb-Sp12 |
| 55 | Neu5Aca2-6Galb1-4GlcNAcb1-2Mana1-6(Neu5Aca2-6Galb1-4GlcNAcb1-2Mana1-3)Manb1-4GlcNAcb1-4GlcNAcb-Sp12 |
| 56 | Neu5Aca2-6Galb1-4GlcNAcb1-2Mana1-6(Neu5Aca2-6Galb1-4GlcNAcb1-2Man-a1-3)Manb1-4GlcNAcb1-4GlcNAcb-Sp21 |
| 57 | Neu5Aca2-6Galb1-4GlcNAcb1-2Mana1-6(Neu5Aca2-6Galb1-4GlcNAcb1-2Mana1-3)Manb1-4GlcNAcb1-4GlcNAcb-Sp24 |
| 58 | Fuca1-2Galb1-3GalNAcb1-3Gala-Sp9 |
| 59 | Fuca1-2Galb1-3GalNAcb1-3Gala1-4Galb1-4Glcb-Sp9 |
| 60 | Fuca1-2Galb1-3(Fuca1-4)GlcNAcb-Sp8 |
| 61 | Fuca1-2Galb1-3GalNAca-Sp8 |
| 62 | Fuca1-2Galb1-3GalNAca-Sp14 |
| 63 | Fuca1-2Galb1-3GalNAcb1-4(Neu5Aca2-3)Galb1-4Glcb-Sp0 |
| 64 | Fuca1-2Galb1-3GalNAcb1-4(Neu5Aca2-3)Galb1-4Glcb-Sp9 |
| 65 | Fuca1-2Galb1-3GlcNAcb1-3Galb1-4Glcb-Sp8 |
| 66 | Fuca1-2Galb1-3GlcNAcb1-3Galb1-4Glcb-Sp10 |
| 67 | Fuca1-2Galb1-3GlcNAcb-Sp0 |
| 68 | Fuca1-2Galb1-3GlcNAcb-Sp8 |
| 69 | Fuca1-2Galb1-4(Fuca1-3)GlcNAcb1-3Galb1-4(Fuca1-3)GlcNAcb-Sp0 |
| 70 | Fuca1-2Galb1-4(Fuca1-3)GlcNAcb1-3Galb1-4(Fuca1-3)GlcNAcb1-3Galb1-4(Fuca1-3)GlcNAcb-Sp0 |
| 71 | Fuca1-2Galb1-4(Fuca1-3)GlcNAcb-Sp0 |
| 72 | Fuca1-2Galb1-4(Fuca1-3)GlcNAcb-Sp8 |
| 73 | Fuca1-2Galb1-4GlcNAcb1-3Galb1-4GlcNAcb-Sp0 |
| 74 | Fuca1-2Galb1-4GlcNAcb1-3Galb1-4GlcNAcb1-3Galb1-4GlcNAcb-Sp0 |
| 75 | Fuca1-2Galb1-4GlcNAcb-Sp0 |

TABLE 9-continued

| Chart Number | |
|---|---|
| 76 | Fuca1-2Galb1-4GlcNAcb-Sp8 |
| 77 | Fuca1-2Galb1-4Glcb-Sp0 |
| 78 | Fuca1-2Galb-Sp8 |
| 79 | Fuca1-3GlcNAcb-Sp8 |
| 80 | Fuca1-4GlcNAcb-Sp8 |
| 81 | Fucb1-3GlcNAcb-Sp8 |
| 82 | GalNAca1-3(Fuca1-2)Galb1-3GlcNAcb-Sp0 |
| 83 | GalNAca1-3(Fuca1-2)Galb1-4(Fuca1-3)GlcNAcb-Sp0 |
| 84 | (3S)Galb1-4(Fuca1-3)Glcb-Sp0 |
| 85 | GalNAca1-3(Fuca1-2)Galb1-4GlcNAcb-Sp0 |
| 86 | GalNAca1-3(Fuca1-2)Galb1-4GlcNAcb-Sp8 |
| 87 | GalNAca1-3(Fuca1-2)Galb1-4Glcb-Sp0 |
| 88 | GlcNAcb1-3Galb1-3GalNAca-Sp8 |
| 89 | GalNAca1-3(Fuca1-2)Galb-Sp8 |
| 90 | GalNAca1-3(Fuca1-2)Galb-Sp18 |
| 91 | GalNAca1-3GalNAcb-Sp8 |
| 92 | GalNAca1-3Galb-Sp8 |
| 93 | GalNAca1-4(Fuca1-2)Galb1-4GlcNAcb-Sp8 |
| 94 | GalNAcb1-3GalNAca-Sp8 |
| 95 | GalNAcb1-3(Fuca1-2)Galb-Sp8 |
| 96 | GalNAcb1-3Gala1-4Galb1-4GlcNAcb-Sp0 |
| 97 | GalNAcb1-4(Fuca1-3)GlcNAcb-Sp0 |
| 98 | GalNAcb1-4GlcNAcb-Sp0 |
| 99 | GalNAcb1-4GlcNAcb-Sp8 |
| 100 | Gala1-2Galb-Sp8 |
| 101 | Gala1-3(Fuca1-2)Galb1-3GlcNAcb-Sp0 |
| 102 | Gala1-3(Fuca1-2)Galb1-3GlcNAcb-Sp8 |
| 103 | Gala1-3(Fuca1-2)Galb1-4(Fuca1-3)GlcNAcb-Sp0 |
| 104 | Gala1-3(Fuca1-2)Galb1-4(Fuca1-3)GlcNAcb-Sp8 |
| 105 | Gala1-3(Fuca1-2)Galb1-4GlcNAc-Sp0 |
| 106 | Gala1-3(Fuca1-2)Galb1-4Glcb-Sp0 |
| 107 | Gala1-3(Fuca1-2)Galb-Sp8 |
| 108 | Gala1-3(Fuca1-2)Galb-Sp18 |
| 109 | Gala1-4(Gala1-3)Galb1-4GlcNAcb-Sp8 |
| 110 | Gala1-3GalNAca-Sp8 |
| 111 | Gala1-3GalNAca-Sp16 |
| 112 | Gala1-3GalNAcb-Sp8 |
| 113 | Gala1-3Galb1-4(Fuca1-3)GlcNAcb-Sp8 |
| 114 | Gala1-3Galb1-3GlcNAcb-Sp0 |
| 115 | Gala1-3Galb1-4GlcNAcb-Sp8 |
| 116 | Gala1-3Galb1-4Glcb-Sp0 |
| 117 | Gala1-3Galb1-4Glc-Sp10 |
| 118 | Gala1-3Galb-Sp8 |
| 119 | Gala1-4(Fuca1-2)Galb1-4GlcNAcb-Sp8 |
| 120 | Gala1-4Galb1-4GlcNAcb-Sp0 |
| 121 | Gala1-4Galb1-4GlcNAcb-Sp8 |
| 122 | Gala1-4Galb1-4Glcb-Sp0 |
| 123 | Gala1-4GlcNAcb-Sp8 |
| 124 | Gala1-6Glcb-Sp8 |
| 125 | Galb1-2Galb-Sp8 |
| 126 | Galb1-3(Fuca1-4)GlcNAcb1-3Galb1-4(Fuca1-3)GlcNAcb-Sp0 |
| 127 | Galb1-3GlcNAcb1-3Galb1-4(Fuca1-3)GlcNAcb-Sp0 |
| 128 | Galb1-3(Fuca1-4)GlcNAc-Sp0 |
| 129 | Galb1-3(Fuca1-4)GlcNAc-Sp8 |
| 130 | Fuca1-4(Galb1-3)GlcNAcb-Sp8 |
| 131 | Galb1-4GlcNAcb1-6GalNAca-Sp8 |
| 132 | Galb1-4GlcNAcb1-6GalNAc-Sp14 |
| 133 | GlcNAcb1-6(Galb1-3)GalNAca-Sp8 |
| 134 | GlcNAcb1-6(Galb1-3)GalNAca-Sp14 |
| 135 | Neu5Aca2-6(Galb1-3)GalNAca-Sp8 |
| 136 | Neu5Aca2-6(Galb1-3)GalNAca-Sp14 |
| 137 | Neu5Acb2-6(Galb1-3)GalNAca-Sp8 |
| 138 | Neu5Aca2-6(Galb1-3)GlcNAcb1-4Galb1-4Glcb-Sp10 |
| 139 | Galb1-3GalNAca-Sp8 |
| 140 | Galb1-3GalNAca-Sp14 |
| 141 | Galb1-3GalNAca-Sp16 |
| 142 | Galb1-3GalNAcb-Sp8 |
| 143 | Galb1-3GalNAcb1-3Gala1-4Galb1-4Glcb-Sp0 |
| 144 | Galb1-3GalNAcb1-4(Neu5Aca2-3)Galb1-4Glcb-Sp0 |
| 145 | Galb1-3GalNAcb1-4Galb1-4Glcb-Sp8 |
| 146 | Galb1-3Galb-Sp8 |
| 147 | Galb1-3GlcNAcb1-3Galb1-4GlcNAcb-Sp0 |
| 148 | Galb1-3GlcNAcb1-3Galb1-4Glcb-Sp10 |
| 149 | Galb1-3GlcNAcb-Sp0 |
| 150 | Galb1-3GlcNAcb-Sp8 |
| 151 | Galb1-4(Fuca1-3)GlcNAcb-Sp0 |
| 152 | Galb1-4(Fuca1-3)GlcNAcb-Sp8 |
| 153 | Galb1-4(Fuca1-3)GlcNAcb1-3Galb1-4(Fuca1-3)GlcNAcb-Sp0 |

TABLE 9-continued

| Chart Number | |
|---|---|
| 154 | Galb1-4(Fuca1-3)GlcNAcb1-3Galb1-4(Fuca1-3)GlcNAcb1-3Galb1-4(Fuca1-3)GlcNAcb-Sp0 |
| 155 | Galb1-4(6S)Glcb-Sp0 |
| 156 | Galb1-4(6S)Glcb-Sp8 |
| 157 | Galb1-4GalNAca1-3(Fuca1-2)Galb1-4GlcNAcb-Sp8 |
| 158 | Galb1-4GalNAcb1-3(Fuca1-2)Galb1-4GlcNAcb-Sp8 |
| 159 | Galb1-4GlcNAcb1-3GalNAca-Sp8 |
| 160 | Galb1-4GlcNAcb1-3GalNAc-Sp14 |
| 161 | Galb1-4GlcNAcb1-3Galb1-4(Fuca1-3)GlcNAcb1-3Galb1-4(Fuca1-3)GlcNAcb-Sp0 |
| 162 | Galb1-4GlcNAcb1-3Galb1-4GlcNAcb1-3Galb1-4GlcNAcb-Sp0 |
| 163 | Galb1-4GlcNAcb1-3Galb1-4GlcNAcb-Sp0 |
| 164 | Galb1-4GlcNAcb1-3Galb1-4Glcb-Sp0 |
| 165 | Galb1-4GlcNAcb1-3Galb1-4Glcb-Sp8 |
| 166 | Galb1-4GlcNAcb1-6(Galb1-3)GalNAca-Sp8 |
| 167 | Galb1-4GlcNAcb1-6(Galb1-3)GalNAc-Sp14 |
| 168 | Galb1-4GlcNAcb-Sp0 |
| 169 | Galb1-4GlcNAcb-Sp8 |
| 170 | Galb1-4GlcNAcb-Sp23 |
| 171 | Galb1-4Glcb-Sp0 |
| 172 | Galb1-4Glcb-Sp8 |
| 173 | GlcNAca1-3Galb1-4GlcNAcb-Sp8 |
| 174 | GlcNAca1-6Galb1-4GlcNAcb-Sp8 |
| 175 | GlcNAcb1-2Galb1-3GalNAca-Sp8 |
| 176 | GlcNAcb1-6(GlcNAcb1-3)GalNAca-Sp8 |
| 177 | GlcNAcb1-6(GlcNAcb1-3)GalNAca-Sp14 |
| 178 | GlcNAcb1-6(GlcNAcb1-3)Galb1-4GlcNAcb-Sp8 |
| 179 | GlcNAcb1-3GalNAca-Sp8 |
| 180 | GlcNAcb1-3GalNAca-Sp14 |
| 181 | GlcNAcb1-3Galb-Sp8 |
| 182 | GlcNAcb1-3Galb1-4GlcNAcb-Sp0 |
| 183 | GlcNAcb1-3Galb1-4GlcNAcb-Sp8 |
| 184 | GlcNAcb1-3Galb1-4GlcNAcb1-3Galb1-4GlcNAcb-Sp0 |
| 185 | GlcNAcb1-3Galb1-4Glcb-Sp0 |
| 186 | GlcNAcb1-4-MDPLys |
| 187 | GlcNAcb1-6(GlcNAcb1-4)GalNAca-Sp8 |
| 188 | GlcNAcb1-4Galb1-4GlcNAcb-Sp8 |
| 189 | GlcNAcb1-4GlcNAcb1-4GlcNAcb1-4GlcNAcb1-4GlcNAcb1-4GlcNAcb-Sp8 |
| 190 | GlcNAcb1-4GlcNAcb1-4GlcNAcb1-4GlcNAcb1-4GlcNAcb-Sp8 |
| 191 | GlcNAcb1-4GlcNAcb1-4GlcNAcb-Sp8 |
| 192 | GlcNAcb1-6GalNAca-Sp8 |
| 193 | GlcNAcb1-6GalNAca-Sp14 |
| 194 | GlcNAcb1-6Galb1-4GlcNAcb-Sp8 |
| 195 | Glca1-4Glcb-Sp8 |
| 196 | Glca1-4Glca-Sp8 |
| 197 | Glca1-6Glca1-6Glcb-Sp8 |
| 198 | Glcb1-4Glcb-Sp8 |
| 199 | Glcb1-6Glcb-Sp8 |
| 200 | G-ol-Sp8 |
| 201 | GlcAa-Sp8 |
| 202 | GlcAb-Sp8 |
| 203 | GlcAb1-3Galb-Sp8 |
| 204 | GlcAb1-6Galb-Sp8 |
| 205 | KDNa2-3Galb1-3GlcNAcb-Sp0 |
| 206 | KDNa2-3Galb1-4GlcNAcb-Sp0 |
| 207 | Mana1-2Mana1-2Mana1-3Mana-Sp9 |
| 208 | Mana1-2Mana1-6(Mana1-2Mana1-3)Mana-Sp9 |
| 209 | Mana1-2Mana1-3Mana-Sp9 |
| 210 | Mana1-6(Mana1-2Mana1-3)Mana1-6(Mana1-2Mana1-3)Manb1-4GlcNAcb1-4GlcNAcb-Sp12 |
| 211 | Mana1-2Mana1-6(Mana1-3)Mana1-6(Mana1-2Mana1-2Mana1-3)Manb1-4GlcNAcb1-4GlcNAcb-Sp12 |
| 212 | Mana1-2Mana1-6(Mana1-2Mana1-3)Mana1-6(Mana1-2Mana1-2Mana1-3)Manb1-4GlcNAcb1-4GlcNAcb-Sp12 |
| 213 | Mana1-6(Mana1-3)Mana-Sp9 |
| 214 | Mana1-2Mana1-2Mana1-6(Mana1-3)Mana-Sp9 |
| 215 | Mana1-6(Mana1-3)Mana1-6(Mana1-2Mana1-3)Manb1-4GlcNAcb1-4GlcNAcb-Sp12 |
| 216 | Mana1-6(Mana1-3)Mana1-6(Mana1-3)Manb1-4GlcNAcb1-4GlcNAcb-Sp12 |
| 217 | Manb1-4GlcNAcb-Sp0 |
| 218 | Neu5Aca2-3Galb1-4GlcNAcb1-3Galb1-4(Fuca1-3)GlcNAcb-Sp0 |
| 219 | (3S)Galb1-4(Fuca1-3)(6S)GlcNAcb-Sp8 |
| 220 | Fuca1-2(6S)Galb1-4GlcNAcb-Sp0 |
| 221 | Fuca1-2Galb1-4(6S)GlcNAcb-Sp8 |
| 222 | Fuca1-2(6S)Galb1-4(6S)Glcb-Sp0 |
| 223 | Neu5Aca2-3Galb1-3GalNAca-Sp8 |

TABLE 9-continued

| Chart Number | |
|---|---|
| 224 | Neu5Aca2-3Galb1-3GalNAca-Sp14 |
| 225 | GalNAcb1-4(Neu5Aca2-8Neu5Aca2-8Neu5Aca2-8Neu5Aca2-3)Galb1-4Glcb-Sp0 |
| 226 | GalNAcb1-4(Neu5Aca2-8Neu5Aca2-8Neu5Aca2-3)Galb1-4Glcb-Sp0 |
| 227 | Neu5Aca2-8Neu5Aca2-8Neu5Aca2-3Galb1-4Glcb-Sp0 |
| 228 | GalNAcb1-4(Neu5Aca2-8Neu5Aca2-3)Galb1-4Glcb-Sp0 |
| 229 | Neu5Aca2-8Neu5Aca2-8Neu5Aca-Sp8 |
| 230 | Neu5Aca2-3(6S)Galb1-4(Fuca1-3)GlcNAcb-Sp8 |
| 231 | GalNAcb1-4(Neu5Aca2-3)Galb1-4GlcNAcb-Sp0 |
| 232 | GalNAcb1-4(Neu5Aca2-3)Galb1-4GlcNAcb-Sp8 |
| 233 | GalNAcb1-4(Neu5Aca2-3)Galb1-4Glcb-Sp0 |
| 234 | Neu5Aca2-3Galb1-3GalNAcb1-4(Neu5Aca2-3)Galb1-4Glcb-Sp0 |
| 235 | Neu5Aca2-6(Neu5Aca2-3)GalNAca-Sp8 |
| 236 | Neu5Aca2-3GalNAca-Sp8 |
| 237 | Neu5Aca2-3GalNAcb1-4GlcNAcb-Sp0 |
| 238 | Neu5Aca2-3Galb1-3(6S)GlcNAc-Sp8 |
| 239 | Neu5Aca2-3Galb1-3(Fuca1-4)GlcNAcb-Sp8 |
| 240 | Neu5Aca2-3Galb1-3(Fuca1-4)GlcNAcb1-3Galb1-4(Fuca1-3)GlcNAcb-Sp0 |
| 241 | Neu5Aca2-3Galb1-4(Neu5Aca2-3Galb1-3)GlcNAcb-Sp8 |
| 242 | Neu5Aca2-3Galb1-3(6S)GalNAca-Sp8 |
| 243 | Neu5Aca2-6(Neu5Aca2-3Galb1-3)GalNAca-Sp8 |
| 244 | Neu5Aca2-6(Neu5Aca2-3Galb1-3)GalNAca-Sp14 |
| 245 | Neu5Aca2-3Galb-Sp8 |
| 246 | Neu5Aca2-3Galb1-3GalNAcb1-3Gala1-4Galb1-4Glcb-Sp0 |
| 247 | Neu5Aca2-3Galb1-3GlcNAcb1-3Galb1-4GlcNAcb-Sp0 |
| 248 | Fuca1-2(6S)Galb1-4Glcb-Sp0 |
| 249 | Neu5Aca2-3Galb1-3GlcNAcb-Sp0 |
| 250 | Neu5Aca2-3Galb1-3GlcNAcb-Sp8 |
| 251 | Neu5Aca2-3Galb1-4(6S)GlcNAcb-Sp8 |
| 252 | Neu5Aca2-3Galb1-4(Fuca1-3)(6S)GlcNAcb-Sp8 |
| 253 | Neu5Aca2-3Galb1-4(Fuca1-3)GlcNAcb1-3Galb1-4(Fuca1-3)GlcNAcb1-3Galb1-4(Fuca1-3)GlcNAcb-Sp0 |
| 254 | Neu5Aca2-3Galb1-4(Fuca1-3)GlcNAcb-Sp0 |
| 255 | Neu5Aca2-3Galb1-4(Fuca1-3)GlcNAcb-Sp8 |
| 256 | Neu5Aca2-3Galb1-4(Fuca1-3)GlcNAcb1-3Galb-Sp8 |
| 257 | Neu5Aca2-3Galb1-4(Fuca1-3)GlcNAcb1-3Galb1-4GlcNAcb-Sp8 |
| 258 | Neu5Aca2-3Galb1-4GlcNAcb1-3Galb1-4GlcNAcb1-3Galb1-4GlcNAcb-Sp0 |
| 259 | Neu5Aca2-3Galb1-4GlcNAcb-Sp0 |
| 260 | Neu5Aca2-3Galb1-4GlcNAcb-Sp8 |
| 261 | Neu5Aca2-3Galb1-4GlcNAcb1-3Galb1-4GlcNAcb-Sp0 |
| 262 | Fuca1-2Galb1-4(6S)Glcb-Sp0 |
| 263 | Neu5Aca2-3Galb1-4Glcb-Sp0 |
| 264 | Neu5Aca2-3Galb1-4Glcb-Sp8 |
| 265 | Neu5Aca2-6GalNAca-Sp8 |
| 266 | Neu5Aca2-6GalNAcb1-4GlcNAcb-Sp0 |
| 267 | Neu5Aca2-6Galb1-4(6S)GlcNAcb-Sp8 |
| 268 | Neu5Aca2-6Galb1-4GlcNAcb-Sp0 |
| 269 | Neu5Aca2-6Galb1-4GlcNAcb-Sp8 |
| 270 | Neu5Aca2-6Galb1-4GlcNAcb1-3Galb1-4(Fuca1-3)GlcNAcb1-3Galb1-4(Fuca1-3)GlcNAcb-Sp0 |
| 271 | Neu5Aca2-6Galb1-4GlcNAcb1-3Galb1-4GlcNAcb-Sp0 |
| 272 | Neu5Aca2-6Galb1-4Glcb-Sp0 |
| 273 | Neu5Aca2-6Galb1-4Glcb-Sp8 |
| 274 | Neu5Aca2-6Galb-Sp8 |
| 275 | Neu5Aca2-8Neu5Aca-Sp8 |
| 276 | Neu5Aca2-8Neu5Aca2-3Galb1-4Glcb-Sp0 |
| 277 | Galb1-3(Fuca1-4)GlcNAcb1-3Galb1-3(Fuca1-4)GlcNAcb-Sp0 |
| 278 | Neu5Acb2-6GalNAca-Sp8 |
| 279 | Neu5Acb2-6Galb1-4GlcNAcb-Sp8 |
| 280 | Neu5Gca2-3Galb1-3(Fuca1-4)GlcNAcb-Sp0 |
| 281 | Neu5Gca2-3Galb1-3GlcNAcb-Sp0 |
| 282 | Neu5Gca2-3Galb1-4(Fuca1-3)GlcNAcb-Sp0 |
| 283 | Neu5Gca2-3Galb1-4GlcNAcb-Sp0 |
| 284 | Neu5Gca2-3Galb1-4Glcb-Sp0 |
| 285 | Neu5Gca2-6GalNAca-Sp0 |
| 286 | Neu5Gca2-6Galb1-4GlcNAcb-Sp0 |
| 287 | Neu5Gca-Sp8 |
| 288 | Neu5Aca2-3Galb1-4GlcNAcb1-6(Galb1-3)GalNAca-Sp14 |
| 289 | Galb1-3GlcNAcb1-3Galb1-3GlcNAcb-Sp0 |
| 290 | Galb1-4(Fuca1-3)(6S)GlcNAcb-Sp0 |
| 291 | Galb1-4(Fuca1-3)(6S)Glcb-Sp0 |
| 292 | Galb1-4(Fuca1-3)GlcNAcb1-3Galb1-3(Fuca1-4)GlcNAcb-Sp0 |
| 293 | Galb1-4GlcNAcb1-3Galb1-3GlcNAcb-Sp0 |
| 294 | Neu5Aca2-3Galb1-3GlcNAcb1-3Galb1-3GlcNAcb-Sp0 |
| 295 | Neu5Aca2-3Galb1-4GlcNAcb1-3Galb1-3GlcNAcb-Sp0 |
| 296 | 4S(3S)Galb1-4GlcNAcb-Sp0 |

TABLE 9-continued

| Chart Number | |
|---|---|
| 297 | (6S)Galb1-4(6S)GlcNAcb-Sp0 |
| 298 | (6P)Glcb-Sp10 |
| 299 | Neu5Aca2-3Galb1-4(Fuca1-3)GlcNAcb1-6(Galb1-3)GalNAca-Sp14 |
| 300 | Galb1-3Galb1-4GlcNAcb-Sp8 |
| 301 | Neu5Aca2-6Galb1-4GlcNAcb1-2Mana1-6(Galb1-4GlcNAcb1-2Mana1-3)Manb1-4GlcNAcb1-4GlcNAcb-Sp12 |
| 302 | Galb1-4GlcNAcb1-6(Galb1-4GlcNAcb1-3)Galb1-4GlcNAc-Sp0 |
| 303 | GlcNAcb1-6(Galb1-4GlcNAcb1-3)Galb1-4GlcNAc-Sp0 |
| 304 | Galb1-4GlcNAca1-6Galb1-4GlcNAcb-Sp0 |
| 305 | Galb1-4GlcNAcb1-6Galb1-4GlcNAcb-Sp0 |
| 306 | GalNAcb1-3Galb-Sp8 |
| 307 | GlcAb1-3GlcNAcb-Sp8 |
| 308 | Neu5Aca2-6Galb1-4GlcNAcb1-2Mana1-6(GlcNAcb1-2Mana1-3)Manb1-4GlcNAcb1-4GlcNAcb-Sp12 |
| 309 | GlcNAcb1-3Man-Sp10 |
| 310 | GlcNAcb1-4GlcNAcb-Sp10 |
| 311 | GlcNAcb1-4GlcNAcb-Sp12 |
| 312 | MurNAcb1-4GlcNAcb-Sp10 |
| 313 | Mana1-6Manb-Sp10 |
| 314 | Mana1-6(Mana1-3)Mana1-6(Mana1-3)Manb-Sp10 |
| 315 | Mana1-2Mana1-6(Mana1-3)Mana1-6(Mana1-2Mana1-2Mana1-3)Mana-Sp9 |
| 316 | Mana1-2Mana1-6(Mana1-2Mana1-3)Mana1-6(Mana1-2Mana1-2Mana1-3)Mana-Sp9 |
| 317 | Neu5Aca2-3Galb1-4GlcNAcb1-6(Neu5Aca2-3Galb1-3)GalNAca-Sp14 |
| 318 | Neu5Aca2-6Galb1-4GlcNAcb1-2Mana1-6(Neu5Aca2-3Galb1-4GlcNAcb1-2Mana1-3)Manb1-4GlcNAcb1-4GlcNAcb-Sp12 |
| 319 | Galb1-4GlcNAcb1-2Mana1-6(Neu5Aca2-6Galb1-4GlcNAcb1-2Mana1-3)Manb1-4GlcNAcb1-4GlcNAcb-Sp12 |
| 320 | Neu5Aca2-8Neu5Acb-Sp17 |
| 321 | Neu5Aca2-8Neu5Aca2-8Neu5Acb-Sp8 |
| 322 | Neu5Gcb2-6Galb1-4GlcNAc-Sp8 |
| 323 | Galb1-3GlcNAcb1-2Mana1-6(Galb1-3GlcNAcb1-2Mana1-3)Manb1-4GlcNAcb1-4GlcNAcb-Sp19 |
| 324 | Neu5Aca2-3Galb1-4GlcNAcb1-2Mana1-6(Neu5Aca2-3Galb1-4GlcNAcb1-2Mana1-3)Manb1-4GlcNAcb1-4GlcNAcb-Sp12 |
| 325 | Neu5Aca2-3Galb1-4GlcNAcb1-2Mana1-6(Neu5Aca2-6Galb1-4GlcNAcb1-2Mana1-3)Manb1-4GlcNAcb1-4GlcNAcb-Sp12 |
| 326 | Galb1-4(Fuca1-3)GlcNAcb1-2Mana1-6(Galb1-4(Fuca1-3)GlcNAcb1-2Mana1-3)Manb1-4GlcNAcb1-4GlcNAcb-Sp20 |
| 327 | Neu5,9Ac2a2-3Galb1-4GlcNAcb-Sp0 |
| 328 | Neu5,9Ac2a2-3Galb1-3GlcNAcb-Sp0 |
| 329 | Neu5Aca2-6Galb1-4GlcNAcb1-3Galb1-3GlcNAcb-Sp0 |
| 330 | Neu5Aca2-3Galb1-3(Fuca1-4)GlcNAcb1-3Galb1-3(Fuca1-4)GlcNAcb-Sp0 |
| 331 | Neu5Aca2-6Galb1-4GlcNAcb1-3Galb1-4GlcNAcb1-3Galb1-4GlcNAcb-Sp0 |
| 332 | Gala1-4Galb1-4GlcNAcb1-3Galb1-4Glcb-Sp0 |
| 333 | GalNAcb1-3Gala1-4Galb1-4GlcNAcb1-3Galb1-4Glcb-Sp0 |
| 334 | GalNAca1-3(Fuca1-2)Galb1-4GlcNAcb1-3Galb1-4GlcNAcb-Sp0 |
| 335 | GalNAca1-3(Fuca1-2)Galb1-4GlcNAcb1-3Galb1-4GlcNAcb1-3Galb1-4GlcNAcb-Sp0 |
| 336 | Neu5Aca2-3Galb1-4(Fuca1-3)GlcNAcb1-6(Neu5Aca2-3Galb1-3)GalNAc-Sp14 |
| 337 | GlcNAca1-4Galb1-4GlcNAcb1-3Galb1-4GlcNAcb1-3Galb1-4GlcNAcb-Sp0 |
| 338 | GlcNAca1-4Galb1-4GlcNAcb-Sp0 |
| 339 | GlcNAca1-4Galb1-3GlcNAcb-Sp0 |
| 340 | GlcNAca1-4Galb1-4GlcNAcb1-3Galb1-4Glcb-Sp0 |
| 341 | GlcNAca1-4Galb1-4GlcNAcb1-3Galb1-4(Fuca1-3)GlcNAcb1-3Galb1-4(Fuca1-3)GlcNAcb-Sp0 |
| 342 | GlcNAca1-4Galb1-4GlcNAcb1-3Galb1-4GlcNAcb-Sp0 |
| 343 | GlcNAca1-4Galb1-3GalNAc-Sp14 |
| 344 | Neu5Aca2-6Galb1-4GlcNAcb1-2Mana1-6(Mana1-3)Manb1-4GlcNAcb1-4GlcNAc-Sp12 |
| 345 | Mana1-6(Neu5Aca2-6Galb1-4GlcNAcb1-2Mana1-3)Manb1-4GlcNAcb1-4GlcNAc-Sp12 |
| 346 | Neu5Aca2-6Galb1-4GlcNAcb1-2Mana1-6Manb1-4GlcNAcb1-4GlcNAc-Sp12 |
| 347 | Neu5Aca2-6Galb1-4GlcNAcb1-2Mana1-3Manb1-4GlcNAcb1-4GlcNAc-Sp12 |
| 348 | Galb1-4GlcNAcb1-2Mana1-3Manb1-4GlcNAcb1-4GlcNAc-Sp12 |
| 349 | Galb1-4GlcNAcb1-2Mana1-6Manb1-4GlcNAcb1-4GlcNAc-Sp12 |
| 350 | Mana1-6(Galb1-4GlcNAcb1-2Mana1-3)Manb1-4GlcNAcb1-4GlcNAcb-Sp12 |

TABLE 9-continued

| Chart Number | |
|---|---|
| 351 | GlcNAcb1-2Mana1-6(GlcNAcb1-2Mana1-3)Manb1-4GlcNAcb1-4(Fuca1-6)GlcNAcb-Sp22 |
| 352 | Galb1-4GlcNAcb1-2Mana1-6(Galb1-4GlcNAcb1-2Mana1-3)Manb1-4GlcNAcb1-4(Fuca1-6)GlcNAcb-Sp22 |
| 353 | Galb1-3GlcNAcb1-2Mana1-6(Galb1-3GlcNAcb1-2Mana1-3)Manb1-4GlcNAcb1-4(Fuca1-6)GlcNAcb-Sp22 |
| 354 | (6S)GlcNAcb1-3Galb1-4GlcNAcb-Sp0 |
| 355 | KDNa2-3Galb1-4(Fuca1-3)GlcNAc-Sp0 |
| 356 | KDNa2-6Galb1-4GlcNAc-Sp0 |
| 357 | KDNa2-3Galb1-4Glc-Sp0 |
| 358 | KDNa2-3Galb1-3GalNAca-Sp14 |
| 359 | Fuca1-2Galb1-3GlcNAcb1-2Mana1-6(Fuca1-2Galb1-3GlcNAcb1-2Mana1-3)Manb1-4GlcNAcb1-4GlcNAcb-Sp20 |
| 360 | Fuca1-2Galb1-4GlcNAcb1-2Mana1-6(Fuca1-2Galb1-4GlcNAcb1-2Mana1-3)Manb1-4GlcNAcb1-4GlcNAcb-Sp20 |
| 361 | Fuca1-2Galb1-4(Fuca1-3)GlcNAcb1-2Mana1-6(Fuca1-2Galb1-4(Fuca1-3)GlcNAcb1-2Mana1-3)Manb1-4GlcNAcb1-4GlcNAb-Sp20 |
| 362 | Gala1-3Galb1-4GlcNAcb1-2Mana1-6(Gala1-3Galb1-4GlcNAcb1-2Mana1-3)Manb1-4GlcNAcb1-4GlcNAcb-Sp20 |
| 363 | Galb1-4GlcNAcb1-2Mana1-6(Mana1-3)Manb1-4GlcNAcb1-4GlcNAcb-Sp12 |
| 364 | Fuca1-4(Galb1-3)GlcNAcb1-2Mana1-6(Fuca1-4(Galb1-3)GlcNAcb1-2Mana1-3)Manb1-4GlcNAcb1-4(Fuca1-6)GlcNAcb-Sp22 |
| 365 | Neu5Aca2-6GlcNAcb1-4GlcNAc-Sp21 |
| 366 | Neu5Aca2-6GlcNAcb1-4GlcNAcb1-4GlcNAc-Sp21 |
| 367 | Galb1-4(Fuca1-3)GlcNAcb1-6(Fuca1-2Galb1-4GlcNAcb1-3)Galb1-4Glc-Sp21 |
| 368 | Galb1-4GlcNAcb1-2Mana1-6(Galb1-4GlcNAcb1-4(Galb1-4GlcNAcb1-2)Mana1-3)Manb1-4GlcNAcb1-4GlcNAc-Sp21 |
| 369 | GalNAca1-3(Fuca1-2)Galb1-4GlcNAcb1-2Mana1-6(GalNAca1-3(Fuca1-2)Galb1-4GlcNAcb1-2Mana1-3)Manb1-4GlcNAcb1-4GlcNAcb-Sp20 |
| 370 | Gala1-3(Fuca1-2)Galb1-4GlcNAcb1-2Mana1-6(Gala1-3(Fuca1-2)Galb1-4GlcNAcb1-2Mana1-3)Manb1-4GlcNAcb1-4GlcNAcb-Sp20 |
| 371 | Gala1-3Galb1-4(Fuca1-3)GlcNAcb1-2Mana1-6(Gala1-3Galb1-4(Fuca1-3)GlcNAcb1-2Mana1-3)Manb1-4GlcNAcb1-4GlcNAcb-Sp20 |
| 372 | GalNAca1-3(Fuca1-2)Galb1-3GlcNAcb1-2Mana1-6(GalNAca1-3(Fuca1-2)Galb1-3GlcNAcb1-2Mana1-3)Manb1-4GlcNAcb1-4GlcNAcb-Sp20 |
| 373 | Gala1-3(Fuca1-2)Galb1-3GlcNAcb1-2Mana1-6(Gala1-3(Fuca1-2)Galb1-3GlcNAcb1-2Mana1-3)Manb1-4GlcNAcb1-4GlcNAcb-Sp20 |
| 374 | Fuca1-4(Fuca1-2Galb1-3)GlcNAcb1-2Mana1-3(Fuca1-4(Fuca1-2Galb1-3)GlcNAcb1-2Mana1-3)Manb1-4GlcNAcb1-4GlcNAcb-Sp19 |
| 375 | Neu5Aca2-3Galb1-4GlcNAcb1-3GalNAc-Sp14 |
| 376 | Neu5Aca2-6Galb1-4GlcNAcb1-3GalNAc-Sp14 |
| 377 | Neu5Aca2-3Galb1-4(Fuca1-3)GlcNAcb1-3GalNAca-Sp14 |
| 378 | GalNAcb1-4GlcNAcb1-2Mana1-6(GalNAcb1-4GlcNAcb1-2Mana1-3)Manb1-4GlcNAcb1-4GlcNAc-Sp12 |
| 379 | Galb1-3GalNAca1-3(Fuca1-2)Galb1-4Glc-Sp0 |
| 380 | Galb1-3GalNAca1-3(Fuca1-2)Galb1-4GlcNAc-Sp0 |
| 381 | Galb1-3GlcNAcb1-3Galb1-4GlcNAcb1-6(Galb1-3GlcNAcb1-3)Galb1-4Glcb-Sp0 |
| 382 | Galb1-4(Fuca1-3)GlcNAcb1-6(Galb1-3GlcNAcb1-3)Galb1-4Glc-Sp21 |
| 383 | Galb1-4GlcNAcb1-6(Fuca1-4(Fuca1-2Galb1-3)GlcNAcb1-3)Galb1-4Glc-Sp21 |
| 384 | Galb1-4(Fuca1-3)GlcNAcb1-6(Fuca1-4(Fuca1-2Galb1-3)GlcNAcb1-3)Galb1-4Glc-Sp21 |
| 385 | Galb1-3GlcNAcb1-3Galb1-4(Fuca1-3)GlcNAcb1-6(Galb1-3GlcNAcb1-3)Galb1-4Glc-Sp21 |
| 386 | Galb1-4GlcNAcb1-6(Galb1-4GlcNAcb1-2)Mana1-6(Galb1-4GlcNAcb1-4(Galb1-4GlcNAcb1-2)Mana1-3)Manb1-4GlcNAcb1-4GlcNAcb-Sp21 |
| 387 | GlcNAcb1-2Mana1-6(GlcNAcb1-4(GlcNAcb1-2)Mana1-3)Manb1-4GlcNAcb1-4GlcNAc-Sp21 |
| 388 | Fuca1-2Galb1-3GalNAca1-3(Fuca1-2)Galb1-4Glcb-Sp0 |
| 389 | Fuca1-2Galb1-3GalNAca1-3(Fuca1-2)Galb1-4GlcNAcb-Sp0 |
| 390 | Galb1-3GlcNAcb1-3GalNAca-Sp14 |
| 391 | GalNAcb1-4(Neu5Aca2-3)Galb1-4GlcNAcb1-3GalNAca-Sp14 |
| 392 | GalNAca1-3(Fuca1-2)Galb1-3GalNAca1-3(Fuca1-2)Galb1-4GlcNAcb-Sp0 |
| 393 | Gala1-3Galb1-3GlcNAcb1-2Mana1-6(Gala1-3Galb1-3GlcNAcb1-2Mana1-3)Manb1-4GlcNAcb1-4GlcNAc-Sp19 |
| 394 | Gala1-3Galb1-3(Fuca1-4)GlcNAcb1-2Mana1-6(Gala1-3Galb1-3(Fuca1-4)GlcNAcb1-2Mana1-3)Manb1-4GlcNAcb1-4GlcNAc-Sp19 |
| 395 | Neu5Aca2-3Galb1-3GlcNAcb1-2Mana1-6(Neu5Aca2-3Galb1-3GlcNAcb1-2Mana1-3)Manb1-4GlcNAcb1-4GlcNAc-Sp19 |
| 396 | GlcNAcb1-2Mana1-6(Galb1-4GlcNAcb1-2Mana1-3)Manb1-4GlcNAcb1-4GlcNAc-Sp12 |
| 397 | Galb1-4GlcNAcb1-2Mana1-6(GlcNAcb1-2Mana1-3)Manb1-4GlcNAcb1-4GlcNAc-Sp12 |
| 398 | Neu5Aca2-3Galb1-3GlcNAcb1-3GalNAca-Sp14 |
| 399 | Fuca1-2Galb1-4GlcNAcb1-3GalNAca-Sp14 |

TABLE 9-continued

| Chart Number | |
|---|---|
| 400 | Galb1-4(Fuca1-3)GlcNAcb1-3GalNAca-Sp14 |
| 401 | GalNAca1-3GalNAcb1-3Gala1-4Galb1-4GlcNAcb-Sp0 |
| 402 | Gala1-4Galb1-3GlcNAcb1-2Mana1-6(Gala1-4Galb1-3GlcNAcb1-2Mana1-3)Manb1-4GlcNAcb1-4GlcNAcb-Sp19 |
| 403 | Gala1-4Galb1-4GlcNAcb1-2Mana1-6(Gala1-4Galb1-4GlcNAcb1-2Mana1-3)Manb1-4GlcNAcb1-4GlcNAcb-Sp24 |
| 404 | Gala1-3Galb1-4GlcNAcb1-3GalNAca-Sp14 |
| 405 | Galb1-3GlcNAcb1-6Galb1-4GlcNAcb-Sp0 |
| 406 | Galb1-3GlcNAca1-6Galb1-4GlcNAcb-Sp0 |
| 407 | GalNAcb1-3Gala1-6Galb1-4Glcb-Sp8 |
| 408 | Gala1-3(Fuca1-2)Galb1-4(Fuca1-3)Glcb-Sp21 |
| 409 | Galb1-4GlcNAcb1-6(Neu5Aca2-6Galb1-3GlcNAcb1-3)Galb1-4Glc-Sp21 |
| 410 | Galb1-3GalNAcb1-4(Neu5Aca2-8Neu5Aca2-3)Galb1-4Glcb-Sp0 |
| 411 | Neu5Aca2-3Galb1-3GalNAcb1-4(Neu5Aca2-8Neu5Aca2-3)Galb1-4Glcb-Sp0 |
| 412 | Gala1-3(Fuca1-2)Galb1-4GlcNAcb1-3GalNAca-Sp14 |
| 413 | GalNAca1-3(Fuca1-2)Galb1-4GlcNAcb1-3GalNAca-Sp14 |
| 414 | GalNAca1-3GalNAcb1-3Gala1-4Galb1-4Glcb-Sp0 |
| 415 | Fuca1-2Galb1-4(Fuca1-3)GlcNAcb1-3GalNAca-Sp14 |
| 416 | Gala1-3(Fuca1-2)Galb1-4(Fuca1-3)GlcNAcb1-3GalNAc-Sp14 |
| 417 | GalNAca1-3(Fuca1-2)Galb1-4(Fuca1-3)GlcNAcb1-3GalNAc-Sp14 |
| 418 | Galb1-4(Fuca1-3)GlcNAcb1-2Mana1-6(Galb1-4(Fuca1-3)GlcNAcb1-2Mana1-3)Manb1-4GlcNAcb1-4(Fuca1-6)GlcNAcb-Sp22 |
| 419 | Fuca1-2Galb1-4GlcNAcb1-2Mana1-6(Fuca1-2Galb1-4GlcNAcb1-2Mana1-3)Manb1-4GlcNAcb1-4(Fuca1-6)GlcNAcb-Sp22 |
| 420 | GlcNAcb1-2(GlcNAcb1-6)Mana1-6(GlcNAcb1-2Mana1-3)Manb1-4GlcNAcb1-4GlcNAcb-Sp19 |
| 421 | Fuca1-2Galb1-3GlcNAcb1-3GalNAc-Sp14 |
| 422 | Gala1-3(Fuca1-2)Galb1-3GlcNAcb1-3GalNAc-Sp14 |
| 423 | GalNAca1-3(Fuca1-2)Galb1-3GlcNAcb1-3GalNAc-Sp14 |
| 424 | Gala1-3Galb1-3GlcNAcb1-3GalNAc-Sp14 |
| 425 | Fuca1-2Galb1-3GlcNAcb1-2Mana1-6(Fuca1-2Galb1-3GlcNAcb1-2Mana1-3)Manb1-4GlcNAcb1-4(Fuca1-6)GlcNAcb-Sp22 |
| 426 | Gala1-3(Fuca1-2)Galb1-4GlcNAcb1-2Mana1-6(Gala1-3(Fuca1-2)Galb1-4GlcNAcb1-2Mana1-3)Manb1-4GlcNAcb1-4(Fuca1-6)GlcNAcb-Sp22 |
| 427 | Galb1-3GlcNAcb1-6(Galb1-3GlcNAcb1-2)Mana1-6(Galb1-3GlcNAcb1-2Mana1-3)Manb1-4GlcNAcb1-4GlcNAcb-Sp19 |
| 428 | Galb1-4GlcNAcb1-6(Fuca1-2Galb1-3GlcNAcb1-3)Galb1-4Glc-Sp21 |
| 429 | Fuca1-3GlcNAcb1-6(Galb1-4GlcNAcb1-3)Galb1-4Glc-Sp21 |
| 430 | GlcNAcb1-2Mana1-6(GlcNAcb1-4)(GlcNAcb1-2Mana1-3)Manb1-4GlcNAcb1-4GlcNAc-Sp21 |
| 431 | GlcNAcb1-2Mana1-6(GlcNAcb1-4)(GlcNAcb1-4(GlcNAcb1-2)Mana1-3)Manb1-4GlcNAcb1-4GlcNAc-Sp21 |
| 432 | GlcNAcb1-6(GlcNAcb1-2)Mana1-6(GlcNAcb1-4)(GlcNAcb1-2Mana1-3)Manb1-4GlcNAcb1-4GlcNAc-Sp21 |
| 433 | GlcNAcb1-6(GlcNAcb1-2)Mana1-6(GlcNAcb1-4)(GlcNAcb1-4(GlcNAcb1-2)Mana1-3)Manb1-4GlcNAcb1-4GlcNAc-Sp21 |
| 434 | Galb1-4GlcNAcb1-2Mana1-6(GlcNAcb1-4)(Galb1-4GlcNAcb1-2Mana1-3)Manb1-4GlcNAcb1-4GlcNAc-Sp21 |
| 435 | Galb1-4GlcNAcb1-2Mana1-6(GlcNAcb1-4)(Galb1-4GlcNAcb1-4(Galb1-4GlcNAcb1-2)Mana1-3)Manb1-4GlcNAcb1-4GlcNAc-Sp21 |
| 436 | Galb1-4GlcNAcb1-6(Galb1-4GlcNAcb1-2)Mana1-6(GlcNAcb1-4)(Galb1-4GlcNAcb1-2Mana1-3)Manb1-4GlcNAcb1-4GlcNAc-Sp21 |
| 437 | Galb1-4GlcNAcb1-6(Galb1-4GlcNAcb1-2)Mana1-6(GlcNAcb1-4)(Galb1-4GlcNAcb1-4(Galb1-4GlcNAcb1-2)Mana1-3)Manb1-4GlcNAcb1-4GlcNAc-Sp21 |
| 438 | Galb1-4Galb-Sp10 |
| 439 | Galb1-6Galb-Sp10 |
| 440 | Neu5Aca2-3Galb1-4GlcNAcb1-3Galb-Sp8 |
| 441 | GalNAcb1-6GalNAcb-Sp8 |
| 442 | (6S)Galb1-3GlcNAcb-Sp0 |
| 443 | (6S)Galb1-3(6S)GlcNAc-Sp0 |
| 444 | Fuca1-2Galb1-4GlcNAcb1-2Mana1-6(Fuca1-2Galb1-4GlcNAcb1-2(Fuca1-2Galb1-4GlcNAcb1-4)Mana1-3)Manb1-4GlcNAcb1-4GlcNAcb-Sp12 |
| 445 | Fuca1-2Galb1-4(Fuca1-3)GlcNAcb1-2Mana1-6(Fuca1-2Galb1-4(Fuca1-3)GlcNAcb1-4(Fuca1-2Galb1-4(Fuca1-3)GlcNAcb1-2)Mana1-3)Manb1-4GlcNAcb1-4GlcNAcb-Sp12 |
| 446 | Galb1-4(Fuca1-3)GlcNAcb1-6GalNAc-Sp14 |
| 447 | Galb1-4GlcNAcb1-2Mana-Sp0 |
| 448 | Fuca1-2Galb1-4GlcNAcb1-6(Fuca1-2Galb1-4GlcNAcb1-3)GalNAc-Sp14 |
| 449 | Gala1-3(Fuca1-2)Galb1-4GlcNAcb1-6(Gala1-3(Fuca1-2)Galb1-4GlcNAcb1-3)GalNAc-Sp14 |
| 450 | GalNAca1-3(Fuca1-2)Galb1-4GlcNAcb1-6(GalNAca1-3(Fuca1-2)Galb1-4GlcNAcb1-3)GalNAc-Sp14 |
| 451 | Neu5Aca2-8Neu5Aca2-3Galb1-3GalNAcb1-4(Neu5Aca2-8Neu5Aca2-3)Galb1-4Glcb-Sp0 |
| 452 | GalNAcb1-4Galb1-4Glcb-Sp0 |

TABLE 9-continued

| Chart Number | |
|---|---|
| 453 | GalNAca1-3(Fuca1-2)Galb1-4GlcNAcb1-2Mana1-6(GalNAca1-3(Fuca1-2)Galb1-4GlcNAcb1-2Mana1-3)Manb1-4GlcNAcb1-4(Fuca1-6)GlcNAcb-Sp22 |
| 454 | Gala1-3(Fuca1-2)Galb1-3GlcNAcb1-2Mana1-6(Gala1-3(Fuca1-2)Galb1-3GlcNAcb1-2Mana1-3)Manb1-4GlcNAcb1-4(Fuca1-6)GlcNAcb-Sp22 |
| 455 | Neu5Aca2-6Galb1-4GlcNAcb1-6(Fuca1-2Galb1-3GlcNAcb1-3)Galb1-4Glc-Sp21 |
| 456 | GalNAca1-3(Fuca1-2)Galb1-3GlcNAcb1-2Mana1-6(GalNAca1-3(Fuca1-2)Galb1-3GlcNAcb1-2Mana1-3)Manb1-4GlcNAcb1-4(Fuca1-6)GlcNAcb-Sp22 |
| 457 | Galb1-4GlcNAcb1-6(Galb1-4GlcNAcb1-2)Mana1-6(Galb1-4GlcNAcb1-2Mana1-3)Manb1-4GlcNAcb1-4GlcNAc-Sp19 |
| 458 | Neu5Aca2-3Galb1-4GlcNAcb1-2Mana1-6(GlcNAcb1-4)(Neu5Aca2-3Galb1-4GlcNAcb1-2Mana1-3)Manb1-4GlcNAcb1-4GlcNAcb-Sp21 |
| 459 | Neu5Aca2-3Galb1-4GlcNAcb1-4Mana1-6(GlcNAcb1-4)(Neu5Aca2-3Galb1-4GlcNAcb1-4(Neu5Aca2-3Galb1-4GlcNAcb1-2)Mana1-3)Manb1-4GlcNAcb1-4GlcNAcb-Sp21 |
| 460 | Neu5Aca2-3Galb1-4GlcNAcb1-6(Neu5Aca2-3Galb1-4GlcNAcb1-2)Mana1-6(GlcNAcb1-4)(Neu5Aca2-3Galb1-4GlcNAcb1-2Mana1-3)Manb1-4GlcNAcb1-4GlcNAcb-Sp21 |
| 461 | Neu5Aca2-3Galb1-4GlcNAcb1-6(Neu5Aca2-3Galb1-4GlcNAcb1-2)Mana1-6(GlcNAcb1-4)(Neu5Aca2-3Galb1-4GlcNAcb1-4(Neu5Aca2-3Galb1-4GlcNAcb1-2)Mana1-3)Manb1-4GlcNAcb1-4GlcNAcb-Sp21 |
| 462 | Neu5Aca2-6Galb1-4GlcNAcb1-2Mana1-6(GlcNAcb1-4)(Neu5Aca2-6Galb1-4GlcNAcb1-2Mana1-3)Manb1-4GlcNAcb1-4GlcNAcb-Sp21 |
| 463 | Neu5Aca2-6Galb1-4GlcNAcb1-4Mana1-6(GlcNAcb1-4)(Neu5Aca2-6Galb1-4GlcNAcb1-4(Neu5Aca2-6Galb1-4GlcNAcb1-2)Mana1-3)Manb1-4GlcNAcb1-4GlcNAcb-Sp21 |
| 464 | Neu5Aca2-6Galb1-4GlcNAcb1-6(Neu5Aca2-6Galb1-4GlcNAcb1-2)Mana1-6(GlcNAcb1-4)(Neu5Aca2-6Galb1-4GlcNAcb1-2Mana1-3)Manb1-4GlcNAcb1-4GlcNAcb-Sp21 |
| 465 | Neu5Aca2-6Galb1-4GlcNAcb1-6(Neu5Aca2-6Galb1-4GlcNAcb1-2)Mana1-6(GlcNAcb1-4)(Neu5Aca2-6Galb1-4GlcNAcb1-4(Neu5Aca2-6Galb1-4GlcNAcb1-2)Mana1-3)Manb1-4GlcNAcb1-4GlcNAcb-Sp21 |
| 466 | Gala1-3(Fuca1-2)Galb1-3GalNAca-Sp8 |
| 467 | Gala1-3(Fuca1-2)Galb1-3GalNAcb-Sp8 |
| 468 | Glca1-6Glca1-6Glca1-6Glcb-Sp10 |
| 469 | Glca1-4Glca1-4Glca1-4Glcb-Sp10 |
| 470 | Neu5Aca2-3Galb1-4GlcNAcb1-6(Neu5Aca2-3Galb1-4GlcNAcb1-3)GalNAca-Sp14 |
| 471 | Fuca1-2Galb1-4(Fuca1-3)GlcNAcb1-2Mana1-6(Fuca1-2Galb1-4(Fuca1-3)GlcNAcb1-2Mana1-3)Manb1-4GlcNAcb1-4(Fuca1-6)GlcNAcb-Sp24 |
| 472 | Fuca1-2Galb1-3(Fuca1-4)GlcNAcb1-2Mana1-6(Fuca1-2Galb1-3(Fuca1-4)GlcNAcb1-2Mana1-3)Manb1-4GlcNAcb1-4(Fuca1-6)GlcNAcb-Sp19 |
| 473 | Neu5Aca2-3Galb1-3GlcNAcb1-6(Neu5Aca2-3Galb1-3GlcNAcb1-2)Mana1-6(Neu5Aca2-3Galb1-3GlcNAcb1-2Mana1-3)Manb1-4GlcNAcb1-4GlcNAcb-Sp19 |
| 474 | GlcNAcb1-6(GlcNAcb1-2)Mana1-6(GlcNAcb1-2Mana1-3)Manb1-4GlcNAcb1-4(Fuca1-6)GlcNAcb-Sp24 |
| 475 | Galb1-3GlcNAcb1-2Mana1-6(GlcNAcb1-4)(Galb1-3GlcNAcb1-2Mana1-3)Manb1-4GlcNAcb1-4GlcNAcb-Sp21 |
| 476 | Neu5Aca2-6Galb1-4GlcNAcb1-6(Galb1-3GlcNAcb1-3)Galb1-4Glcb-Sp21 |
| 477 | Neu5Aca2-3Galb1-4GlcNAcb1-2Mana-Sp0 |
| 478 | Neu5Aca2-3Galb1-4GlcNAcb1-6GalNAca-Sp14 |
| 479 | Neu5Aca2-6Galb1-4GlcNAcb1-6GalNAca-Sp14 |
| 480 | Neu5Aca2-6Galb1-4GlcNAcb1-6(Neu5Aca2-6Galb1-4GlcNAcb1-3)GalNAca-Sp14 |
| 481 | Neu5Aca2-6Galb1-4GlcNAcb1-2Mana1-6(Neu5Aca2-6Galb1-4GlcNAcb1-2Mana1-3)Manb1-4GlcNAcb1-4(Fuca1-6)GlcNAcb-Sp24 |
| 482 | Neu5Aca2-3Galb1-4GlcNAcb1-2Mana1-6(Neu5Aca2-3Galb1-4GlcNAcb1-2Mana1-3)Manb1-4GlcNAcb1-4(Fuca1-6)GlcNAcb-Sp24 |
| 483 | Mana1-6(Mana1-3)Manb1-4GlcNAcb1-4(Fuca1-6)GlcNAcb-Sp19 |
| 484 | Galb1-4GlcNAcb1-6(Galb1-4GlcNAcb1-2)Mana1-6(Galb1-4GlcNAcb1-2Mana1-3)Manb1-4GlcNAcb1-4(Fuca1-6)GlcNAcb-Sp24 |
| 485 | Neu5Aca2-3Galb1-3GlcNAcb1-2Mana1-6(GlcNAcb1-4)(Neu5Aca2-3Galb1-3GlcNAcb1-2Mana1-3)Manb1-4GlcNAcb1-4GlcNAc-Sp21 |
| 486 | Neu5Aca2-6Galb1-4GlcNAcb1-6(Fuca1-2Galb1-4(Fuca1-3)GlcNAcb1-3)Galb1-4Glc-Sp21 |
| 487 | Galb1-3GlcNAcb1-6GalNAca-Sp14 |
| 488 | Gala1-3Galb1-3GlcNAcb1-6GalNAca-Sp14 |
| 489 | Galb1-3(Fuca1-4)GlcNAcb1-6GalNAca-Sp14 |
| 490 | Neu5Aca2-3Galb1-3GlcNAcb1-6GalNAca-Sp14 |
| 491 | (3S)Galb1-3(Fuca1-4)GlcNAcb-Sp0 |
| 492 | Galb1-4(Fuca1-3)GlcNAcb1-6(Neu5Aca2-6(Neu5Aca2-3Galb1-3)GlcNAcb1-3)Galb1-4Glc-Sp21 |
| 493 | Fuca1-2Galb1-4GlcNAcb1-6GalNAca-Sp14 |
| 494 | Gala1-3Galb1-4GlcNAcb1-6GalNAca-Sp14 |

TABLE 9-continued

| Chart Number | |
|---|---|
| 495 | Galb1-4(Fuca1-3)GlcNAcb1-2Mana-Sp0 |
| 496 | Fuca1-2(6S)Galb1-3GlcNAcb-Sp0 |
| 497 | Gala1-3(Fuca1-2)Galb1-4GlcNAcb1-6GalNAca-Sp14 |
| 498 | Fuca1-2Galb1-4GlcNAcb1-2Mana-Sp0 |
| 499 | Fuca1-2Galb1-3(6S)GlcNAcb-Sp0 |
| 500 | Fuca1-2(6S)Galb1-3(6S)GlcNAcb-Sp0 |
| 501 | Neu5Aca2-6GalNAcb1-4(6S)GlcNAcb-Sp8 |
| 502 | GalNAcb1-4(Fuca1-3)(6S)GlcNAcb-Sp8 |
| 503 | (3S)GalNAcb1-4(Fuca1-3)GlcNAcb-Sp8 |
| 504 | Fuca1-2Galb1-3GlcNAcb1-6(Fuca1-2Galb1-3GlcNAcb1-3)GalNAca-Sp14 |
| 505 | GalNAca1-3(Fuca1-2)Galb1-3GlcNAcb1-6GalNAca-Sp14 |
| 506 | GlcNAcb1-6(GlcNAcb1-2)Mana1-6(GlcNAcb1-4)(GlcNAcb1-4(GlcNAcb1-2)Mana1-3)Manb1-4GlcNAcb1-4(Fuca1-6)GlcNAc-Sp21 |
| 507 | Galb1-4GlcNAcb1-6(Galb1-4GlcNAcb1-2)Mana1-6(GlcNAcb1-4)Galb1-4GlcNAcb1-4(Galb1-4GlcNAcb1-2)Mana1-3)Manb1-4GlcNAcb1-4(Fuca1-6)GlcNAc-Sp21 |
| 508 | Galb1-3GlcNAca1-3Galb1-4GlcNAcb-Sp8 |
| 509 | Galb1-3(6S)GlcNAcb-Sp8 |
| 510 | (6S)(4S)GalNAcb1-4GlcNAc-Sp8 |
| 511 | (6S)GalNAcb1-4GlcNAc-Sp8 |
| 512 | (3S)GalNAcb1-4(3S)GlcNAc-Sp8 |
| 513 | GalNAcb1-4(6S)GlcNAc-Sp8 |
| 514 | (3S)GalNAcb1-4GlcNAc-Sp8 |
| 515 | (4S)GalNAcb-Sp10 |
| 516 | Galb1-4(6P)GlcNAcb-Sp0 |
| 517 | (6P)Galb1-4GlcNAcb-SP0 |
| 518 | GalNAca1-3(Fuca1-2)Galb1-4GlcNAcb1-6GalNAc-Sp14 |
| 519 | Neu5Aca2-6Galb1-4GlcNAcb1-2Man-Sp0 |
| 520 | Gala1-3Galb1-4GlcNAcb1-2Mana-Sp0 |
| 521 | Gala1-3(Fuca1-2)Galb1-4GlcNAcb1-2Mana-Sp0 |
| 522 | GalNAca1-3(Fuca1-2)Galb1-4GlcNAcb1-2Mana-Sp0 |
| 523 | Galb1-3GlcNAcb1-2Mana-Sp0 |
| 524 | Gala1-3(Fuca1-2)Galb1-3GlcNAcb1-6GalNAc-Sp14 |
| 525 | Neu5Aca2-3Galb1-3GlcNAcb1-2Mana-Sp0 |
| 526 | Gala1-3Galb1-3GlcNAcb1-2Mana-Sp0 |
| 527 | GalNAcb1-4GlcNAcb1-2Mana-Sp0 |
| 528 | Neu5Aca2-3Galb1-3GalNAcb1-4Galb1-4Glcb-Sp0 |
| 529 | GlcNAcb1-2Mana1-6(GlcNAcb1-4)(GlcNAcb1-2Mana1-3)Manb1-4GlcNAcb1-4(Fuca1-6)GlcNAc-Sp21 |
| 530 | Galb1-4GlcNAcb1-2Mana1-6(GlcNAcb1-4)(Galb1-4GlcNAcb1-2Mana1-3)Manb1-4GlcNAcb1-4(Fuca1-6)GlcNAc-Sp21 |
| 531 | Galb1-4GlcNAcb1-2Mana1-6(Galb1-4GlcNAcb1-4)(Galb1-4GlcNAcb1-2Mana1-3)Manb1-4GlcNAcb1-4(Fuca1-6)GlcNAc-Sp21 |
| 532 | Fuca1-4(Galb1-3)GlcNAcb1-2Mana-Sp0 |
| 533 | Neu5Aca2-3Galb1-4(Fuca1-3)GlcNAcb1-2Mana-Sp0 |
| 534 | GlcNAcb1-3Galb1-4GlcNAcb1-6(GlcNAcb1-3)Galb1-4GlcNAc-Sp0 |
| 535 | GalNAca1-3(Fuca1-2)Galb1-3GalNAcb1-3Gala1-4Galb1-4Glc-Sp21 |
| 536 | Gala1-3(Fuca1-2)Galb1-3GalNAcb1-3Gala1-4Galb1-4Glc-Sp21 |
| 537 | Galb1-3GalNAcb1-3Gal-Sp21 |
| 538 | GlcNAcb1-3Galb1-4GlcNAcb1-2Mana1-6(GlcNAcb1-3Galb1-4GlcNAcb1-2Mana1-3)Manb1-4GlcNAcb1-4GlcNAcb-Sp12 |
| 539 | GlcNAcb1-3Galb1-4GlcNAcb1-2Mana1-6(GlcNAcb1-3Galb1-4GlcNAcb1-2Mana1-3)Manb1-4GlcNAcb1-4GlcNAcb-Sp25 |
| 540 | Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb1-4GlcNAcb-Sp12 |
| 541 | Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb1-4GlcNAcb-Sp24 |
| 542 | Neu5Gca2-3Galb1-4GlcNAcb1-3Galb1-4GlcNAcb1-2Mana1-6(Neu5Gca2-3Galb1-4GlcNAcb1-3Galb1-4GlcNAcb1-2Mana1-3)Manb1-4GlcNAcb1-4GlcNAcb-Sp24 |
| 543 | Fuca1-2Galb1-4GlcNAcb1-3Galb1-4GlcNAcb1-2Mana1-6(Fuca1-2Galb1-4GlcNAcb1-3Galb1-4GlcNAcb1-2Mana1-3)Manb1-4GlcNAcb1-4GlcNAcb-Sp24 |
| 544 | GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-2Mana1-3)Manb1-4GlcNAcb1-4GlcNAcb-Sp12 |
| 545 | GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-2Mana1-3)Manb1-4GlcNAcb1-4GlcNAcb-Sp25 |
| 546 | Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-2Mana1-3)Manb1-4GlcNAcb1-4GlcNAcb-Sp12 |
| 547 | Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-2Mana1-3)Manb1-4GlcNAcb1-4GlcNAcb-Sp24 |
| 548 | GlcNAcb1-3Galb1-4GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |

TABLE 9-continued

| Chart Number | |
|---|---|
| 549 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |
| 550 | Galb1-3GlcNAcb1-3Galb1-4GlcNAcb1-2Mana1-6(Galb1-3GlcNAcb1-3Galb1-4GlcNAcb1-2Mana1-3)Manb1-4GlcNAcb1-4GlcNAc-Sp25 |
| 551 | Neu5Gca2-8Neu5Gca2-3Galb1-4GlcNAc-Sp0 |
| 552 | Neu5Aca2-8Neu5Gca2-3Galb1-4GlcNAc-Sp0 |
| 553 | Neu5Gca2-8Neu5Aca2-3Galb1-4GlcNAc-Sp0 |
| 554 | Neu5Gca2-8Neu5Gca2-3Galb1-4GlcNAcb1-3Galb1-4GlcNAc-Sp0 |
| 555 | Neu5Gca2-8Neu5Gca2-3Galb1-6Galb1-4GlcNAc-Sp0 |
| 556 | Neu5Aca2-8Neu5Aca2-3Galb1-4GlcNAc-Sp0 |
| 557 | GlcNAcb1-3Galb1-4GlcNAcb1-6(GlcNAcb1-3Galb1-4GlcNAcb1-2)Mana1-6(GlcNAcb1-3Galb1-4GlcNAcb1-2Mana1-3)Manb1-4GlcNAcb1-4GlcNAc-Sp24 |
| 558 | Galb1-4GlcNAcb1-3Galb1-4GlcNAcb1-6(Galb1-4GlcNAcb1-3Galb1-4GlcNAcb1-2)Mana1-6(Galb1-4GlcNAcb1-3Galb1-4GlcNAcb1-2Mana1-3)Mana1-4GlcNAcb1-4GlcNAc-Sp24 |
| 559 | Gala1-3Galb1-4GlcNAcb1-2Mana1-6(Gala1-3Galb1-4GlcNAcb1-2Mana1-3)Manb1-4GlcNAcb1-4GlcNAc-Sp24 |
| 560 | GlcNAcb1-3Galb1-4GlcNAcb1-6(GlcNAcb1-3Galb1-3)GalNAca-Sp14 |
| 561 | GalNAcb1-3GlcNAcb-Sp0 |
| 562 | GalNAcb1-4GlcNAcb1-3GalNAcb1-4GlcNAcb-Sp0 |
| 563 | GlcNAcb1-3Galb1-4GlcNAcb1-3Galb1-4GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |
| 564 | Galb1-4GlcNAcb1-3Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |
| 565 | GlcNAb1-3Galb1-3GalNAc-Sp14 |
| 566 | Galb1-3GlcNAcb1-6(Galb1-3)GalNAc-Sp14 |
| 567 | Galb1-4GlcNAcb1-3Galb1-4GlcNAcb1-3Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |
| 568 | (3S)GlcAb1-3Galb1-4GlcNAcb1-3Galb1-4Glc-Sp0 |
| 569 | (3S)GlcAb1-3Galb1-4GlcNAcb1-2Mana-Sp0 |
| 570 | Galb1-3GlcNAcb1-3Galb1-4GlcNAcb1-3Galb1-4GlcNAcb1-6(Galb1-3GlcNAcb1-3Galb1-4GlcNAcb1-3Galb1-4GlcNAb1-2)Mana1-6(Galb1-3GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 571 | Galb1-3GlcNAcb1-3Galb1-4GlcNAcb1-6(Galb1-3GlcNAcb1-3Galb1-4GlcNAb1-2)Mana1-6(Galb1-3GlcNAcb1-3Galb1-4GlcNAcb1-2Mana1-3)Manb1-4GlcNAcb1-4(Fuca1-6)GlcNAcb-Sp24 |
| 572 | Neu5Aca2-8Neu5Aca2-3Galb1-3GalNAcb1-4(Neu5Aca2-3)Galb1-4Glc-Sp21 |
| 573 | GlcNAcb1-3Galb1-4GlcNAcb1-2Mana1-6(GlcNAcb1-3Galb1-4GlcNAcb1-2Mana1-3)Manb1-4GlcNAcb1-4(Fuca1-6)GlcNAcb-Sp24 |
| 574 | Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb1-4(Fuca1-6)GlcNAcb-Sp24 |
| 575 | GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 576 | Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 577 | GlcNAcb1-3Galb1-4GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 578 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 579 | GlcNAcb1-3Galb1-4GlcNAcb1-3Galb1-4GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp19 |
| 580 | Galb1-4GlcNAcb1-3Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp19 |
| 581 | Galb1-4GlcNAcb1-3Galb1-4GlcNAcb1-6(Galb1-4GlcNAcb1-3Galb1-4GlcNAb1-2)Mana1-6(Galb1-4GlcNAcb1-3Galb1-4GlcNAcb1-2Mana1-3)Manb1-4GlcNAcb1-4(Fuca1-6)GlcNAcb-Sp24 |

TABLE 9-continued

| Chart Number | |
|---|---|
| 582 | GlcNAcb1-3Galb1-4GlcNAcb1-3Galb1-4GlcNAcb1-6(GlcNAcb1-3Galb1-4GlcNAcb1-3Galb1-4GlcNAb1-2)Mana1-6(GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 583 | Galb1-4GlcNAcb1-3Galb1-4GlcNAcb1-3Galb1-4GlcNAcb1-6(Galb1-4GlcNAcb1-3Galb1-4GlcNAcb1-3Galb1-4GlcNAb1-2)Mana1-6(Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 584 | GlcNAcb1-3Galb1-4GlcNAcb1-3Galb1-4GlcNAcb1-3Galb1-4GlcNAcb1-6(GlcNAcb1-3Galb1-4GlcNAcb1-3Galb1-4GlcNAcb1-3Galb1-4GlcNAb1-2)Mana1-6(GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 585 | Galb1-4GlcNAcb1-3Galb1-4GlcNAcb1-3Galb1-4GlcNAcb1-3Galb1-4GlcNAcb1-6(Galb1-4GlcNAcb1-3Galb1-4GlcNAcb1-3Galb1-4GlcNAcb1-3Galb1-4GlcNAb1-2)Mana1-6(Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 586 | GlcNAcb1-3Galb1-4GlcNAcb1-3Galb1-4GlcNAcb1-3Galb1-4GlcNAcb1-3Galb1-4GlcNAcb1-6(GlcNAcb1-3Galb1-4GlcNAcb1-3Galb1-4GlcNAcb1-3Galb1-4GlcNAcb1-3Galb1-4GlcNAb1-2)Mana1-6(GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 587 | Galb1-4GlcNAcb1-3Galb1-4GlcNAcb1-3Galb1-4GlcNAcb1-3Galb1-4GlcNAcb1-3Galb1-4GlcNAcb1-6(Galb1-4GlcNAcb1-3Galb1-4GlcNAcb1-3Galb1-4GlcNAcb1-3Galb1-4GlcNAcb1-3Galb1-4GlcNAb1-2)Mana1-6(Galb1-4GlcNAcb1-3Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb-Sp24 |
| 588 | Galb1-4GlcNAcb1-3Galb1-4GlcNAcb1-3GalNAca-Sp14 |
| 589 | Galb1-4GlcNAcb1-3Galb1-4GlcNAcb1-6(Galb1-3)GalNAca-Sp14 |
| 590 | Galb1-4GlcNAcb1-3Galb1-4GlcNAcb1-6(Galb1-4GlcNAcb1-3Galb1-4GlcNAca-Sp14 |
| 591 | Neu5Aca2-3Galb1-4GlcNAcb1-3Galb1-4GlcNAcb1-3GalNAca-Sp14 |
| 592 | GlcNAcb1-3Galb1-4GlcNAcb1-3GalNAca-Sp14 |
| 593 | GlcNAcb1-3Galb1-4GlcNAcb1-6(Galb1-3)GalNAca-Sp14 |
| 594 | GlcNAcb1-3Galb1-4GlcNAcb1-6(GlcNAcb1-3Galb1-4GlcNAcb1-3)GalNAca-Sp14 |
| 595 | Neu5Aca2-3Galb1-4GlcNAcb1-3Galb1-4GlcNAcb1-6(Neu5Aca2-3Galb1-4GlcNAcb1-3Galb1-4GlcNAcb1-3)GalNAca-Sp14 |
| 596 | Neu5Aca2-6Galb1-4GlcNAcb1-3Galb1-4GlcNAcb1-3GalNAca-Sp14 |
| 597 | GlcNAcb1-3Galb1-4GlcNAcb1-3Galb1-4GlcNAcb1-3GalNAca-Sp14 |
| 598 | Galb1-4GlcNAcb1-3Galb1-3GalNAca-Sp14 |
| 599 | Neu5Aca2-3Galb1-4GlcNAcb1-3Galb1-4GlcNAcb1-6(Galb1-3)GalNAca-Sp14 |
| 600 | Neu5Aca2-6Galb1-4GlcNAcb1-3Galb1-4GlcNAcb1-6(Galb1-3)GalNAca-Sp14 |
| 601 | Neu5Aca2-6Galb1-4GlcNAcb1-6(Galb1-3)GalNAca-Sp14 |
| 602 | Neu5Aca2-3Galb1-4GlcNAcb1-3Galb1-4GlcNAcb1-2Mana1-6(Neu5Aca2-3Galb1-4GlcNAcb1-3Galb1-4GlcNAcb1-2Mana1-3)Manb1-4GlcNAcb1-4GlcNAcb-Sp12 |
| 603 | GlcNAcb1-6(Neu5Aca2-3Galb1-3)GalNAca-Sp14 |
| 604 | Neu5Aca2-6Galb1-4GlcNAcb1-3Galb1-4GlcNAcb1-6(Neu5Aca2-6Galb1-4GlcNAcb1-3Galb1-4GlcNAcb1-3)GalNAca-Sp14 |
| 605 | Neu5Aca2-6Galb1-4GlcNAcb1-3Galb1-4GlcNAcb1-3Galb1-4GlcNAcb1-2Mana1-6(Neu5Aca2-6Galb1-4GlcNAcb1-3Galb1-4GlcNAcb1-3Galb1-4GlcNAcb1-2Mana1-3)Manb1-4GlcNAcb1-4GlcNAcb-Sp12 |
| 606 | Neu5Aca2-3Galb1-4GlcNAcb1-3Galb1-4GlcNAcb1-3Galb1-4GlcNAcb1-2Mana1-6(Neu5Aca2-3Galb1-4GlcNAcb1-3Galb1-4GlcNAcb1-3Galb1-4GlcNAcb1-2Mana1-3)Manb1-4GlcNAcb1-4GlcNAcb-Sp12 |
| 607 | Neu5Aca2-6Galb1-4GlcNAcb1-3Galb1-4GlcNAcb1-2Mana1-6(Neu5Aca2-6Galb1-4GlcNAcb1-3Galb1-4GlcNAcb1-2Mana1-3)Manb1-4GlcNAcb1-4GlcNAcb-Sp12 |
| 608 | GlcNAcb1-3Fuca-Sp21 |
| 609 | Galb1-3GalNAcb1-4(Neu5Aca2-8Neu5Aca2-8Neu5Aca2-3)Galb1-4Glcb-Sp21 |

While the invention has been described through specific embodiments, routine modifications will be apparent to those skilled in the art and such modifications are intended to be within the scope of the present invention.

What is claimed is:

1. A method for inhibiting an increase in volume of a tumor, the method comprising contacting Thomsen-Friedenreich (TF) human tumor antigen (TF-Ag) expressing cancer cells in the tumor with a mAb comprising a heavy chain comprising the sequence

```
                                                (SEQ ID NO: 9)
EVQLVESGAEVKKPGASVKVSCKASGYTFTTYWMHWVKQAPGQGLEWIGF

ISPNTDYTEYNQKFRDKATMTADTSISTAYMELSRLRSDDTAVYYCARSF

IGYNFDFWGQGTTLTVSS
``` and a light chain comprising the sequence: (L3)

```
                                               (SEQ ID NO: 12)
DVVMTQSPLSLPVTLGQPASISCRSSQTIVYSNGNTYLEWYLQRPGQSPR

LLIYKVSNRFSGVPDRFSGSGSGTDFTLKISRVEAEDVGVYYCFQGSHVP

FTFGSGTKLEIK (an H3L3 mAb);
``` or a mAb comprising a heavy chain comprising the sequence

```
                                               (SEQ ID NO: 13)
QVQLVQSGAEVKKPGSSVKVSCKASGYTFTTYWMHWVRQAPGQGLEWMGF

ISPNTDYTEYNQKFRDRVTITADKSTSTAYMELSSLRSEDTAVYYCARSF

IGYNFDFWGQGTTVTVS
``` and a light chain (L2a) comprising the sequence

```
                                               (SEQ ID NO: 15)
DIVMTQSPLSLPVTPGEPASISCRSSQTIVYSNGNTYLEWYLQKPGQSPQ

LLIYKVSNRFSGVPDRFSGSGSGTDFTLKISRVEAEDVGVYYCFQGSHVP

FTFGSGTKVDIK (an H2aL2a mAb).
```

2. The method of claim 1, wherein the mAb comprising a heavy chain comprising the sequence of SEQ ID NO: 9 and a light chain comprising the sequence of SEQ ID NO: 12 is used.

3. The method of claim 2, wherein the mAb comprising a heavy chain comprising the sequence of SEQ ID NO: 9 and a light chain comprising the sequence of SEQ ID NO: 12 exhibits increased antibody-dependent cell mediated cytotoxicity (ADCC) of the TF-Ag expressing cancer cells relative to a control value, wherein the control value is ADCC from contacting TF-Ag expressing cancer cells with a mAb comprising a heavy chain comprising the sequence of SEQ ID NO: 8 and a light chain comprising the sequence of SEQ ID NO: 12, or with a chimeric anti-TF Ag mAb, or with a murine anti-TF mAb.

4. The method of claim 1, wherein the mAb comprising a heavy chain comprising the sequence of SEQ. ID NO: 13 and a light chain comprising the sequence of SEQ ID NO: 15 is used.

5. The method of claim 4, wherein the mAb comprising a heavy chain comprising the sequence of SEQ ID NO: 13 and a light chain comprising the sequence of SEQ ID NO: 15 exhibits increased cellular internalization into TF-Ag expressing tumor cells relative to a control value, wherein the control value for internalization of a mAb comprising a heavy chain comprising the sequence of SEQ ID NO: 8 and a light chain comprising the sequence of SEQ ID NO: 12 or a mAb comprising a heavy chain comprising the sequence of SEQ ID NO: 9 and a light chain comprising the sequence of SEQ ID NO: 12 into TF-Ag expressing tumor cells.

6. The method of claim 4, wherein the mAb comprising a heavy chain comprising the sequence of SEQ ID NO: 13 and a light chain comprising the sequence of SEQ ID NO: 15 is conjugated to a chemotherapeutic agent.

7. A method comprising contacting a cancer cell that expresses Thomsen-Friedenreich (TF) human tumor antigen (TF-Ag) with a monoclonal antibody (mAb) or fragment thereof that binds with specificity to TF-Ag, wherein the mAb or the fragment thereof comprises a detectable label, and detecting a signal from the label from the mAb or fragment thereof that is bound to the TF-Ag, the monoclonal antibody or fragment thereof comprising a heavy chain and a light chain, wherein the heavy chain comprises a sequence selected from the group consisting of:

a) the sequence consisting of: (SEQ ID NO: 7)

EVQLVESGAEVKKPGASVKVSCKASGYTFTTYWMHWVRQAPGQGLEWMGF

ISPNTDYTEYNQKFRDRVTMTADTSISTAYMELSRLRSDDTAVYYCARSF

IGYNFDFWGQGTLVTVSS;

b) the sequence consisting of: (SEQ ID NO: 8)

EVQLLESGAELKKPGASVKVSCKASGYTFTTYWMHWVRQAPGQGLEWMGF

ISPNTDYTEYNQKFRDRVTLTADKSSSTAYMELSSLTSEDTAVYYCARSF

IGYNFDFWGQGTTVTVSS;

c) the sequence consisting of: (SEQ ID NO: 9)

EVQLVESGAEVKKPGASVKVSCKASGYTFTTYWMHWVKQAPGQGLEWIGF

ISPNTDYTEYNQKFRDKATMTADTSISTAYMELSRLRSDDTAVYYCARSF

IGYNFDFWGQGTTLTVSS, d) the sequence consisting of: (SEQ ID NO: 13)

QVQLVQSGAEVKKPGSSVKVSCKASGYTFTTYWMHWVRQAPGQGLEWMGF

ISPNTDYTEYNQKFRDRVTITADKSTSTAYMELSSLRSEDTAVYYCARSF

IGYNFDFWGQGTTVTVS;

e) the sequence consisting of: (SEQ ID NO: 14)

EGQLLESGAELAKPGASVKMSCKASGYTFTTYWMHWVKKRPGQGLEWIGF

ISPNTDYTEYNQKFRDKATLTADKSSTTAYMQLSSLTSDDSAVYYCARSF

IGYNFDFWGQGTTLTVSS;

and combinations thereof; and wherein the light chain comprises a sequence selected from the group consisting of:

f) the sequence consisting of: (SEQ ID NO: 10)

DVVMTQSPLSLPVTLGQPASISCRSSQTIVYSNGNTYLEWFQQRPGQSPR

LLIYKVSNRFSGVPDRFSGSGSGTDFTLKISRVEAEDVGVYYCFQGSHVP

FTFGSGTKLEIK;

g) the sequence consisting of: (SEQ ID NO: 11)

DIVMTQTPLSLPVTLGQPASISCRSSQTIVYSNGNTYLEWFQQRPGQSPR

LLIYKVSNRFSGVPDRFSGSGSGTDFTLKISRVEAEDVGVYYCFQGSHVP

FTFGSGTKLEIK;

h) the sequence consisting of: (SEQ ID NO: 12)

DVVMTQSPLSLPVTLGQPASISCRSSQTIVYSNGNTYLEWYLQRPGQSPR

LLIYKVSNRFSGVPDRFSGSGSGTDFTLKISRVEAEDVGVYYCFQGSHVP

FTFGSGTKLEIK;

i) the sequence consisting of: (SEQ ID NO: 15)

DIVMTQSPLSLPVTPGEPASISCRSSQTIVYSNGNTYLEWYLQKPGQSPQ

LLIYKVSNRFSGVPDRFSGSGSGTDFTLKISRVEAEDVGVYYCFQGSHVP

FTFGSGTKVDIK;

and j) the sequence consisting of: (SEQ ID NO: 16)

ELVMTQTPLSLPVNLGDQASISCRSSQTIVYSNGNTYLEWYLQKPGQSPK

LLIYKVSNRFSGVPDRFSGSGSGTDFTLKISRVEADDLGVYYCFQGSHVP

FTFGSGTKLEIK.

8. The method of claim 7, wherein the detectable label comprises a radioactive isotope.

9. The method of claim 7, wherein the mAb comprises a heavy chain comprising the sequence of SEQ ID NO: 9 and a light chain comprising the sequence of SEQ ID NO: 12.

10. The method of claim 9, wherein the detectable label comprises a radioactive isotope.

11. The method of claim 7, wherein the mAb comprises a heavy chain comprising the sequence of SEQ ID NO: 13 and a light chain comprising the sequence of SEQ ID NO: 15.

12. The method of claim 11, wherein the detectable label comprises a radioactive isotope.

\* \* \* \* \*

```
                          SEQUENCE LISTING

<160> NUMBER OF SEQ ID NOS: 17

<210> SEQ ID NO 1
<211> LENGTH: 11
<212> TYPE: PRT
<213> ORGANISM: mouse

<400> SEQUENCE: 1

Ser Gly Tyr Thr Phe Thr Thr Tyr Trp Met His
1               5                   10

<210> SEQ ID NO 2
<211> LENGTH: 17
<212> TYPE: PRT
<213> ORGANISM: mouse

<400> SEQUENCE: 2

Phe Ile Ser Pro Asn Thr Asp Tyr Thr Glu Tyr Asn Gln Lys Phe Arg
1               5                   10                  15

Asp

<210> SEQ ID NO 3
<211> LENGTH: 15
<212> TYPE: PRT
<213> ORGANISM: mouse

<400> SEQUENCE: 3

Arg Ser Phe Ile Gly Tyr Asn Phe Asp Phe Trp Gly Gln Gly Thr
1               5                   10                  15

<210> SEQ ID NO 4
<211> LENGTH: 18
<212> TYPE: PRT
<213> ORGANISM: mouse

<400> SEQUENCE: 4

Cys Arg Ser Ser Gln Thr Ile Val Tyr Ser Asn Gly Asn Thr Tyr Leu
1               5                   10                  15

Glu Trp

<210> SEQ ID NO 5
<211> LENGTH: 11
<212> TYPE: PRT
<213> ORGANISM: mouse

<400> SEQUENCE: 5

Lys Val Ser Asn Arg Phe Ser Gly Val Pro Asp
1               5                   10

<210> SEQ ID NO 6
<211> LENGTH: 13
<212> TYPE: PRT
<213> ORGANISM: mouse

<400> SEQUENCE: 6

Cys Phe Gln Gly Ser His Val Pro Phe Thr Gly Ser Gly
1               5                   10

<210> SEQ ID NO 7
<211> LENGTH: 118
<212> TYPE: PRT
```

<213> ORGANISM: artificial sequence
<220> FEATURE:
<223> OTHER INFORMATION: humanized antibody chain

<400> SEQUENCE: 7

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Phe Ile Ser Pro Asn Thr Asp Tyr Thr Glu Tyr Asn Gln Lys Phe
    50                  55                  60

Arg Asp Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Ile Gly Tyr Asn Phe Asp Phe Trp Gly Gln Gly Thr
            100                 105                 110

Leu Val Thr Val Ser Ser
        115

<210> SEQ ID NO 8
<211> LENGTH: 118
<212> TYPE: PRT
<213> ORGANISM: artificial sequence
<220> FEATURE:
<223> OTHER INFORMATION: humanized antibody chain

<400> SEQUENCE: 8

Glu Val Gln Leu Leu Glu Ser Gly Ala Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Phe Ile Ser Pro Asn Thr Asp Tyr Thr Glu Tyr Asn Gln Lys Phe
    50                  55                  60

Arg Asp Arg Val Thr Leu Thr Ala Asp Lys Ser Ser Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Ser Phe Ile Gly Tyr Asn Phe Asp Phe Trp Gly Gln Gly Thr
            100                 105                 110

Thr Val Thr Val Ser Ser
        115

<210> SEQ ID NO 9
<211> LENGTH: 118
<212> TYPE: PRT
<213> ORGANISM: artificial sequence
<220> FEATURE:
<223> OTHER INFORMATION: humanized antibody chain

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Lys Gln Ala Pro Gly Gln Gly Leu Glu Trp Ile
            35                  40                  45

Gly Phe Ile Ser Pro Asn Thr Asp Tyr Thr Glu Tyr Asn Gln Lys Phe
 50                  55                  60

Arg Asp Lys Ala Thr Met Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Phe Ile Gly Tyr Asn Phe Asp Phe Trp Gly Gln Gly Thr
                100                 105                 110

Thr Leu Thr Val Ser Ser
                115

<210> SEQ ID NO 10
<211> LENGTH: 112
<212> TYPE: PRT
<213> ORGANISM: artificial sequence
<220> FEATURE:
<223> OTHER INFORMATION: humanized antibody chain

<400> SEQUENCE: 10

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Thr Ile Val Tyr Ser
                 20                  25                  30

Asn Gly Asn Thr Tyr Leu Glu Trp Phe Gln Gln Arg Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Phe Thr Phe Gly Ser Gly Thr Lys Leu Glu Ile Lys
                100                 105                 110

<210> SEQ ID NO 11
<211> LENGTH: 112
<212> TYPE: PRT
<213> ORGANISM: artificial sequence
<220> FEATURE:
<223> OTHER INFORMATION: humanized antibody chain

<400> SEQUENCE: 11

Asp Ile Val Met Thr Gln Thr Pro Leu Ser Leu Pro Val Thr Leu Gly
 1               5                  10                  15

Gln Pro Ala Ser Ile Ser Cys Arg Ser Ser Gln Thr Ile Val Tyr Ser
                 20                  25                  30

Asn Gly Asn Thr Tyr Leu Glu Trp Phe Gln Gln Arg Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Phe Thr Phe Gly Ser Gly Thr Lys Leu Glu Ile Lys

<210> SEQ ID NO 12
<211> LENGTH: 112
<212> TYPE: PRT
<213> ORGANISM: artificial sequence
<220> FEATURE:
<223> OTHER INFORMATION: humanized antibody chain

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val Tyr Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 13
<211> LENGTH: 117
<212> TYPE: PRT
<213> ORGANISM: artificial sequence
<220> FEATURE:
<223> OTHER INFORMATION: humanized antibody chain

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Phe Ile Ser Pro Asn Thr Asp Tyr Thr Glu Tyr Asn Gln Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Ile Gly Tyr Asn Phe Asp Phe Trp Gly Gln Gly Thr
            100                 105                 110

Thr Val Thr Val Ser
        115

<210> SEQ ID NO 14
<211> LENGTH: 118
<212> TYPE: PRT
<213> ORGANISM: artificial sequence
<220> FEATURE:
<223> OTHER INFORMATION: humanized antibody chain

<400> SEQUENCE: 14

Glu Gly Gln Leu Leu Glu Ser Gly Ala Glu Leu Ala Lys Pro Gly Ala
1               5                   10                  15

-continued

Ser Val Lys Met Ser Cys Lys Ala Ser Gly Tyr Thr Phe Thr Thr Tyr
            20                  25                  30

Trp Met His Trp Val Lys Lys Arg Pro Gly Gln Gly Leu Glu Trp Ile
        35                  40                  45

Gly Phe Ile Ser Pro Asn Thr Asp Tyr Thr Glu Tyr Asn Gln Lys Phe
    50                  55                  60

Arg Asp Lys Ala Thr Leu Thr Ala Asp Lys Ser Ser Thr Thr Ala Tyr
65                  70                  75                  80

Met Gln Leu Ser Ser Leu Thr Ser Asp Asp Ser Ala Val Tyr Tyr Cys
                85                  90                  95

Ala Arg Ser Phe Ile Gly Tyr Asn Phe Asp Phe Trp Gly Gln Gly Thr
            100                 105                 110

Thr Leu Thr Val Ser Ser
        115

<210> SEQ ID NO 15
<211> LENGTH: 112
<212> TYPE: PRT
<213> ORGANISM: artificial sequence
<220> FEATURE:
<223> OTHER INFORMATION: humanized antibody chain

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val Tyr Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Ser Gly Thr Lys Val Asp Ile Lys
            100                 105                 110

<210> SEQ ID NO 16
<211> LENGTH: 112
<212> TYPE: PRT
<213> ORGANISM: artificial sequence
<220> FEATURE:
<223> OTHER INFORMATION: humanized antibody chain

<400> SEQUENCE: 16

Glu Leu Val Met Thr Gln Thr Pro Leu Ser Leu Pro Val Asn Leu Gly
1               5                   10                  15

Asp Gln Ala Ser Ile Ser Cys Arg Ser Ser Gln Thr Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Gly

```
                        85                  90                  95
Ser His Val Pro Phe Thr Phe Gly Ser Gly Thr Lys Leu Glu Ile Lys
            100                 105                 110

<210> SEQ ID NO 17
<211> LENGTH: 112
<212> TYPE: PRT
<213> ORGANISM: mouse

<400> SEQUENCE: 17

Glu Leu Val Met Thr Gln Thr Pro Leu Ser Leu Pro Val Asn Leu Gly
1               5                   10                  15

Asp Gln Ala Ser Ile Ser Cys Arg Ser Ser Gln Thr Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```